(12) United States Patent
Park et al.

(10) Patent No.: US 10,283,716 B2
(45) Date of Patent: May 7, 2019

(54) COMPOUND FOR ORGANIC ELECTRIC ELEMENT, ORGANIC ELECTRIC ELEMENT USING THE SAME, AND ELECTRONIC DEVICE COMPRISING SAME

(71) Applicant: DUK SAN NEOLUX CO., LTD., Cheonan-si, Chungcheongnam-do (KR)

(72) Inventors: Jung Cheol Park, Suwon-si (KR); Sun Hee Lee, Hwaseong-si (KR); Mun Jae Lee, Cheonan-si (KR); Soung Yun Mun, Cheonan-si (KR); Bum Sung Lee, Cheonan-si (KR); Jin Ho Yun, Cheonan-si (KR); Yun Sun Byun, Daegu (KR); Jae Taek Kwon, Cheonan-si (KR); Jung Wook Lee, Gunsan-si (KR)

(73) Assignee: DUK SAN NEOLUX CO., LTD., Cheonan-si, Chungcheon (KR)

( * ) Notice: Subject to any disclaimer, the term of this patent is extended or adjusted under 35 U.S.C. 154(b) by 0 days.

(21) Appl. No.: 15/549,467

(22) PCT Filed: Feb. 4, 2016

(86) PCT No.: PCT/KR2016/001226
§ 371 (c)(1),
(2) Date: Aug. 8, 2017

(87) PCT Pub. No.: WO2016/129861
PCT Pub. Date: Aug. 18, 2016

(65) Prior Publication Data
US 2018/0026187 A1    Jan. 25, 2018

(30) Foreign Application Priority Data
Feb. 9, 2015 (KR) .................. 10-2015-0019340

(51) Int. Cl.
*C07C 15/24* (2006.01)
*C09K 11/06* (2006.01)
(Continued)

(52) U.S. Cl.
CPC .......... *H01L 51/006* (2013.01); *C07C 13/567* (2013.01); *C07C 15/24* (2013.01);
(Continued)

(58) Field of Classification Search
CPC ............... H01L 51/006; H01L 51/0061; H01L 51/5262; C07C 211/58; C07C 211/61;
(Continued)

(56) References Cited

U.S. PATENT DOCUMENTS

2013/0134405 A1   5/2013   Wang et al.
2014/0054559 A1*  2/2014   Kim .................... H01L 51/0094
                                                              257/40
(Continued)

FOREIGN PATENT DOCUMENTS

KR   10-2011-0000006 A        1/2011
KR   10-2013-0135516      *  12/2013
(Continued)

OTHER PUBLICATIONS

KR 10-2011-0000006, unverified machine translation from KIPO. Jan. 3, 2011. (Year: 2011).*
(Continued)

*Primary Examiner* — Daniel R Carcanague
(74) *Attorney, Agent, or Firm* — Vorys, Sater, Seymour & Pease LLP; Mih Suhn Koh

(57) ABSTRACT

Provided is a novel compound for EBL capable of improving the light emitting efficiency, stability and life span of a device, and an organic electric element and an electronic device using the same.

12 Claims, 1 Drawing Sheet

(51) Int. Cl.
*H01L 51/00* (2006.01)
*H01L 51/50* (2006.01)
*H01L 51/52* (2006.01)
*H01L 51/56* (2006.01)
*C07C 13/567* (2006.01)
*C07C 211/58* (2006.01)
*C07C 211/61* (2006.01)
*C07D 213/73* (2006.01)
*C07D 307/91* (2006.01)
*C07D 333/76* (2006.01)

(52) U.S. Cl.
CPC .......... *C07C 211/58* (2013.01); *C07C 211/61* (2013.01); *C07D 213/73* (2013.01); *C07D 307/91* (2013.01); *C07D 333/76* (2013.01); *C09K 11/06* (2013.01); *H01L 51/0052* (2013.01); *H01L 51/0058* (2013.01); *H01L 51/0061* (2013.01); *H01L 51/50* (2013.01); *H01L 51/5262* (2013.01); *C07B 2200/05* (2013.01); *C07C 2603/18* (2017.05); *C07C 2603/94* (2017.05); *H01L 51/0003* (2013.01); *H01L 51/0056* (2013.01); *H01L 51/0067* (2013.01); *H01L 51/0073* (2013.01); *H01L 51/0074* (2013.01); *H01L 51/5056* (2013.01); *H01L 51/56* (2013.01); *H01L 2251/552* (2013.01)

(58) Field of Classification Search
CPC ... C07D 213/73; C07D 307/91; C07D 333/76
USPC .......................................................... 549/26
See application file for complete search history.

(56) References Cited

U.S. PATENT DOCUMENTS

| | | | |
|---|---|---|---|
| 2014/0175395 A1 | 6/2014 | Kim et al. | |
| 2014/0197389 A1* | 7/2014 | Adamovich | ........ H01L 51/5016 257/40 |
| 2016/0211456 A1* | 7/2016 | Yen | ..................... H01L 51/0056 |
| 2018/0033966 A1* | 2/2018 | Park | ....................... C07C 211/58 |

FOREIGN PATENT DOCUMENTS

| | | | | |
|---|---|---|---|---|
| KR | 10-2014-0138267 | * | 10/2014 | |
| WO | WO2010062107 | * | 6/2010 | |
| WO | WO2013120577 | * | 8/2013 | |
| WO | 2013/150674 A1 | | 10/2013 | |
| WO | 2014/058232 A2 | | 4/2014 | |
| WO | WO-2016060463 A2 | * | 4/2016 | ............ C07D 209/08 |
| WO | WO2016129867 | * | 8/2016 | |
| WO | WO2016137148 | * | 9/2016 | |
| WO | WO-2017052129 A1 | * | 3/2017 | ............. C07C 13/72 |
| WO | WO-2017105078 A1 | * | 6/2017 | ............ C07D 403/12 |
| WO | WO-2017116044 A1 | * | 7/2017 | |
| WO | WO-2017122978 A1 | * | 7/2017 | ........... C07D 209/82 |
| WO | WO-2017122988 A1 | * | 7/2017 | ........... C07C 211/54 |

OTHER PUBLICATIONS

Lee; Bull. Korean Chem. Soc. 2011, vol. 32, No. 5,, 1475-1482. (Year: 2011).*
Jeon; Dyes and Pigments 2011, 89, 29-36. (Year: 2011).*
Lee; Bull. Korean Chem. Soc. 2009, 30, 647-652. (Year: 2009).*
Lee; Dyes and Pigments 2013, 98, 471-478. (Year: 2013).*

* cited by examiner

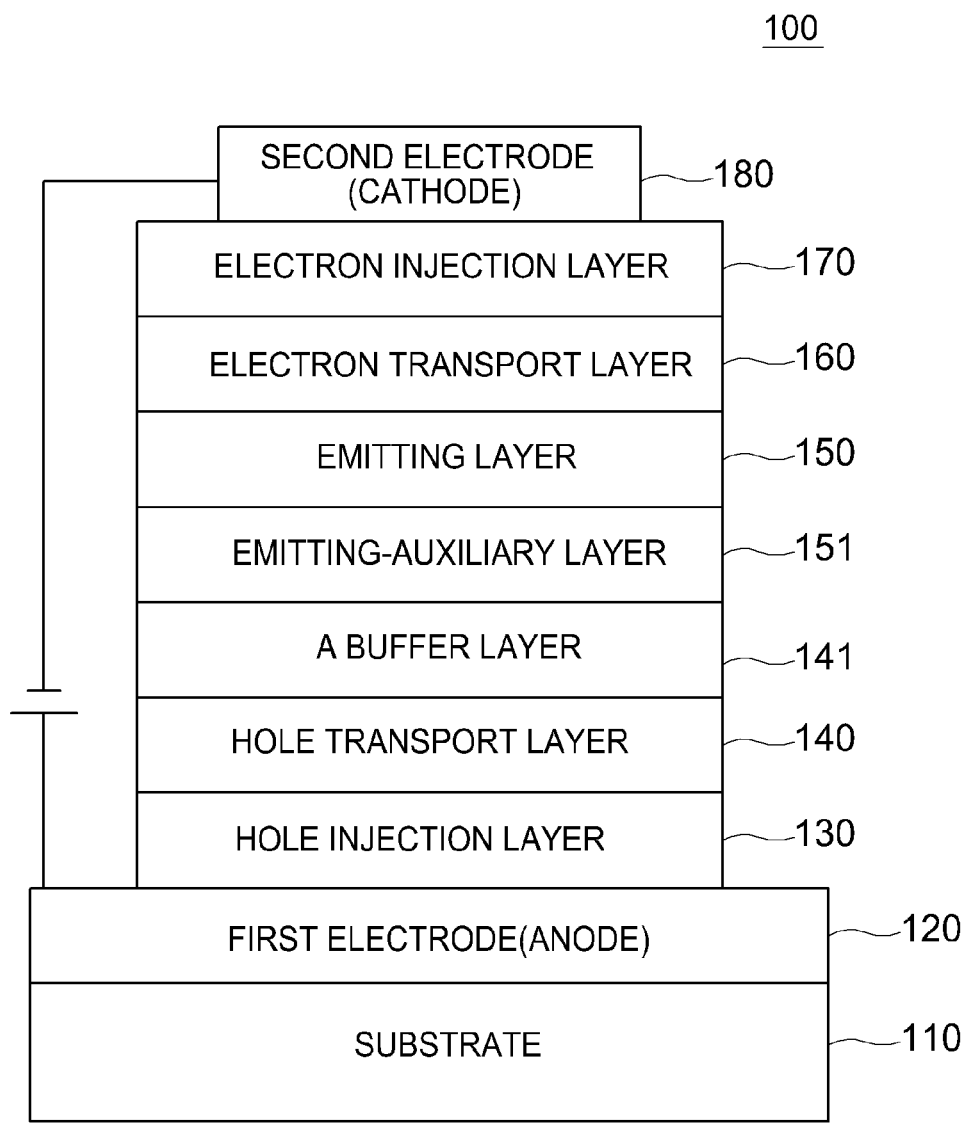

COMPOUND FOR ORGANIC ELECTRIC ELEMENT, ORGANIC ELECTRIC ELEMENT USING THE SAME, AND ELECTRONIC DEVICE COMPRISING SAME

BACKGROUND

Technical Field

The present invention relates to compound for organic electric element, organic electric element using the same, and an electronic device thereof.

Background Art

In general, organic light emitting phenomenon refers to a phenomenon that converts electric energy into light energy by using an organic material. An organic electric element using an organic light emitting phenomenon usually has a structure including an anode, a cathode, and an organic material layer interposed therebetween. Here, in order to increase the efficiency and stability of the organic electronic element, the organic material layer is often composed of a multi-layered structure composed of different materials, and for example, may include a hole injection layer, a hole transport layer, an emitting layer, an electron transport layer, an electron injection layer and the like.

A material used as an organic material layer in an organic electric element may be classified into a light emitting material and a charge transport material, such as a hole injection material, a hole transport material, an electron transport material, an electron injection material and the like depending on its function.

The most problematic issues in an organic electric element are life span and efficiency, and as the display becomes larger, such efficiency and life span problems must be solved.

Efficiency, life span, driving voltage and the like are related to each other. As the efficiency is increased, the driving voltage is relatively decreased, and as the driving voltage drops, the crystallization of the organic material due to joule heating generated during driving is reduced, and as a result, the life span tends to increase.

However, simply improving the organic material layer can not maximize the efficiency. This is because, when the optimal combination of the energy level and T1 value between each organic material layer and the intrinsic properties (mobility, interface characteristics, etc.) of the material are achieved, long life and high efficiency can be achieved at the same time.

Further, in order to solve the emission problem in the a hole transport layer in recent organic electric element, an emitting-auxiliary layer must be present between the hole transport layer and an emitting layer, and it is necessary to develop different emitting-auxiliary layers according to the respective emitting layers (R, G, B).

In general, electrons are transferred from the electron transport layer to the light emitting layer, and holes are transferred from the hole transport layer to the light emitting layer to generate excitons by recombination.

However, the material used for the hole transport layer has a low HOMO value and therefore has a low T1 value. As a result, the exciton generated in the light emitting layer is transferred to the hole transport layer, resulting in charge unbalance in the emitting layer, and light is emitted at the interface of the hole transport layer.

When light is emitted from the interface of the hole transport layer, the coland Purity and efficiency of the organic electronic device are lowered and the life span is shortened. Therefore, it is urgently required to develop a light emitting auxiliary layer having a high T 1 value and a HOMO level between the HOMO energy level of the hole transport layer and the HOMO energy level of the light emitting layer.

In addition, it is necessary to develop a hole injection layer material that retards penetration/diffusion of metal oxides from an anode electrode (ITO) into an organic material layer, which is one cause for the shortened life span of an organic electric element, and has stability against Joule heat generated during the operation of an organic electric element, that is, a high glass transition temperature. Also, it has been reported that a low glass transition temperature of a hole transport layer material has a great effect on the life span of an organic electric element because the uniformity of a thin film surface collapses during the operation of the element. In general, deposition is a main method of forming an OLED, and thus it is necessary to develop a material that is durable to such a deposition method, that is, a highly heat-resistant material.

That is, in order to sufficiently exhibit the excellent characteristics of the organic electric element, A material for forming an organic material layer in an element such as a hole injection material, a hole transport material, a light emitting material, an electron transport material, an electron injection material, an emitting-auxiliary layer material should be supported by stable and efficient materials. However, such a stable and efficient organic material layer material for an organic electric element has not been sufficiently developed yet. Therefore, development of new materials is continuously required, and development of materials for the emitting-auxiliary layer and the hole transport layer is urgently required.

DETAILED DESCRIPTION OF THE INVENTION

Summary

In order to solve the problems of the background art described above, an aspect of the present invention is to provide a compound which allows an organic electric element to further improve high luminous efficiency, stability life span.

An object of the present invention is to provide a compound, an organic electric element using the same and an electronic device thereof.

Technical Solution

The present invention provides a compound represented by Formula below.

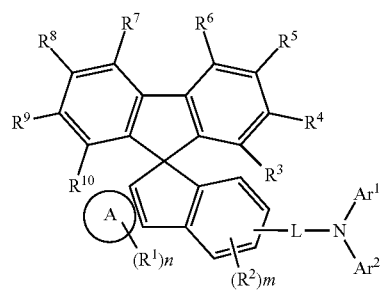

Also, the present invention provides an organic electric element using the compound represented by the Formula and an electronic device thereof.

Effects of the Invention

By using the compound according to the present invention, it is possible to achieve a high luminous efficiency, a low driving voltage, and a high heat resistance of the element, and can greatly improve the coland Purity and lifetime of the element.

BRIEF DESCRIPTION OF THE DRAWINGS

The FIGURE illustrates an example of an organic electric element according to the present invention.
- 100: organic electric element,
- 110: substrate
- 120: the first electrode (anode),
- 130: the hole injection layer
- 140: the hole transport layer,
- 141: a buffer layer
- 150: the emitting layer,
- 151: the emitting auxiliary layer
- 160: the electron transport layer,
- 170: the electron injection layer
- 180: the second electrode (cathode)

DETAILED DESCRIPTION

Hereinafter, some embodiments of the present invention will be described in detail. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if a component is described as being "connected", "coupled", or "connected" to another component, the component may be directly connected or connected to the other component, but another component may be "connected", "coupled" or "connected" between each component.

As used in the specification and the accompanying claims, unless otherwise stated, the following is the meaning of the term as follows.

Unless otherwise stated, the term "halo" or "halogen", as used herein, includes fluorine, bromine, chlorine, or iodine.

Unless otherwise stated, the term "alkyl" or "alkyl group", as used herein, has a single bond of 1 to 60 carbon atoms, and means saturated aliphatic functional radicals including a linear alkyl group, a branched chain alkyl group, a cycloalkyl group (alicyclic), an cycloalkyl group substituted with a alkyl or an alkyl group substituted with a cycloalkyl.

Unless otherwise stated, the term "haloalkyl" or "halogen alkyl", as used herein, includes an alkyl group substituted with a halogen.

Unless otherwise stated, the term "heteroalkyl", as used herein, means alkyl substituted one or more of carbon atoms consisting of an alkyl with hetero atom.

Unless otherwise stated, the term "alkenyl" or "alkynyl", as used herein, has double or triple bonds of 2 to 60 carbon atoms, but is not limited thereto, and includes a linear or a branched chain group.

Unless otherwise stated, the term "cycloalkyl", as used herein, means alkyl forming a ring having 3 to 60 carbon atoms, but is not limited thereto.

Unless otherwise stated, the term "alkoxyl group", "alkoxy group" or "alkyloxy group", as used herein, means an oxygen radical attached to an alkyl group, but is not limited thereto, and has 1 to 60 carbon atoms.

Unless otherwise stated, the term "alkenoxyl group", "alkenoxy group", "alkenyloxy group" or "alkenyloxy group", as used herein, means an oxygen radical attached to an alkenyl group, but is not limited thereto, and has 2 to 60 carbon atoms.

Unless otherwise stated, the term "aryloxyl group" or "aryloxy group", as used herein, means an oxygen radical attached to an aryl group, but is not limited thereto, and has 6 to 60 carbon atoms.

Unless otherwise stated, the term "aryl group" or "arylene group", as used herein, has 6 to 60 carbon atoms, but is not limited thereto. Herein, the aryl group or arylene group means a monocyclic and Polycyclic aromatic group, and may also be formed in conjunction with an adjacent group. Examples of "aryl group" may include a phenyl group, a biphenyl group, a fluorene group, or a spirofluorene group.

The prefix "aryl" or "ar" means a radical substituted with an aryl group. For example, an arylalkyl may be an alkyl substituted with an aryl, and an arylalkenyl may be an alkenyl substituted with aryl, and a radical substituted with an aryl has a number of carbon atoms as defined herein.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substituted with an arylcarbonyl, wherein the arylcarbonyl may be a carbonyl substituted with an aryl.

Unless otherwise stated, the term "heteroalkyl", as used herein, means alkyl containing one or more of hetero atoms.

Unless otherwise stated, the term "heteroaryl group" or "heteroarylene group", as used herein, means a C2 to C60 aryl containing one or more of hetero atoms or arylene group, but is not limited thereto, and includes at least one of monocyclic and polycyclic rings, and may also be formed in conjunction with an adjacent group.

Unless otherwise stated, the term "heterocyclic group", as used herein, contains one or more heteroatoms, but is not limited thereto, has 2 to 60 carbon atoms, includes any one of monocyclic and Polycyclic rings, and may include heteroaliphadic ring and/or heteroaromatic ring. Also, the heterocyclic group may also be formed in conjunction with an adjacent group.

Unless otherwise stated, the term "heteroatom", as used herein, represents at least one of N, O, S, P, or Si.

Also, the term "heterocyclic group" may include a ring containing $SO_2$ instead of carbon consisting of cycle. For example, "heterocyclic group" includes compound below.

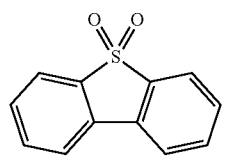 [SMILES: O=S1(=O)c2ccccc2-c2ccccc21]

Unless otherwise stated, the term "aliphatic", as used herein, means an aliphatic hydrocarbon having 1 to 60 carbon atoms, and the term "aliphatic ring", as used herein, means an aliphatic hydrocarbon ring having 3 to 60 carbon atoms.

Unless otherwise stated, the term "ring", as used herein, means an aliphatic ring having 3 to 60 carbon atoms, or an aromatic ring having 6 to 60 carbon atoms, or a hetero ring having 2 to 60 carbon atoms, or a fused ring formed by the combination of them, and includes a saturated or unsaturated ring.

Other hetero compounds or hetero radicals other than the above-mentioned hetero compounds contain, but are not limited thereto, one or more heteroatoms.

Unless otherwise stated, the term "carbonyl", as used herein, is represented by —COR', wherein R' may be hydrogen, an alkyl having 1 to 20 carbon atoms, an aryl having 6 to 30 carbon atoms, a cycloalkyl having 3 to 30 carbon atoms, an alkenyl having 2 to 20 carbon atoms, an alkynyl having 2 to 20 carbon atoms, or the combination of these.

Unless otherwise stated, the term "ether", as used herein, is represented by —R—O—R', wherein R or R' may be independently hydrogen, an alkyl having 1 to 20 carbon atoms, an aryl having 6 to 30 carbon atoms, a cycloalkyl having 3 to 30 carbon atoms, an alkenyl having 2 to 20 carbon atoms, an alkynyl having 2 to 20 carbon atoms, or the combination of these.

Unless otherwise stated, the term "substituted or unsubstituted", as used herein, means that substitution is substituted by at least one substituent selected from the group consisting of, but is not limited thereto, deuterium, halogen, an amino group, a nitrile group, a nitro group, a $C_1$-$C_{20}$ alkyl group, a $C_1$-$C_{20}$ alkoxyl group, a $C_1$-$C_{20}$ alkylamine group, a $C_1$-$C_{20}$ alkylthiopen group, a $C_6$-$C_{20}$ arylthiopen group, a $C_2$-$C_{20}$ alkenyl group, a $C_2$-$C_{20}$ alkynyl group, a $C_3$-$C_{20}$ cycloalkyl group, a $C_6$-$C_{20}$ aryl group, a $C_6$-$C_{20}$ aryl group substituted by deuterium, a $C_8$-$C_{20}$ arylalkenyl group, a silane group, a boron group, a germanium group, and a $C_2$-$C_{20}$ heterocyclic group.

Unless otherwise expressly stated, the Formula used in the present invention, as used herein, is applied in the same manner as the substituent definition according to the definition of the exponent of the following Formula.

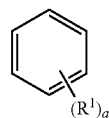

$(R^1)_a$ wherein, when a is an integer of zero, the substituent $R^1$ is absent, when a is an integer of 1, the sole substituent $R^1$ is linked to any one of the carbon constituting the benzene ring, when a is an integer of 2 or 3, each substituent $R^1$'s may be the same and different, when a is an integer of 4 to 6, and is linked to the benzene ring in a similar manner, whereas the indication of hydrogen bound to the carbon forming the benzene ring is omitted.

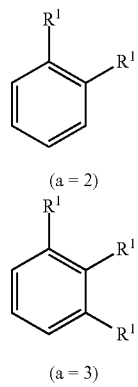

(a = 2)

(a = 3)

Hereinafter, a compound according to an aspect of the present invention and an organic electric element comprising the same will be described.

According to a specific example, the present invention provides a compound represented Formula (1) below.

<Formula (1)>

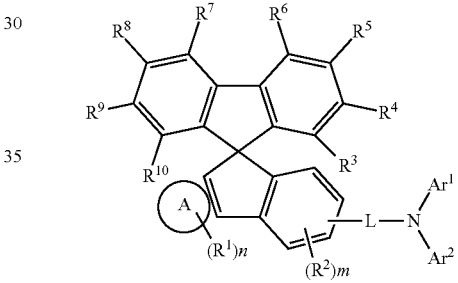

In the Formula (1), $R^1$, $R^2$, $R^3$, $R^4$, $R^5$, $R^6$, $R^7$, $R^8$, $R^9$ and $R^{10}$ are each independently selected from a hydrogen; a deuterium; a halogen; the group consisting of a $C_6$-$C_{60}$ aryl group; a fluorenyl group; a $C_2$-$C_{60}$ heterocyclic group including at least one hetero atom of O, N, S, Si and P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; and -L'-N($R_a$)($R_b$) (where, L' may be selected from the group consisting of a single bond; a $C_6$-$C_{60}$ arylene group; a fluorenylene group; a fused ring group of a $C_3$-$C_{60}$ aliphatic ring and a $C_6$-$C_{60}$ aromatic ring; and a $C_2$-$C_{60}$ heterocyclic, and the $R_a$ and $R_b$ may be independently selected from the group consisting of a $C_6$-$C_{60}$ aryl group; a fluorenyl group; a fused ring group of a $C_3$-$C_{60}$ aliphatic ring and a $C_6$-$C_{60}$ aromatic ring; and a $C_2$-$C_{60}$ heterocyclic group containing at least one hetero atom of O, N, S, Si, and P)

A is an aryl group of $C_{10}$

L may be selected from the group consisting of a single bond; a $C_6$-$C_{60}$ arylene group; a fluorenylene group; a fused ring group of a $C_3$-$C_{60}$ aliphatic ring and a $C_6$-$C_{60}$ aromatic ring; a $C_2$-$C_{60}$ heterocyclic group including at least one hetero atom of O, N, S, Si and P, $Ar^1$, $Ar^2$ are each independently selected from the group consisting of a $C_6$-$C_{60}$ aryl group; a fluorenyl group; a $C_2$-$C_{60}$ heterocyclic group including at least one hetero atom of O, N, S, Si and P; a fused ring group of a $C_3$-$C_{60}$ aliphatic ring and a $C_6$-$C_{60}$ aromatic ring; and -L'-N($R_a$)($R_b$); or $Ar^1$, $Ar^2$ may combine to form a ring, m is an integer of 0 to 3, n is an integer of 0 to 6, (where, aryl group, hetero aryl group, fluorenyl group, arylene group, heterocyclic group, fused ring group may be substituted by one or more of substituents selected from the group consisting of deuterium; halogen; a silane group; a siloxan group; a boron group; a germanium group; a cyano group; a nitro group; -L'-N($R_a$)($R_b$); a $C_1$-$C_{20}$ alkylthio group; a $C_1$-$C_{20}$ alkoxyl group; a $C_1$-$C_{20}$ alkyl group; a $C_2$-$C_{20}$ alkenyl group; a $C_2$-$C_{20}$ alkynyl group; a $C_6$-$C_{20}$ aryl group; a $C_6$-$C_{20}$ aryl group substituted by deuterium; fluorenyl group; a $C_2$-$C_{20}$ heterocyclic group; a $C_3$-$C_{20}$ cycloalkyl group; a $C_7$-$C_{20}$ arylalkyl group, and a $C_8$-$C_{20}$ arylalkenyl group, and also may combine to each other to form a ring, wherein 'ring' means an aliphatic ring having 3 to 60 carbon atoms, or an aromatic ring having 6 to 60 carbon atoms, or a hetero ring having 2 to 60 carbon atoms, or a fused ring formed by the combination of them, and includes a saturated or unsaturated ring.)

According to a specific example, the Formula (1) provides the compound represented Formula (2) to Formula (4) below.

<Formula (2)>

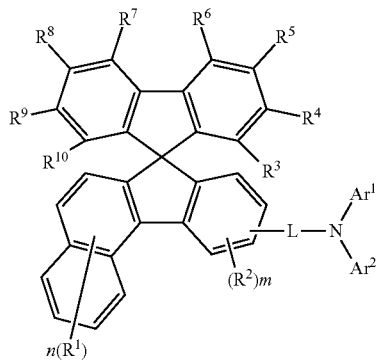

<Formula (3)>

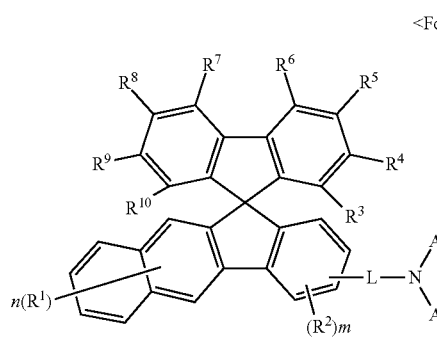

<Formula (4)>

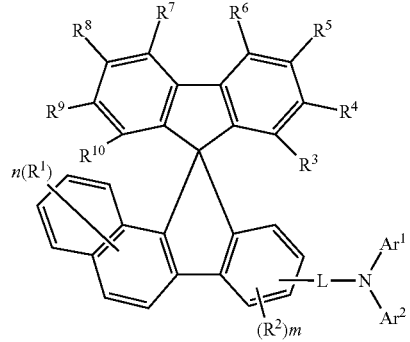

In the Formula (2) to Formula (4), wherein $R^1$, $R^2$, $R^3$, $R^4$, $R^5$, $R^6$, $R^7$, $R^8$, $R^9$, $R^{10}$, L, $Ar^1$, $Ar^2$, n and m are the same as defined in the Formula (1).

In addition, the Formula (1) comprises a compound represented by Formula (5) below.

<Formula (5)>

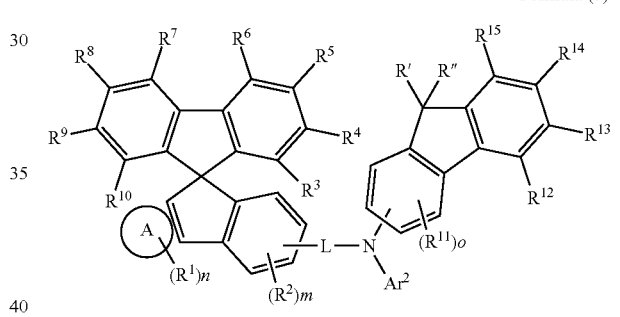

In the Formula (5), wherein $R^1$, $R^2$, $R^3$, $R^4$, $R^5$, $R^6$, $R^7$, $R^8$, $R^9$, $R^{10}$ L, $Ar^2$, n and m are the same as defined in the Formula (1), R', R" may be selected from hydrogen; a $C_6$-$C_{60}$ aryl group; a $C_2$-$C_{60}$ heterocyclic group including at least one hetero atom of O, N, S, Si and P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; or may combine each other and form a spiro, o is an integer of 0 to 3, $R^{11}$, $R^{12}$, $R^{13}$, $R^{14}$ and $R^{15}$ are each independently selected from a hydrogen; a deuterium; a halogen; the group consisting of a $C_6$-$C_{60}$ aryl group; a fluorenyl group; a $C_2$-$C_{60}$ heterocyclic group including at least one hetero atom of O, N, S, Si and P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; and -L'-N($R_a$)($R_b$); or two adjacent $R^{11}$s, $R^{12}$ and $R^{13}$, $R^{13}$ and $R^{14}$, $R^{14}$ and $R^{15}$ may combine to form a aromatic or heterocyclic ring.

Also, the Formula (1) comprises a compound represented by Formula (6) below.

Formula (6)
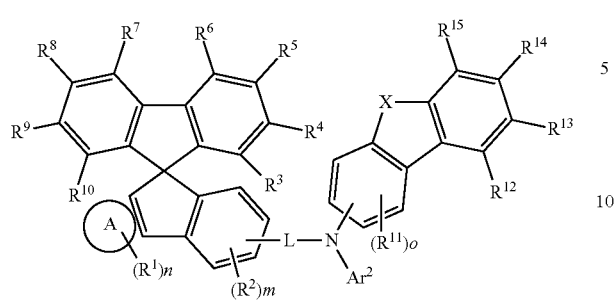
In the Formula (6),
wherein $R^1$, $R^2$, $R^3$, $R^4$, $R^5$, $R^6$, $R^7$, $R^8$, $R^9$, $R^{10}$, L, $Ar^2$, n and m are the same as defined in the Formula (1), and $R^{11}$, $R^{12}$, $R^{13}$, $R^{14}$, $R^{15}$ and o are the same as defined in the Formula (5) and X is O or S.
More specially, the present invention comprises the following compounds.
1-1
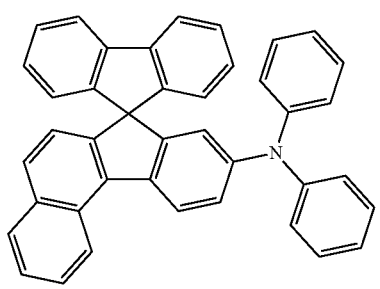
1-2
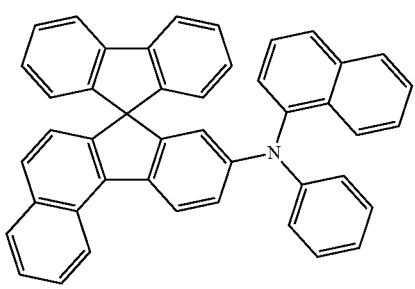
1-3
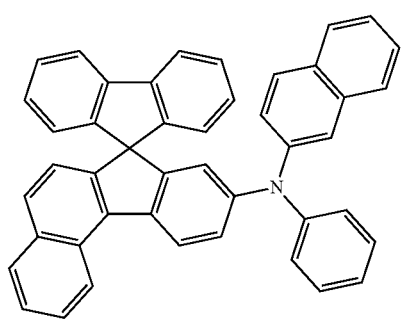
1-4
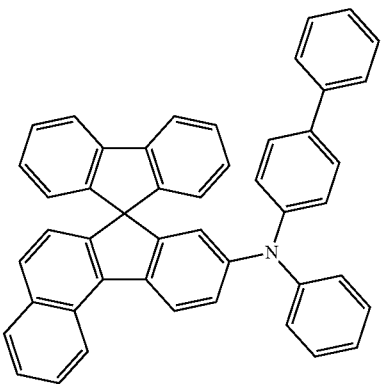
1-5
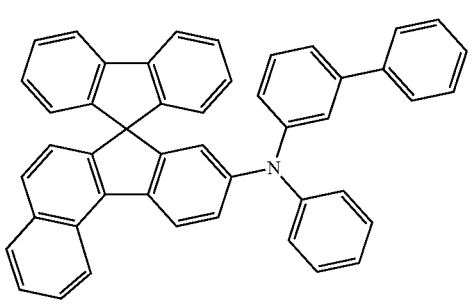
1-6
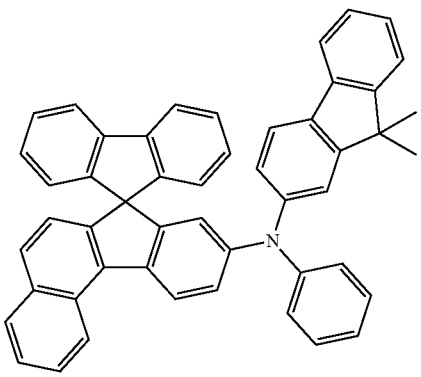
1-7
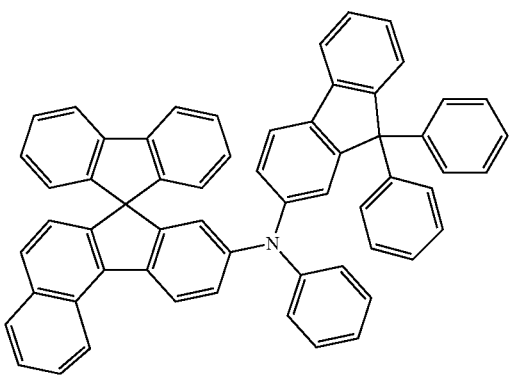

-continued
1-8
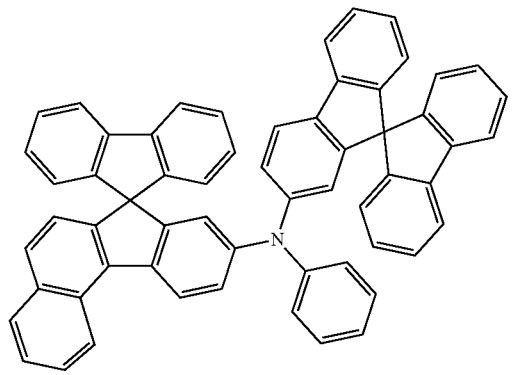
1-9
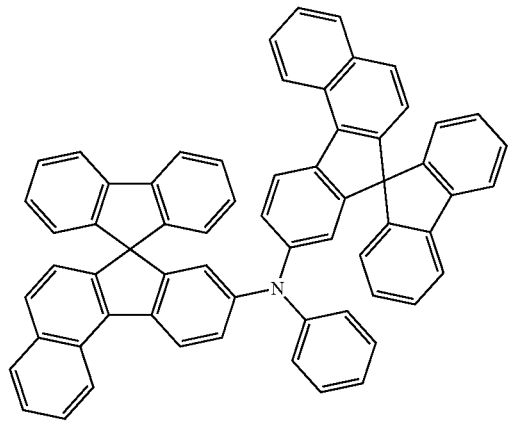
1-10
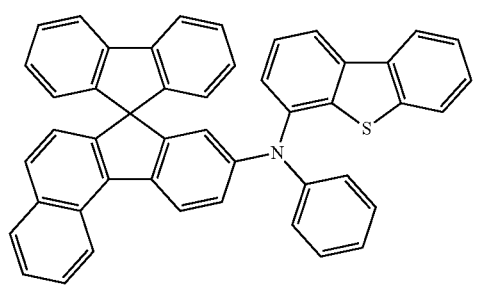
1-11
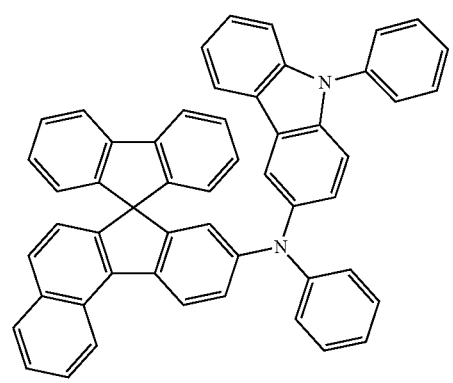
-continued
1-12
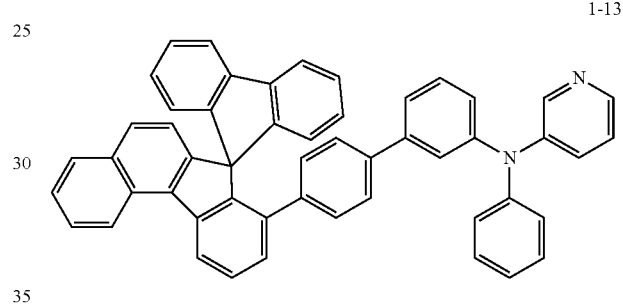
1-13
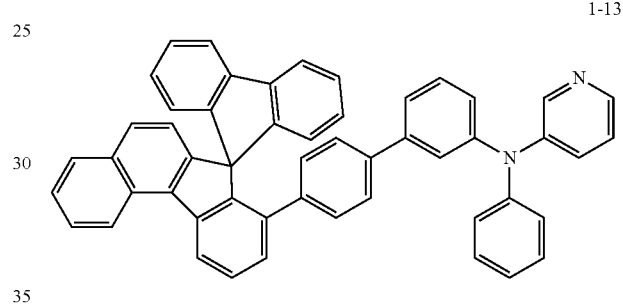
1-14
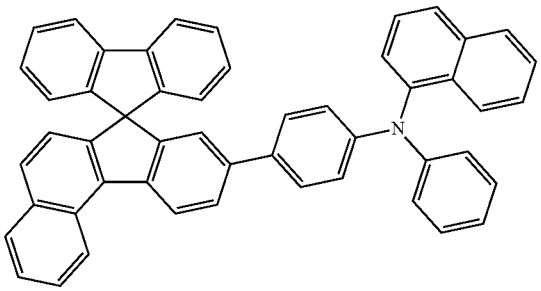
1-15
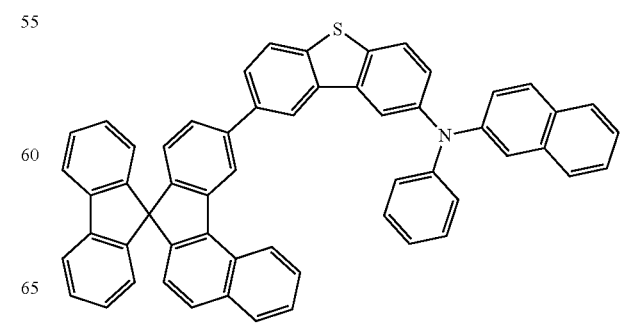

1-16
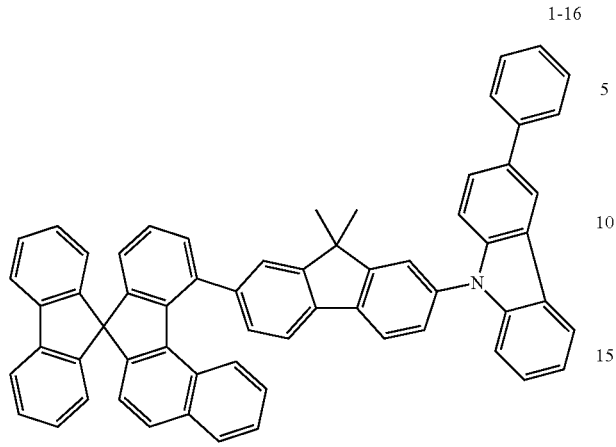
1-17
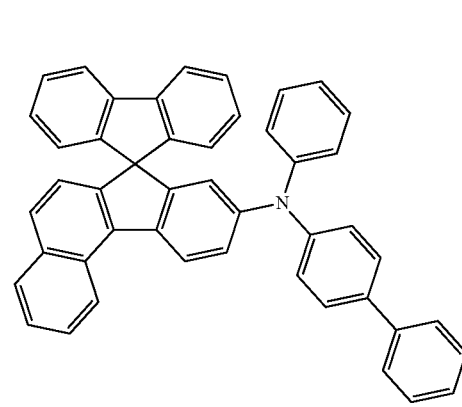
1-18
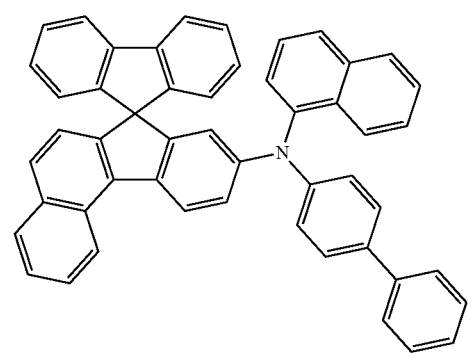
1-19
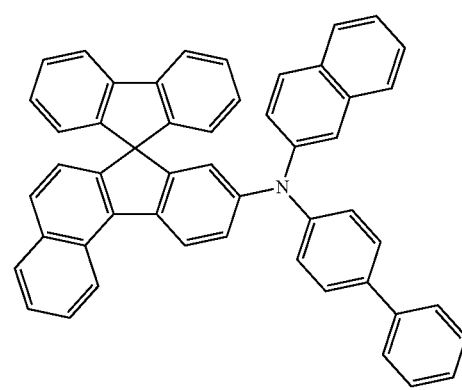
1-20
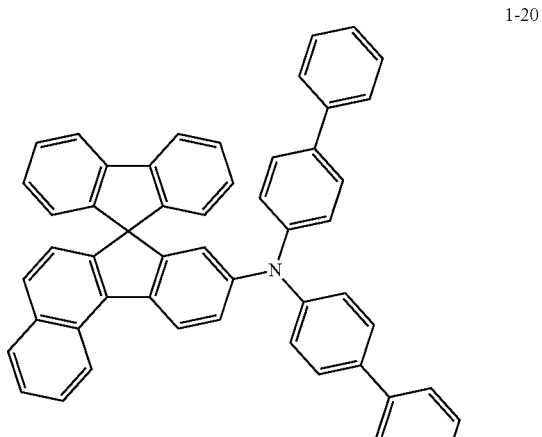
1-21
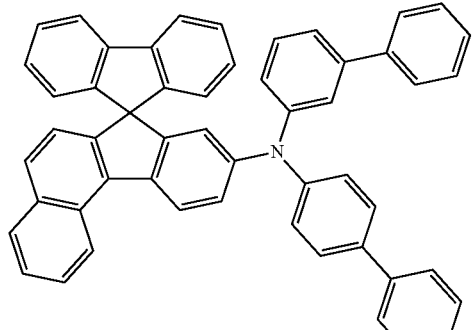
1-22
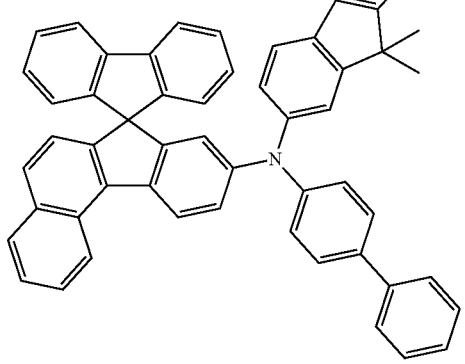
1-23
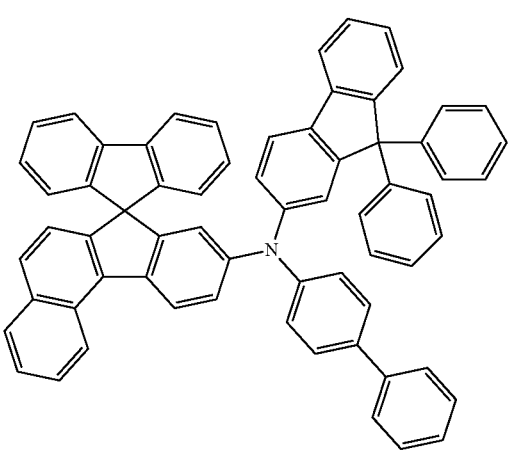

1-24
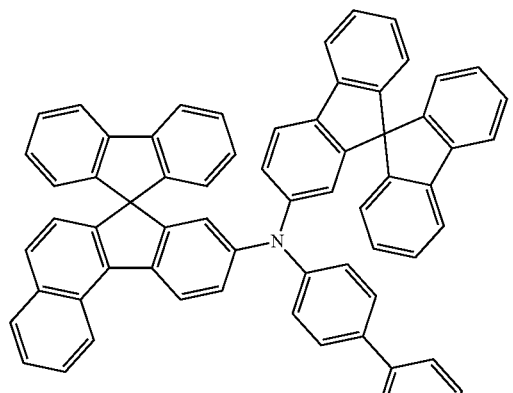
1-25
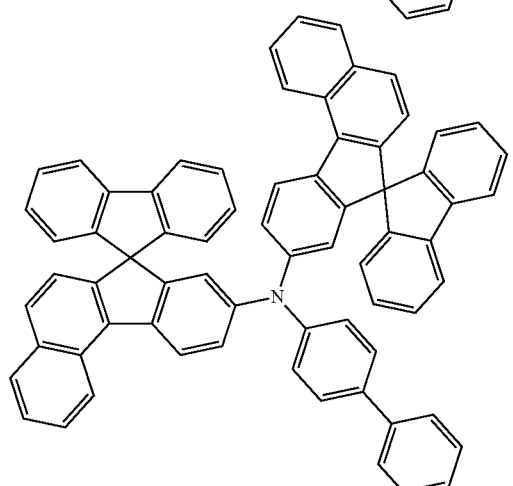
1-26
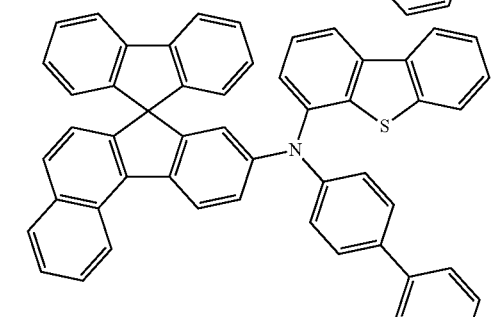
1-27
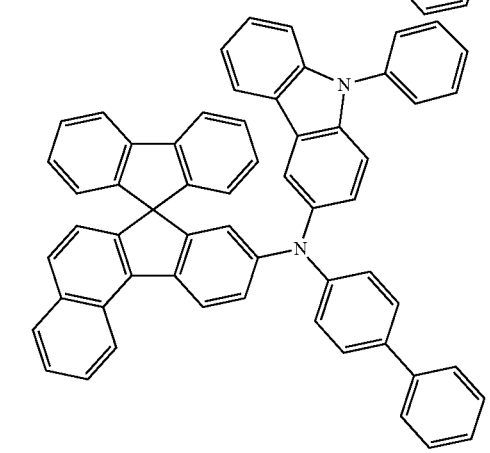
1-28
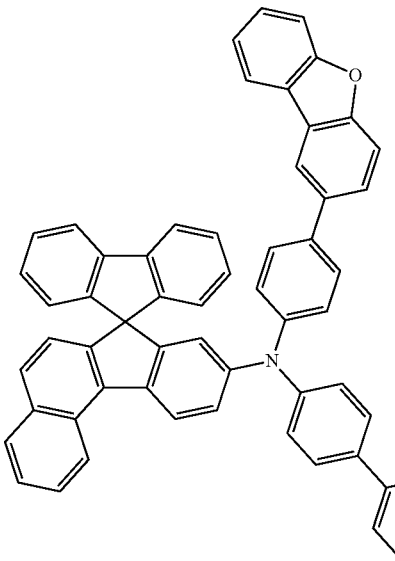
1-29
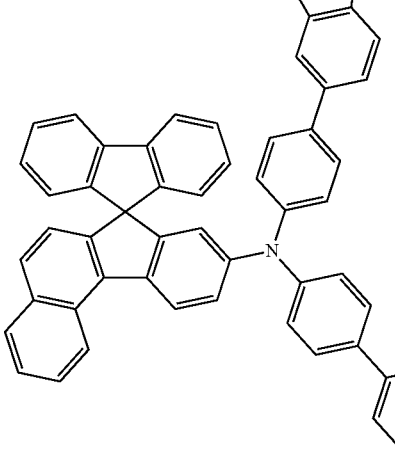
1-30
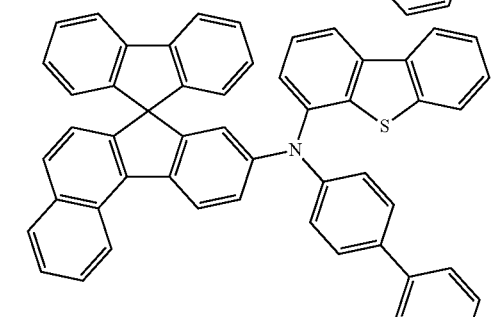
1-31
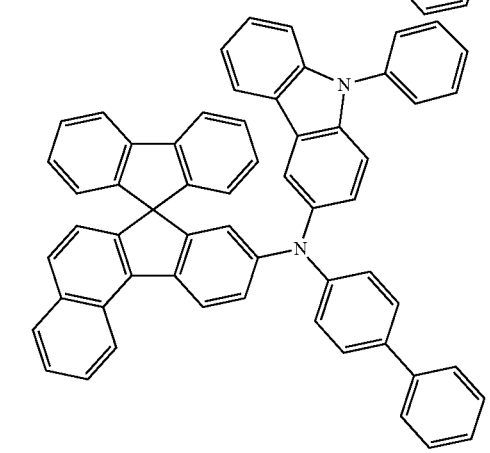

1-32
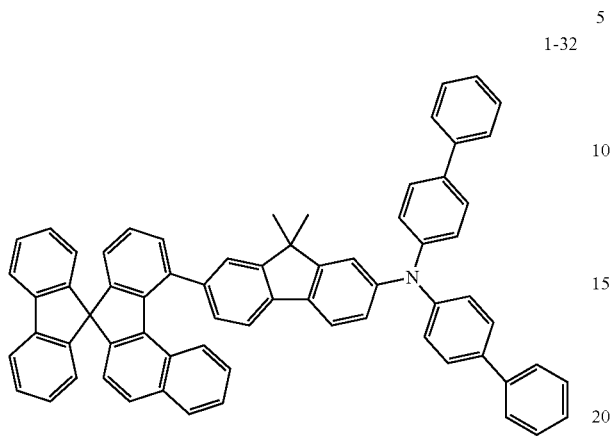
1-35
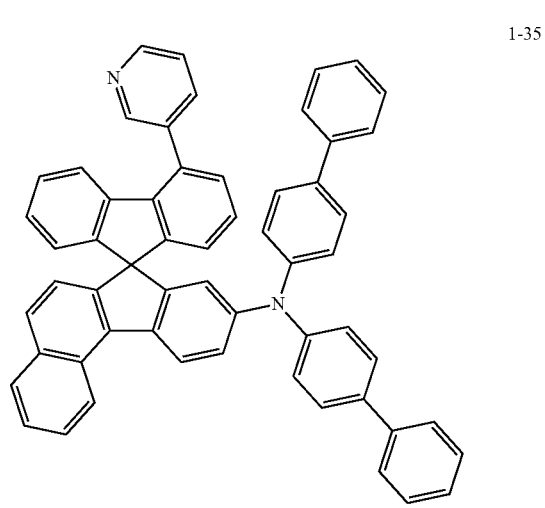
1-33
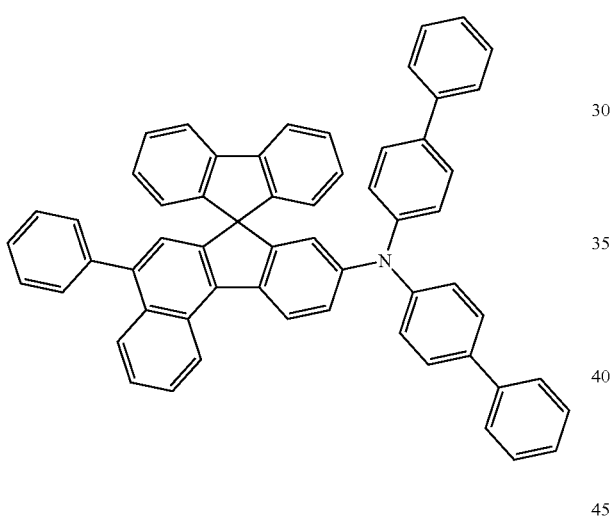
1-36
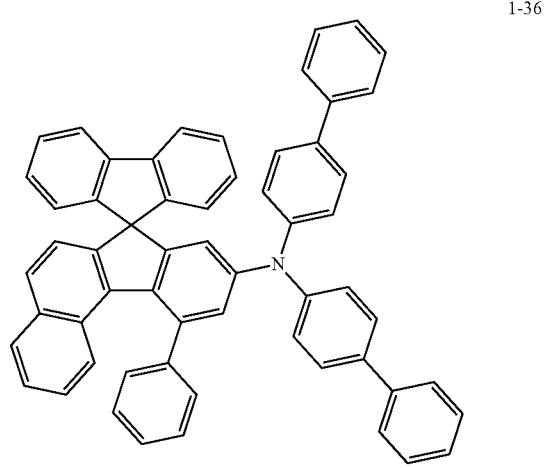
1-34
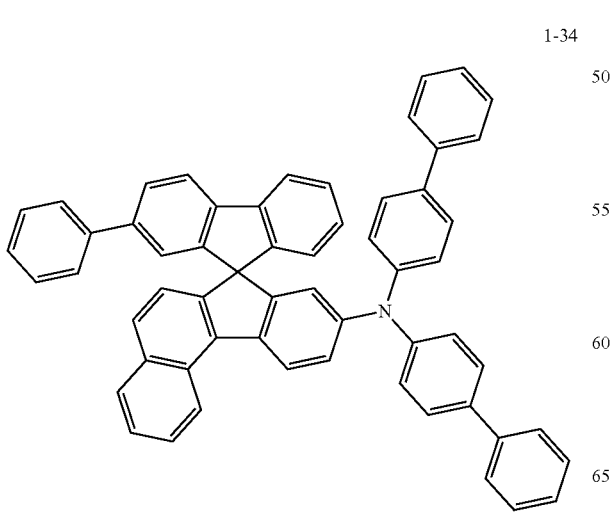
1-37
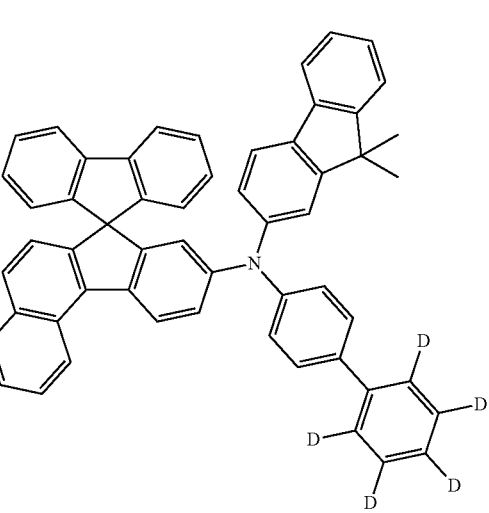

1-38
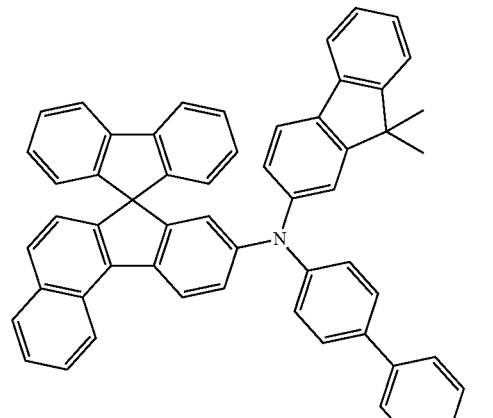
1-39
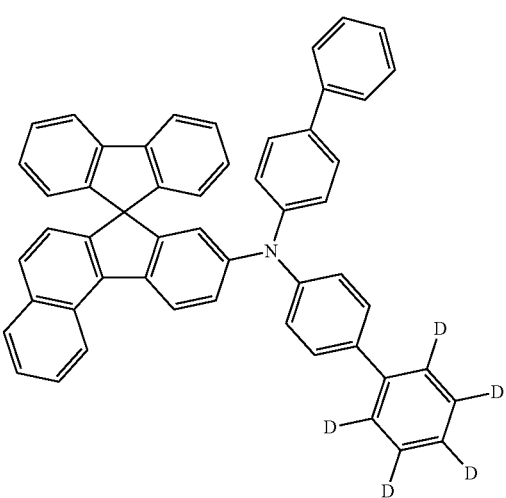
1-40
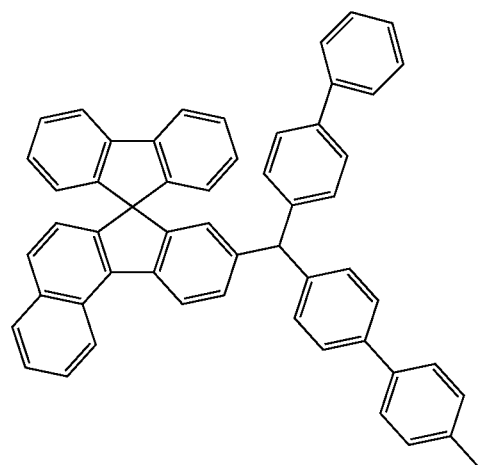
2-1
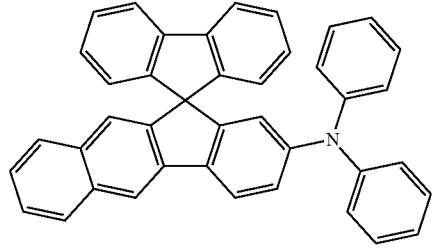
2-2
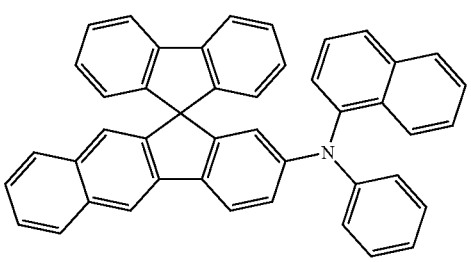
2-3
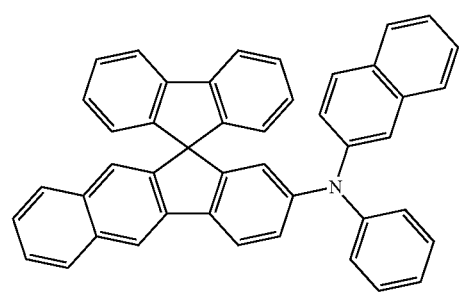
2-4
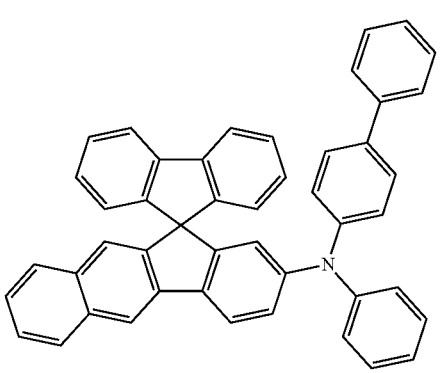
2-5
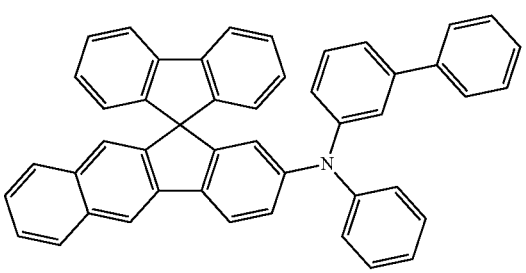

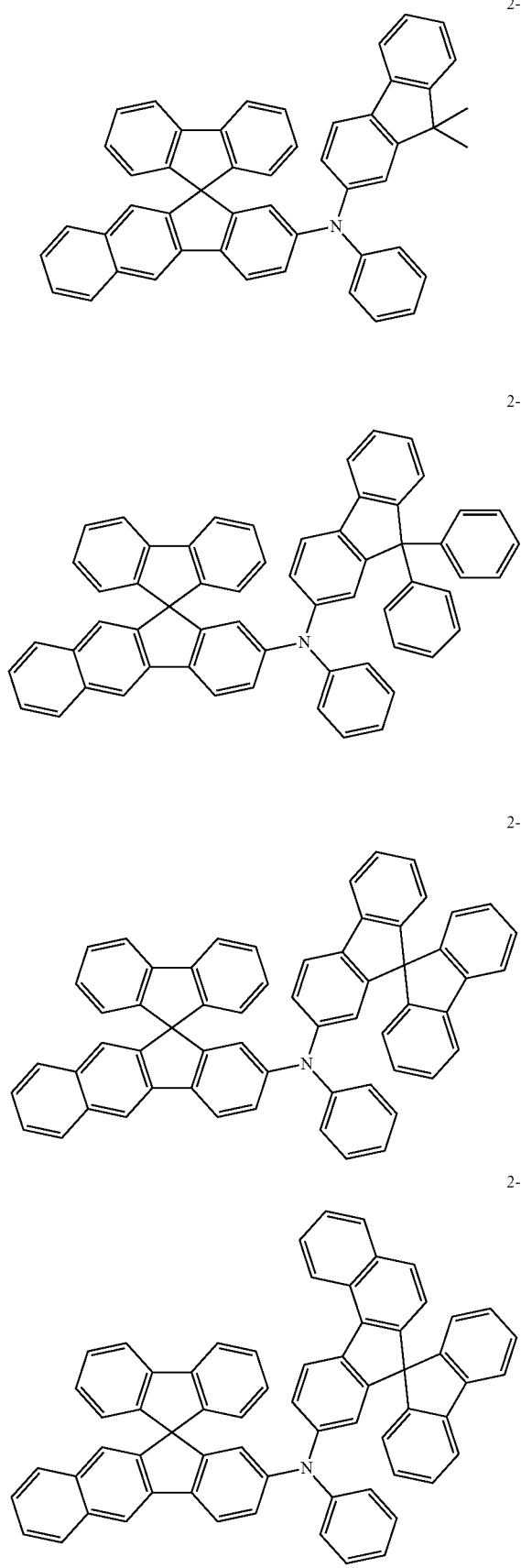
2-6
2-7
2-8
2-9
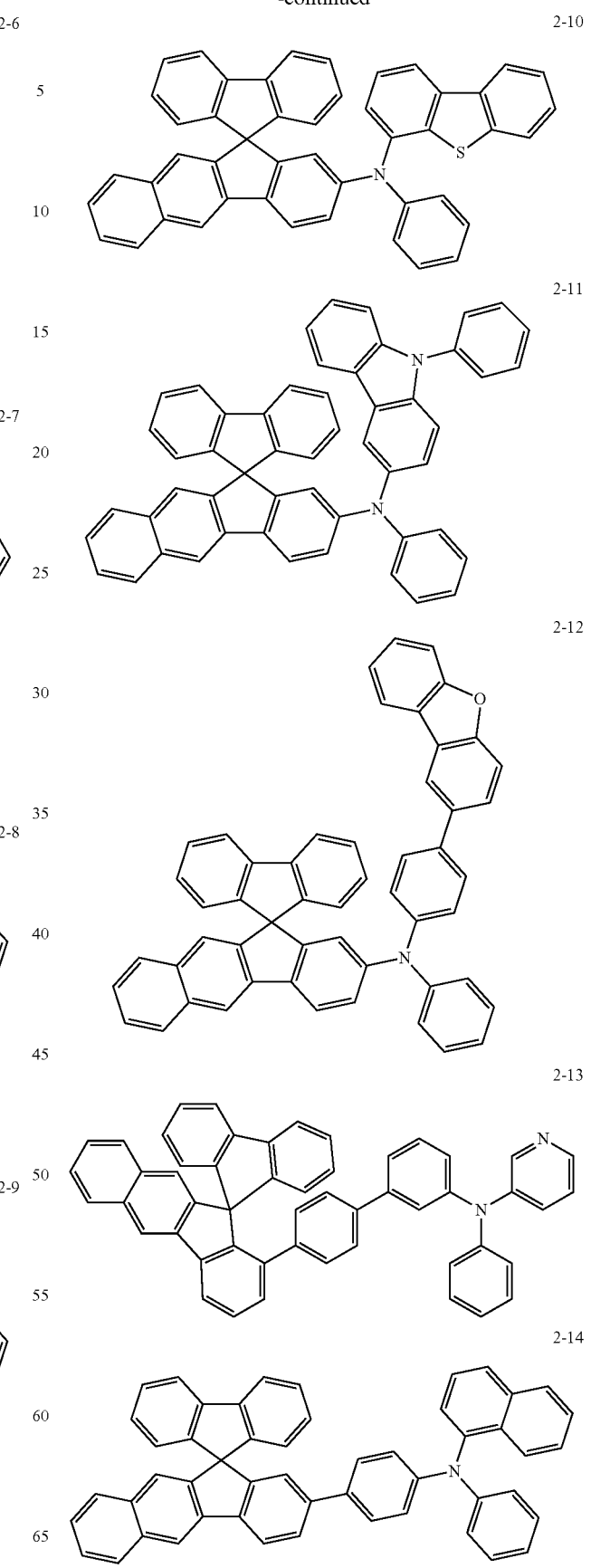
2-10
2-11
2-12
2-13
2-14

2-15
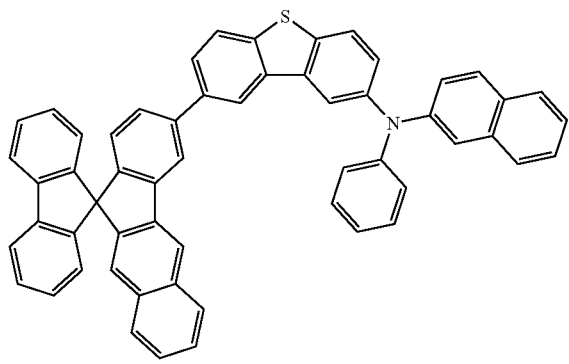
2-16
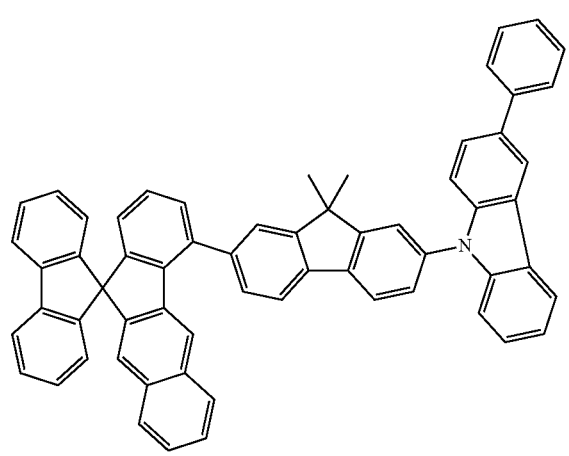
2-17
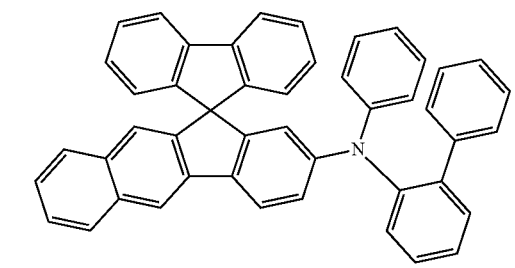
2-18
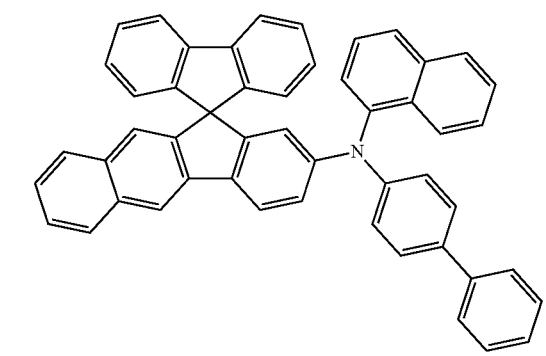
2-19
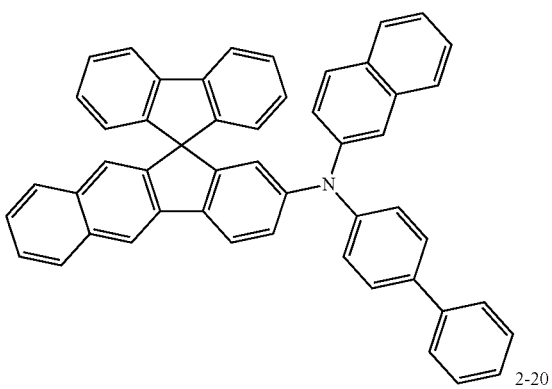
2-20
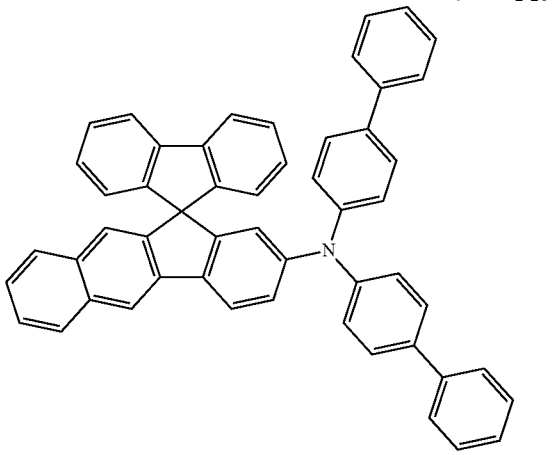
2-21
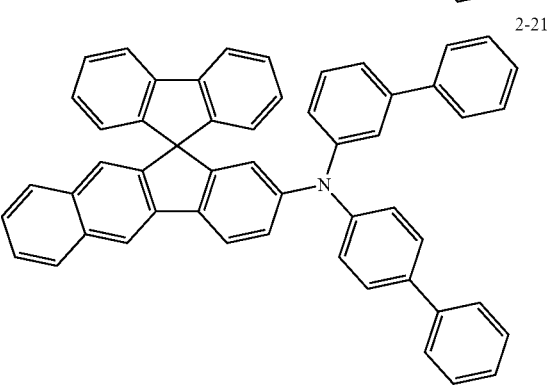
2-22
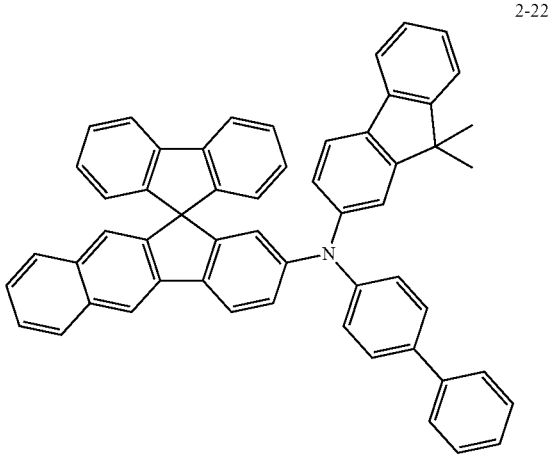

2-23
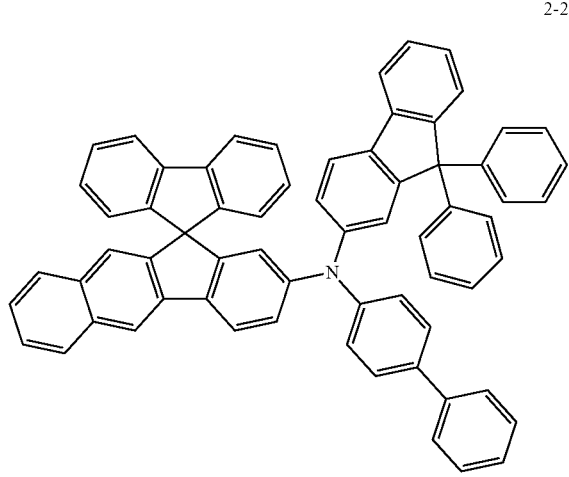
2-26
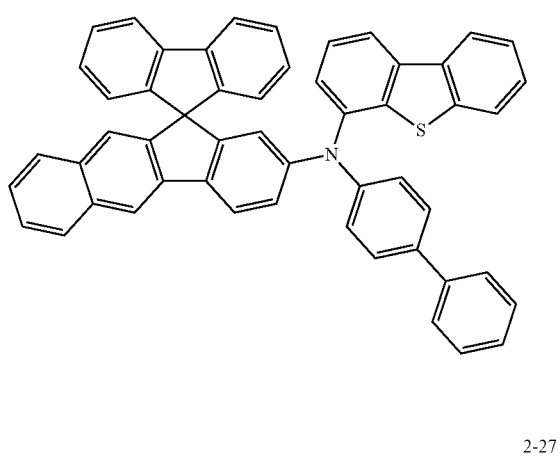
2-24
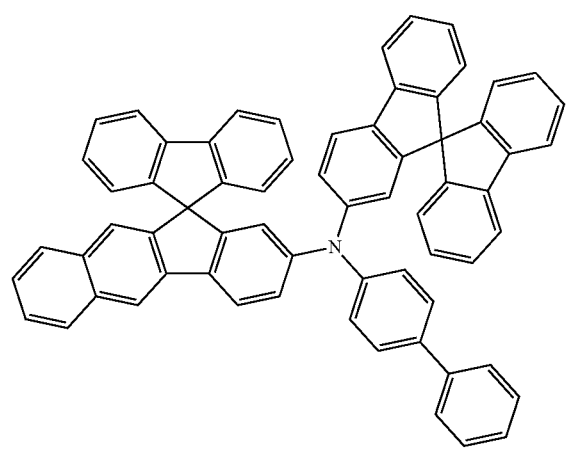
2-27
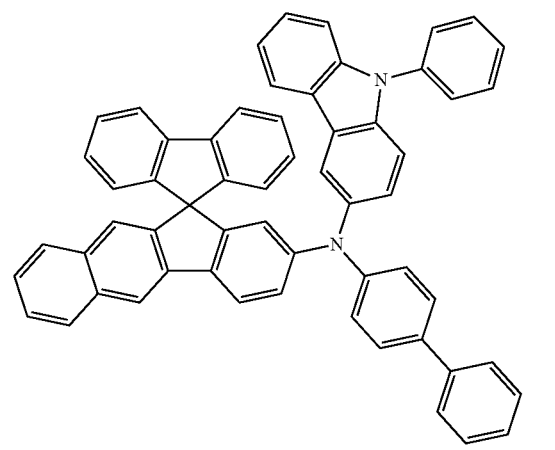
2-25
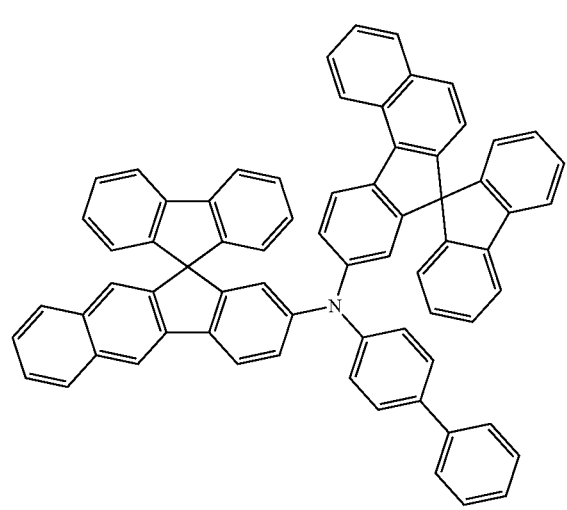
2-28
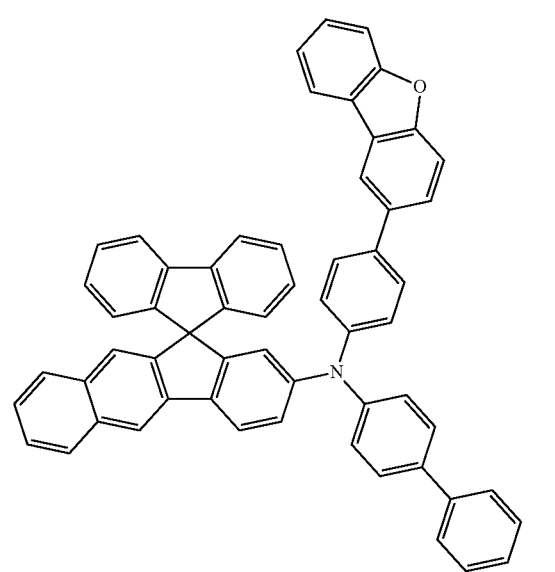

2-29
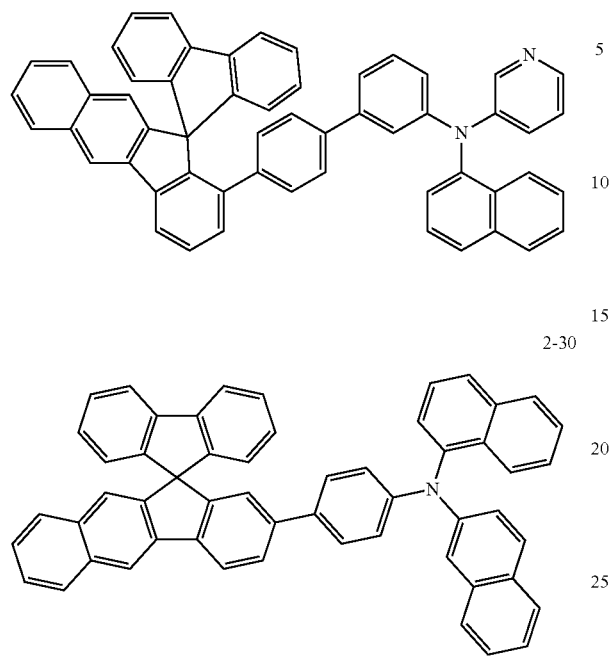
2-30
2-31
2-32
2-33
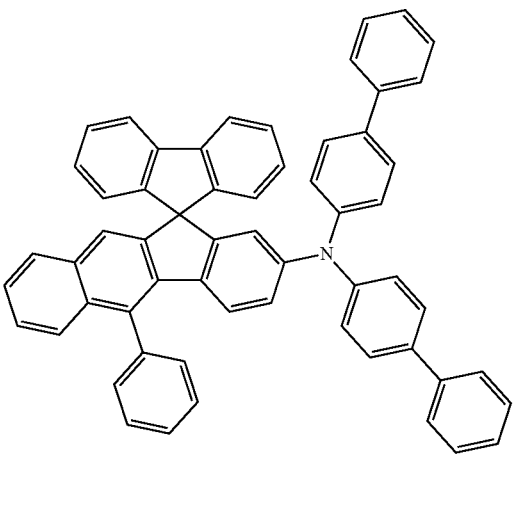
2-34
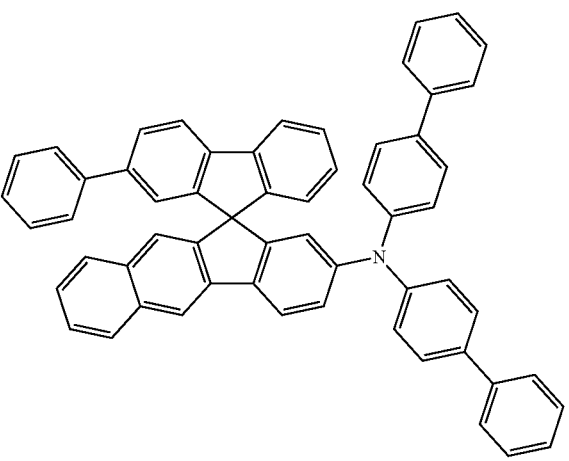
2-35
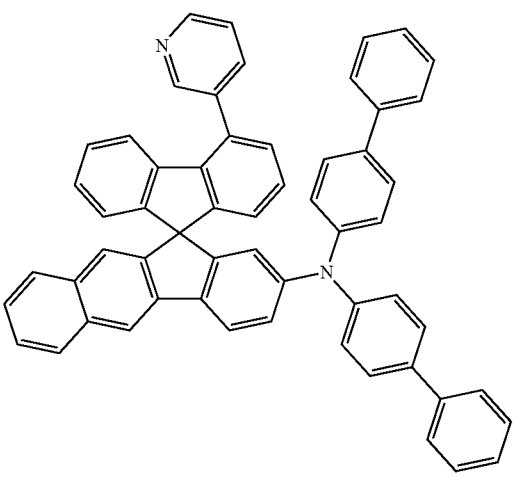

2-36
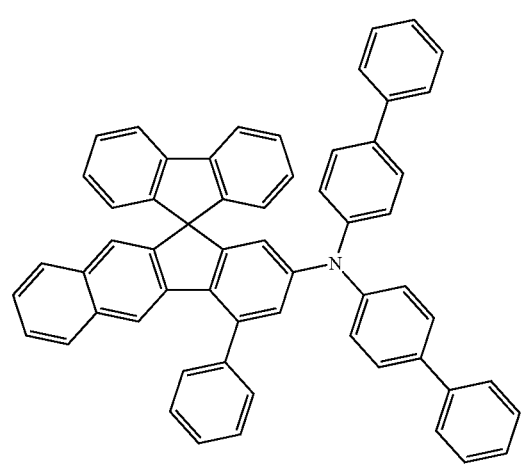
2-39
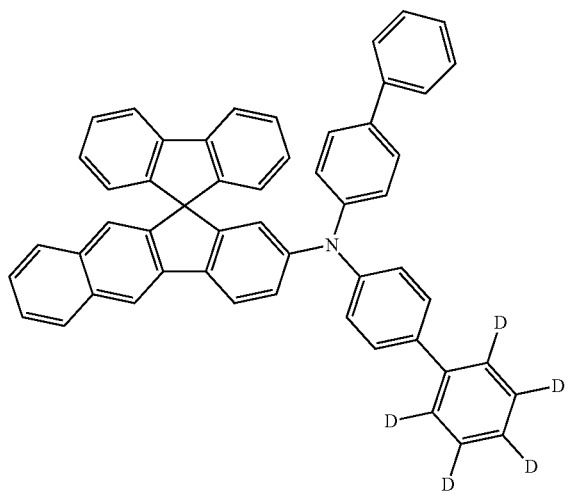
2-37
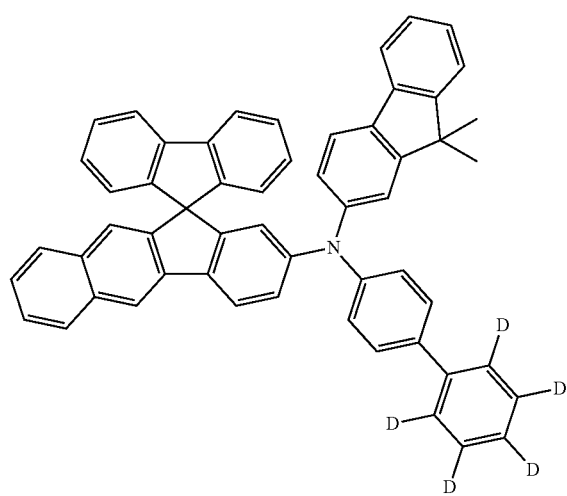
2-40
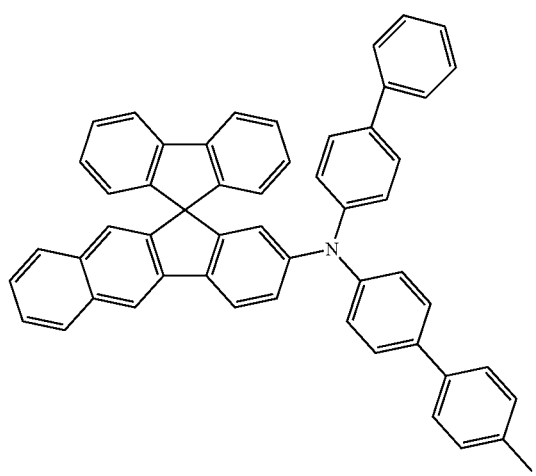
2-38
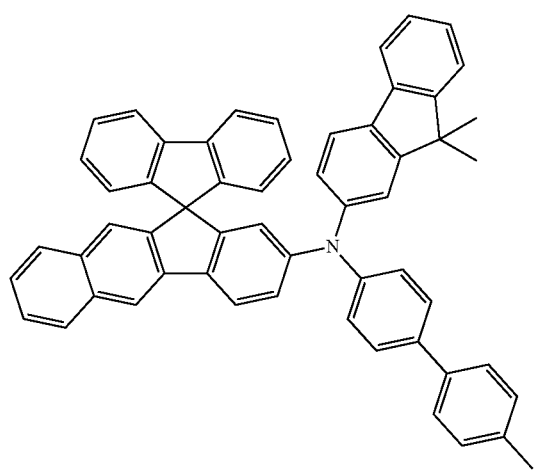
3-1
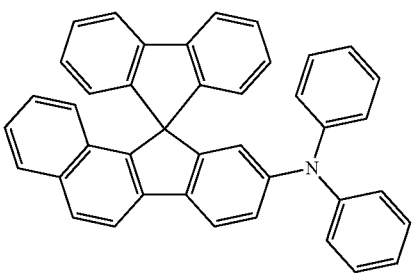
3-2
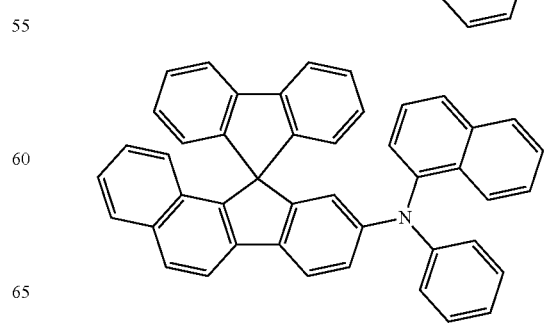

-continued
3-3
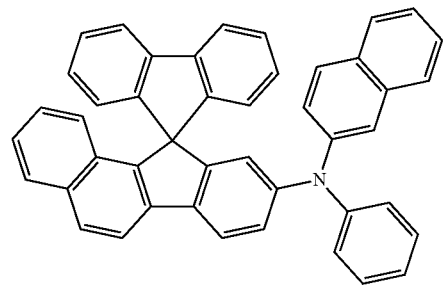
3-4
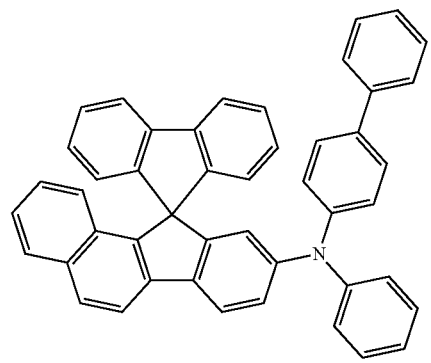
3-5
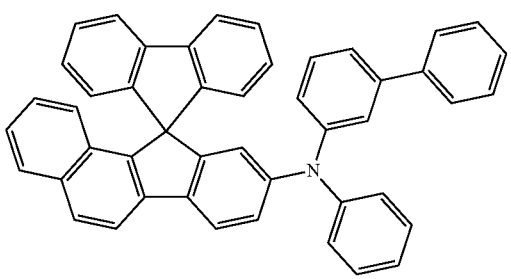
3-6
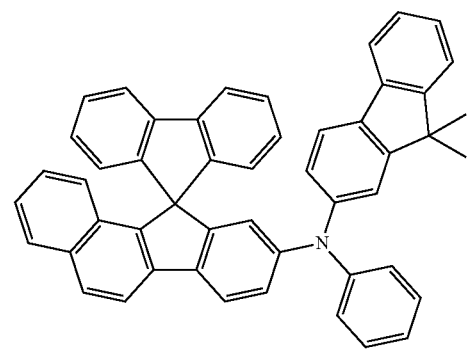
3-7
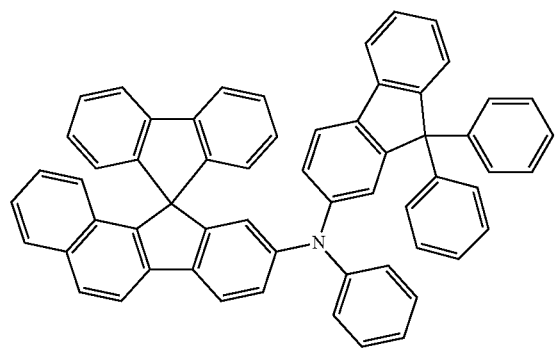
3-8
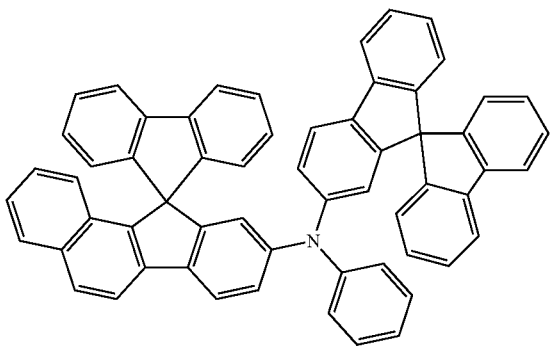
3-9
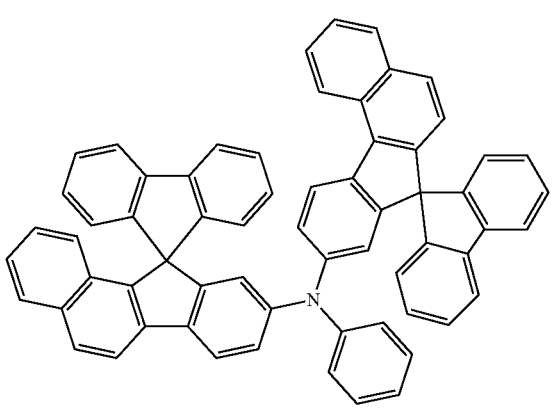
3-10
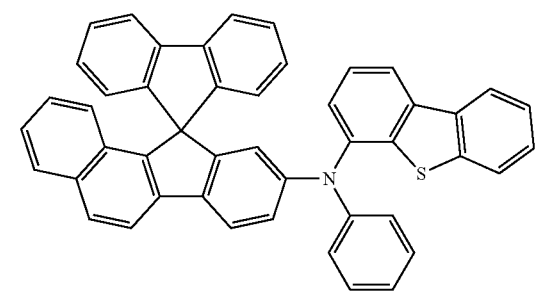
3-11
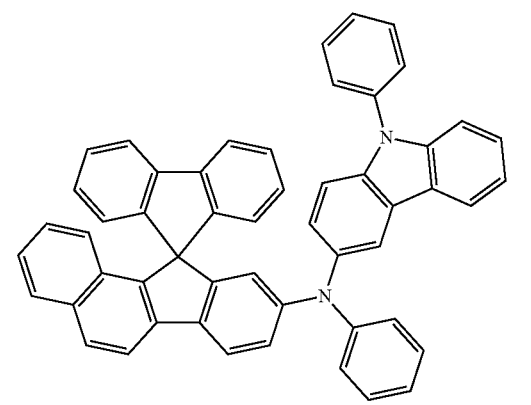

3-12
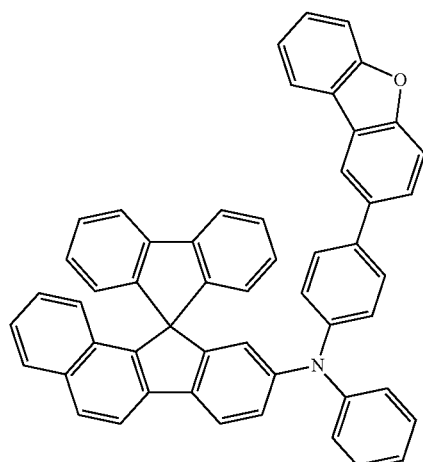
3-16
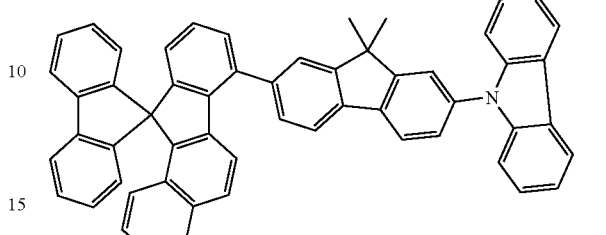
3-13
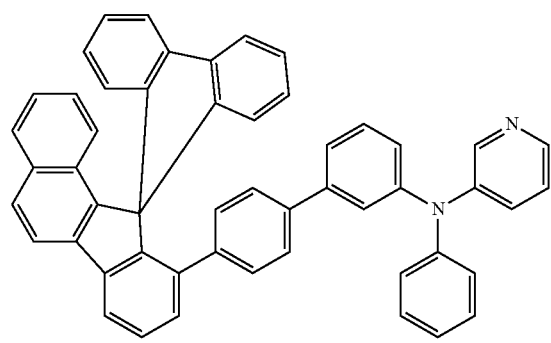
3-17
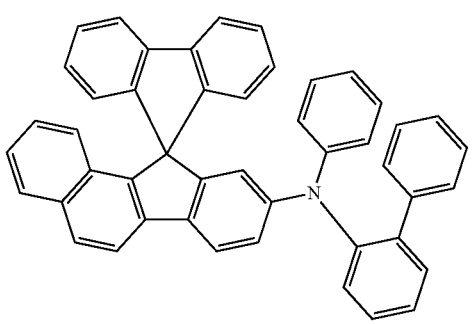
3-14
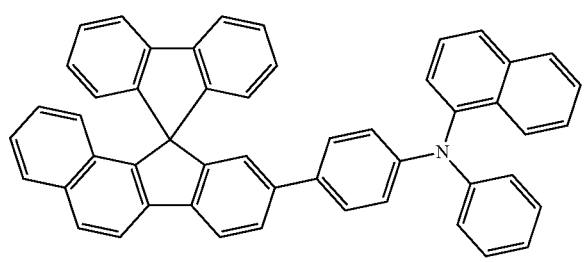
3-18
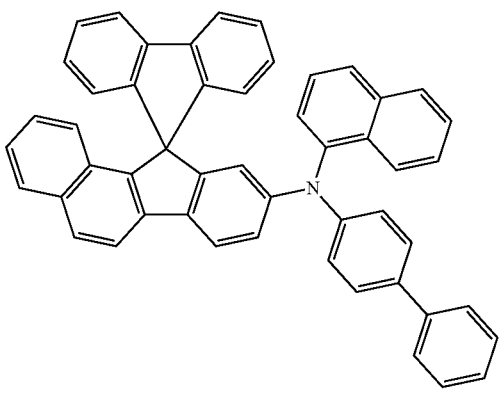
3-15
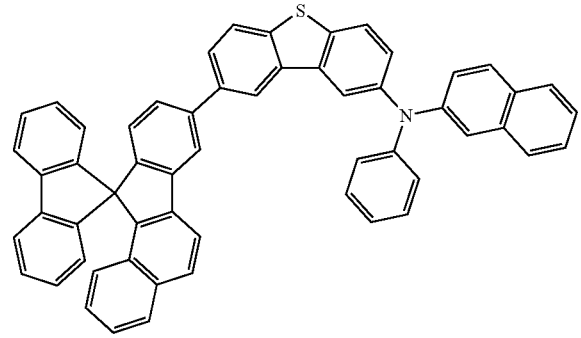
3-19
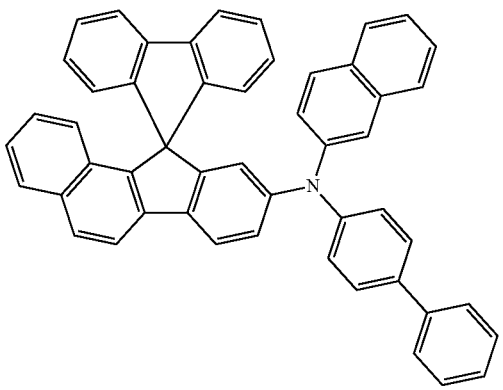

3-20
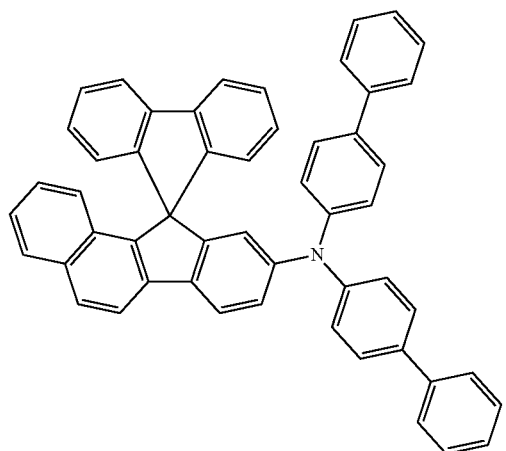
3-21
3-22
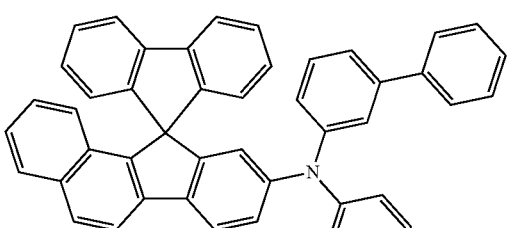
3-23
3-24
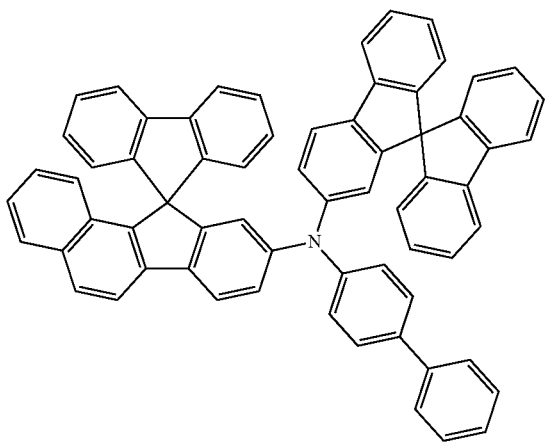
3-25
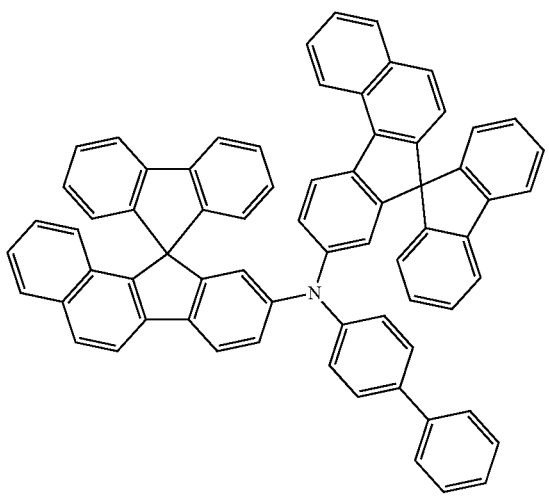
3-26
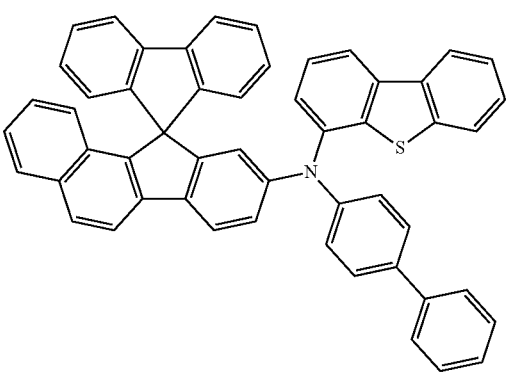

-continued
3-27
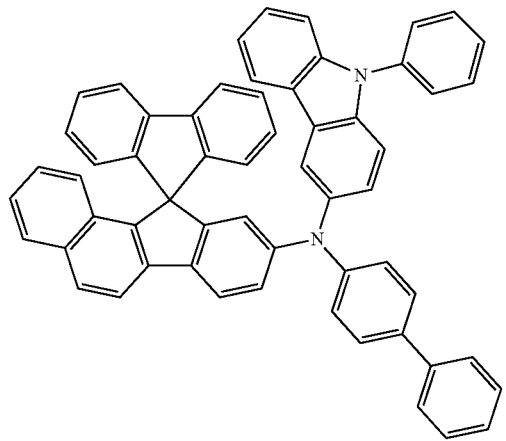
3-28
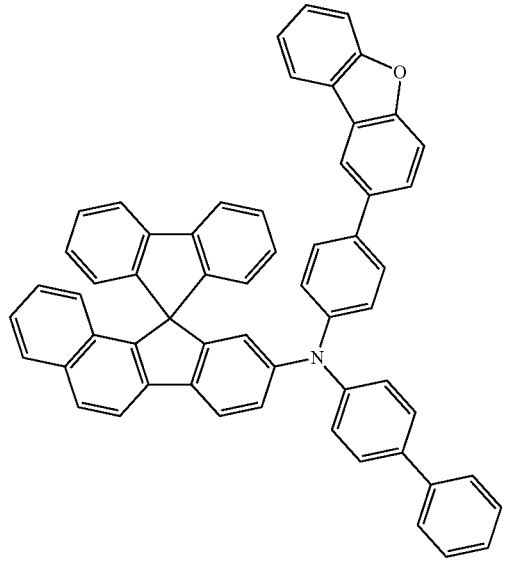
3-29
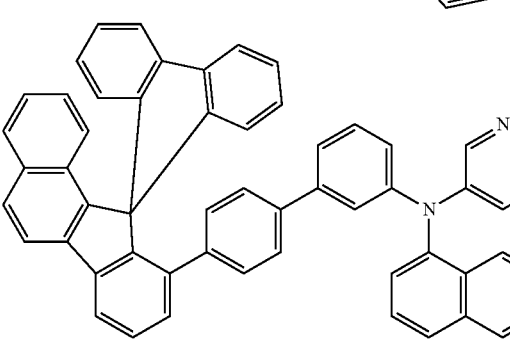
3-30
-continued
3-31
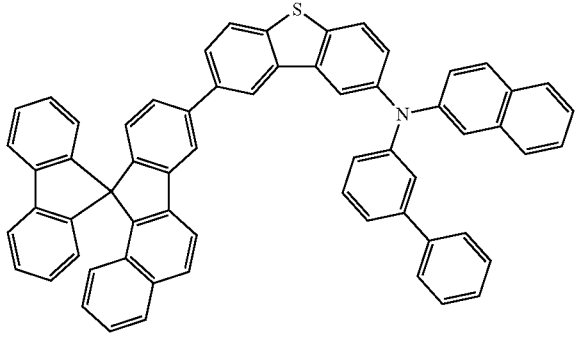
3-32
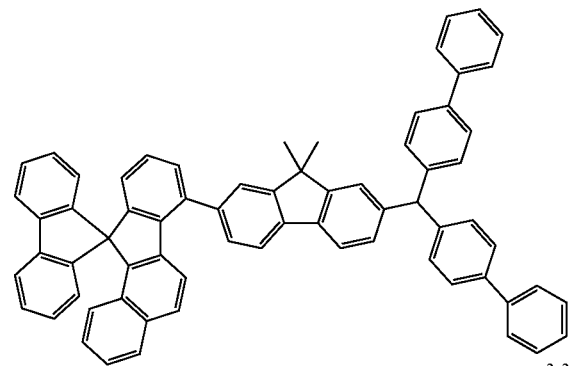
3-33
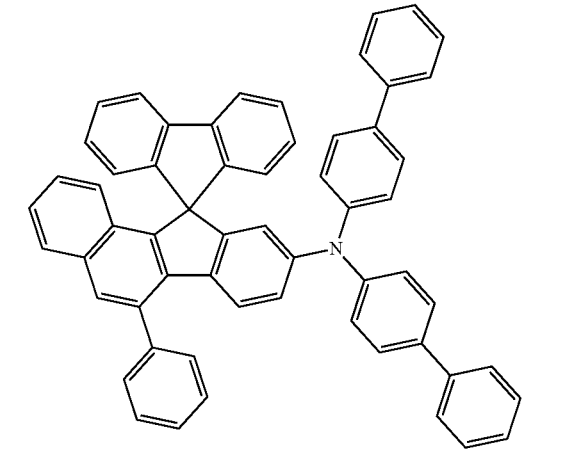
3-34
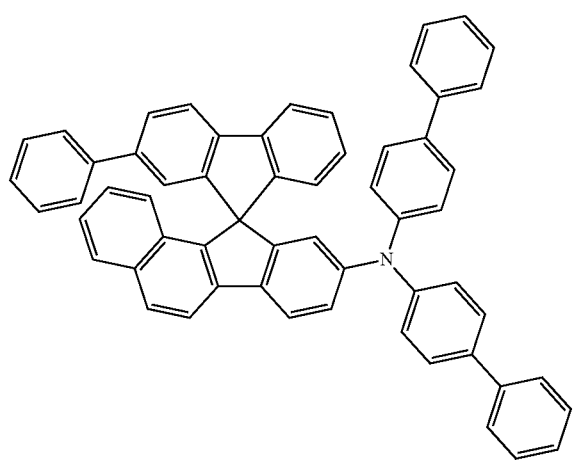

3-35
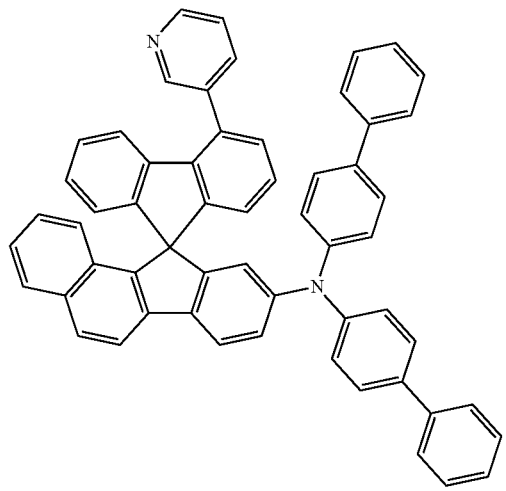

3-36
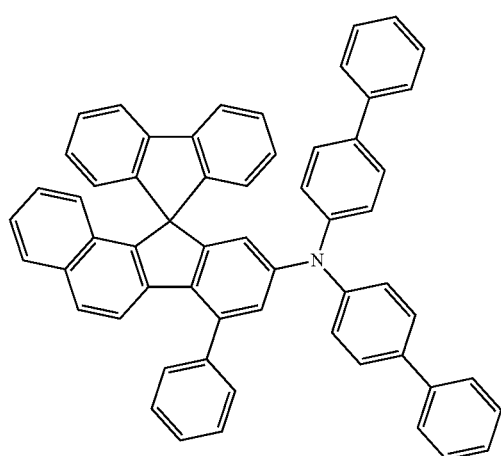

3-37
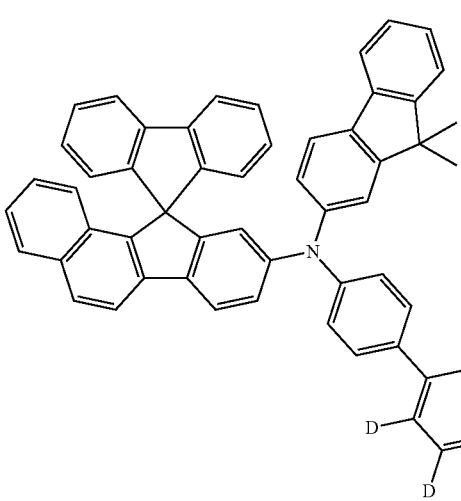

3-38
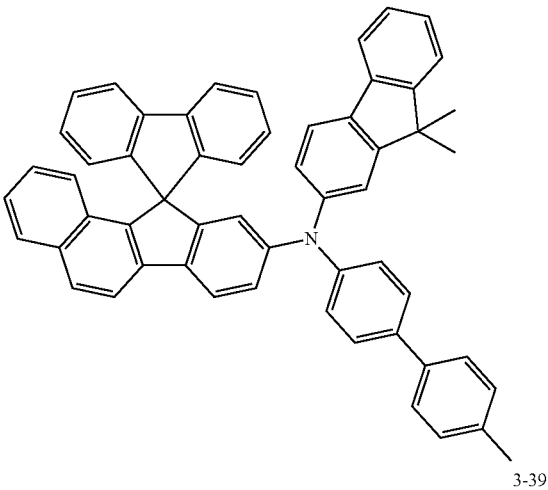

3-39
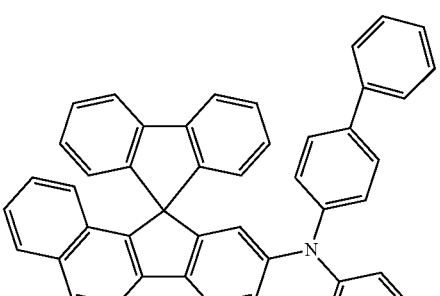

3-40
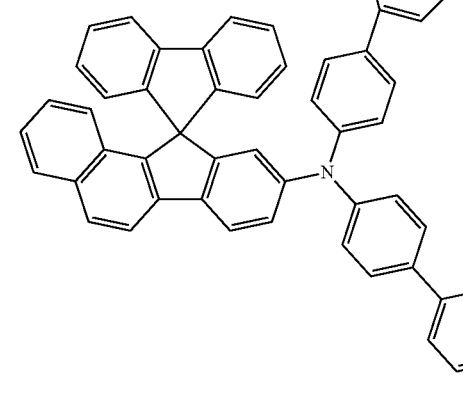

Referring to the FIGURE, the organic electric element (100) according to the present invention includes a first electrode (120) formed on a substrate (110), a second electrode (180), and an organic material layer between the first electrode (120) and the second electrode (180), which contains the compound represented by Formula 1. Here, the first electrode (120) may be an anode (positive electrode), and the second electrode (180) may be a cathode (negative electrode). In the case of an inverted organic electric element, the first electrode may be a cathode, and the second electrode may be an anode.

The organic material layer may include a hole injection layer (130), a hole transport layer (140), an emitting layer (150), an electron transport layer (160), and an electron injection layer (170) formed in sequence on the first electrode (120). Here, the remaining layers except the emitting layer (150) may not be formed. The organic material layer may further include a hole blocking layer, an electron blocking layer, an emitting-auxiliary layer (151), a buffer layer (141), etc., and the electron transport layer (160) and the like may serve as a hole blocking layer.

Although not shown, the organic electric element according to the present invention may further include a protective layer formed on at least one side of the first and second electrodes, which is a side opposite to the organic material layer.

On the other hand, even if the same core is used, the band gap, the electrical characteristics, the interface characteristics, and the like may vary depending on which substituent is bonded at which position, therefore the choice of core and the combination of sub-substituents associated therewith is also very important, and in particular, when the optimal combination of energy levels and T1 values and mobility (interfacial characteristics) of each organic material layer is achieved, a long life span and high efficiency can be achieved at the same time.

Recently, as described above, in order to solve the emission problem with a hole transport layer of an organic electric element, an emitting-auxiliary layer is preferable formed between the hole transport layer and an emitting layer, and it is time to develop different emitting-auxiliary layers according to respective emitting layers (R, G, B). Meanwhile, in the case of the emitting-auxiliary layer, mutual relationship between hole transport layer and emitting layer (host) should be figured out. Even if similar cores are used, it will be very difficult to deduce the characteristics if the organic material layer used is different.

Therefore, in the present invention, by using the compound represented by the Formula (1) as the hole transport material and/or light-emitting auxiliary layer material, the energy levels (level) and T1 value among each of organic material layer are optimized to improve the life span and efficiency of the organic electric element at the same time.

The organic electric element according to an embodiment of the present invention may be manufactured using a PVD (physical vapor deposition) method. For example, the organic electric element may be manufactured by depositing a metal or a conductive metal oxide or a mixture thereof on the substrate (110) to form the anode (120), forming the organic material layer including the hole injection layer (130), the hole transport layer (140), the emitting layer (150), the electron transport layer (160), and the electron injection layer (170) thereon, and then depositing a material, which can be used as the cathode (180), thereon.

Accordingly, the present invention provides the organic electric element characterized in that can comprise a first electrode; a second electrode; and an organic material layer disposed between the first electrode and the second electrode. The organic material layer can comprise the compound represented by Formula (1).

In addition, the present invention may further include a light efficiency enhancing layer formed on at least one of the opposite side to the organic material layer among one side of the first electrode, or one of the opposite side to the organic material layer among one side of the second electrode.

Also, the present invention provides the organic electric element characterized in that the organic material layer is formed by one of a spin coating process, a nozzle printing process, an inkjet printing process, a slot coating process, a dip coating process or a roll-to-roll process, and comprises the compounds above as a electron transport material.

In another specific examples of the invention, the present invention provides the organic electric element characterized in that the mixture of the same or different kinds of compounds represented Formula (1) is used in the organic material layer The present invention also provides an electronic device including a display device including the organic electric element; and a control part driving the display apparatus.

According to another aspect, the present invention provides an electronic device characterized in that the organic electric element is at least one of an OLED, an organic solar cell, an organic photo conductor, an organic transistor and an element for monochromic or white illumination. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, Synthesis Examples of the compound represented by Formula (1) according to the present invention and preparation examples of the organic electric element will be described in detail by way of example, but are not limited to the following examples of the invention.

Synthesis Example

The final product represented by Formula (1) according to the present invention can be synthesized by reaction between Sub 1 and Sub 2 as illustrated in the following Reaction Scheme 1.

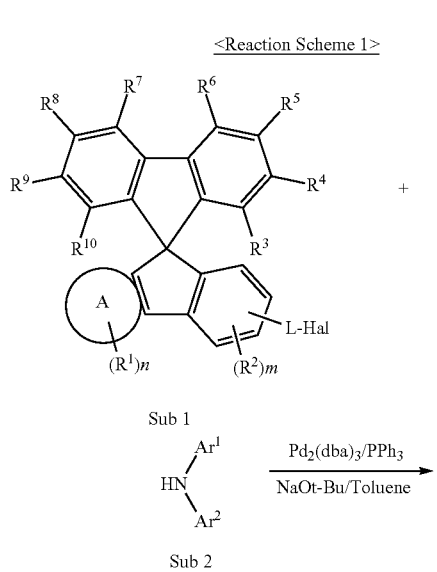

-continued
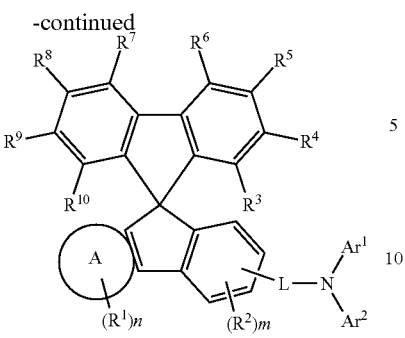
Final Products
*Hal = halogen (F, Cl, Br, I)
Synthesis Examples of Sub 1
Sub 1 of Reaction Scheme 1 can be synthesized according to, but is not limited thereto, the reaction path of the following Reaction Scheme 2.
<Reaction Scheme 2> L is not selected from a group consisting of a single bond.
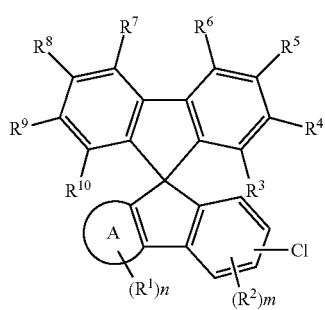
Sub 1-1
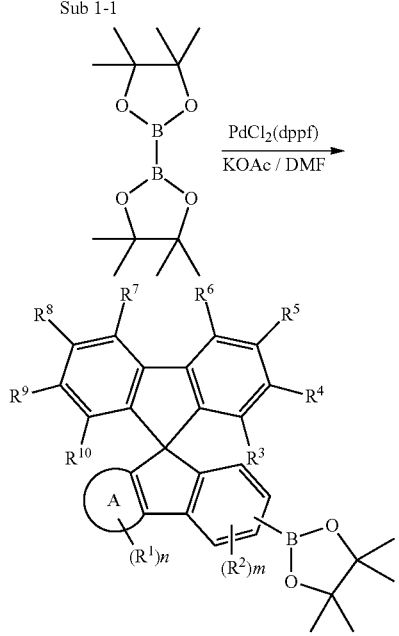
Sub 1-2
-continued
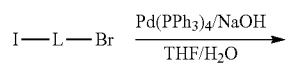
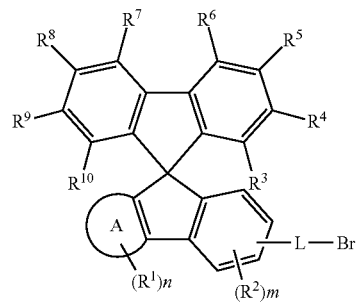
Sub 1
Synthesis Examples of Sub 1-1
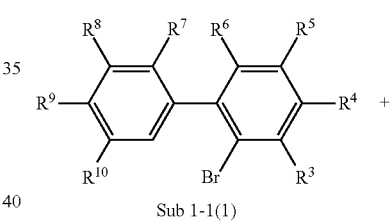
Sub 1-1(1)
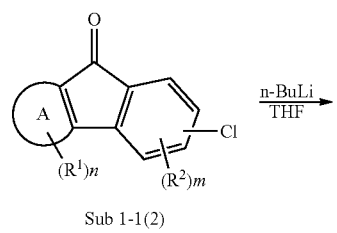
Sub 1-1(2)
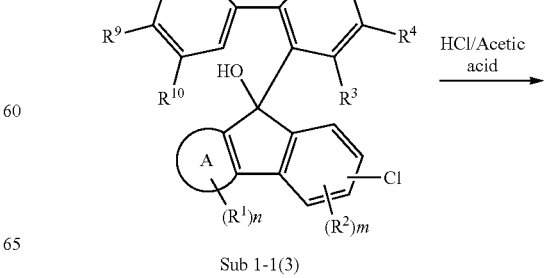
Sub 1-1(3)

45

-continued

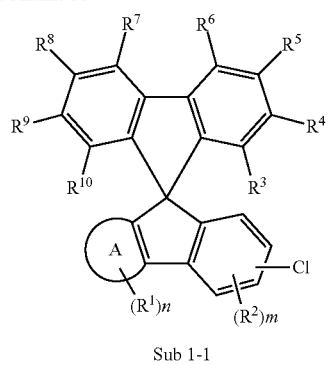

Sub 1-1

1) Synthesis of Sub 1-1-1

46

After Sub 1-1 (1)-1 (46.6 g, 200 mmol) and Sub 1-1 (2)-1 (52.9 g, 200 mmol) were dissolved in THF, the temperature of the reactant product was lowered to −78° C., n-BuLi (2.5 M in hexane) was slowly added dropwise, and the reaction was stirred at room temperature for 4 hours. When the reaction is complete, the reaction product was quenched by adding in $H_2O$, and the water in the reaction product was removed. After the filtration under reduced pressure, the organic solvent was concentrated and the resulting product was separated by column chromatography to obtain 74.6 g of 1-1 (3)-1 (yield: 89%). Thereafter, HCl and acetic acid are added to Sub 1-1 (3)-1 (74.6 g, 178 mmol), and the mixture is stirred at 80° C. for 1 hour. When the reaction was completed, the reaction mixture was filtered under reduced pressure, the organic solvent was concentrated, and the resulting product was separated by column chromatography to obtain 64.9 g of Sub 1-1-1. (yield: 91%).

2) Synthesis of Sub 1-1-2

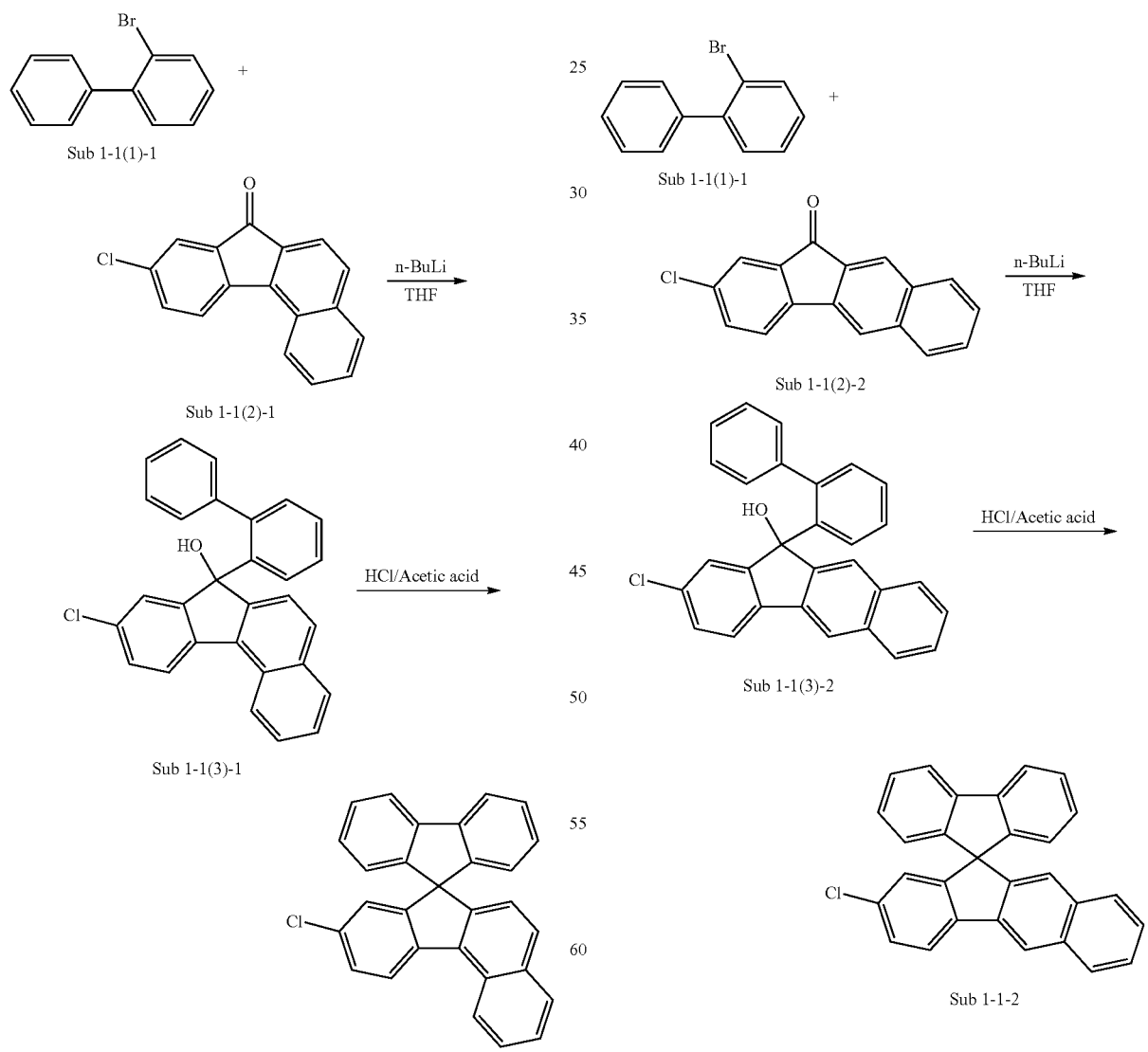

The same procedure as described in the synthesis method of Sub 1-1-1 was carried out to obtain 64.9 g of Sub 1-1-2. (yield: 90%)

3) Synthesis of Sub 1-1-3
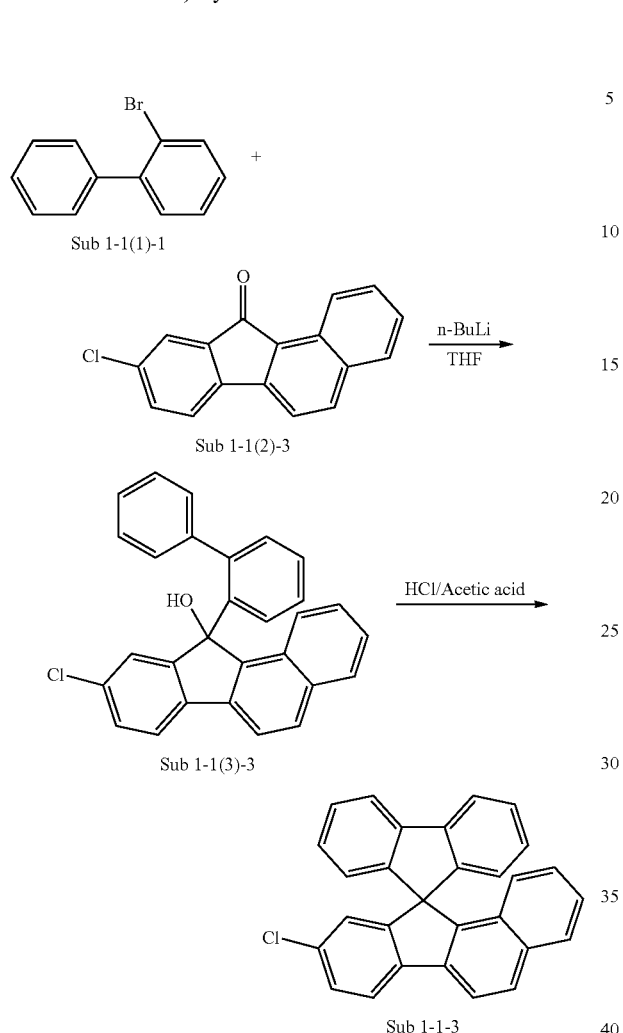
Sub 1-1-3
The same procedure as described in the synthesis method of Sub 1-1-1 was carried out to obtain 63.5 g of Sub 1-1-3 (yield: 89%).
[Reference: synthesis of Sub 1-1 (2)]
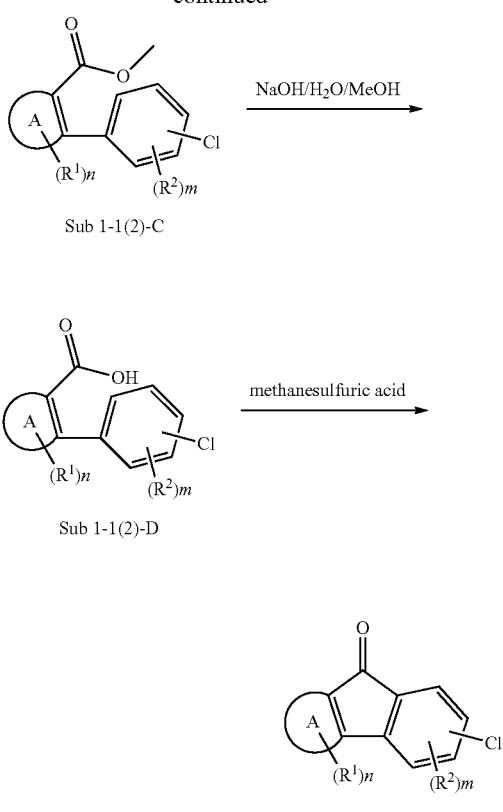
Synthesis Examples of Sub 1-2
1) Synthesis of Sub 1-2-1
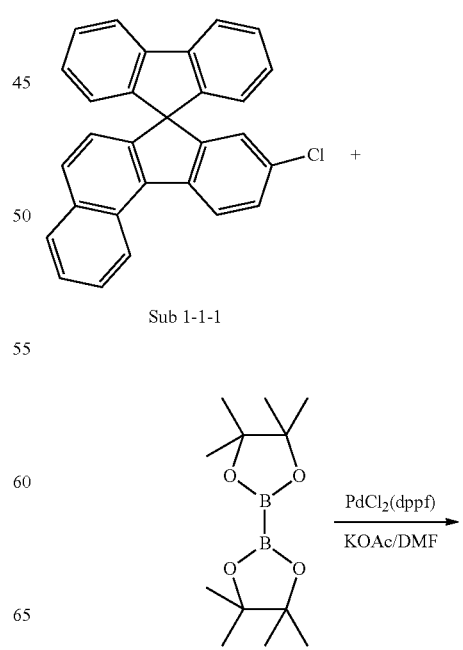

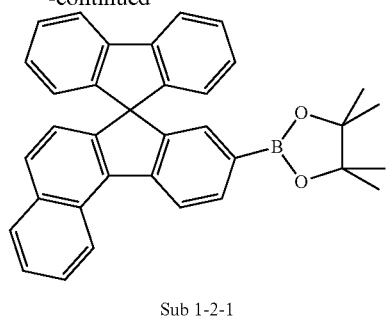

Sub 1-2-1

Sub 1-1-1 (56.13 g, 140 mmol) was dissolved in DMF 980 mL, Bispinacolborate (39.1 g, 154 mmol), PdCl₂(dppf) catalyst (3.43 g, 4.2 mmol), KOAc (41.3 g, 420 mmol) were added in order and stirred for 24 hours and then the obtained compound was separated over a silicagel column and recrystallization to give 39.1 g of the borate compound Sub 1-2-1 (65%).

2) Synthesis of Sub 1-2-2

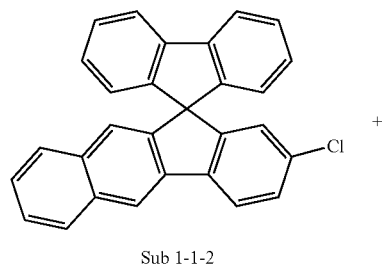

Sub 1-1-2

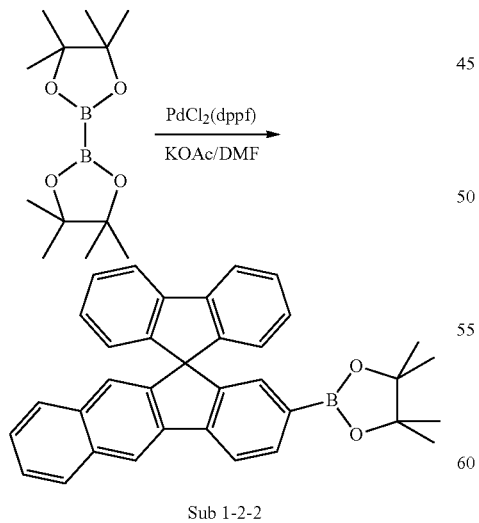

Sub 1-2-2

The same procedure as described in the synthesis method of Sub 1-2-1 was carried out to obtain 40.9 g of the borate compound Sub 1-2-2 (yield: 68%).

3) Synthesis of Sub 1-2-3

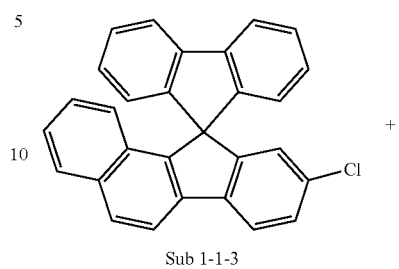

Sub 1-1-3

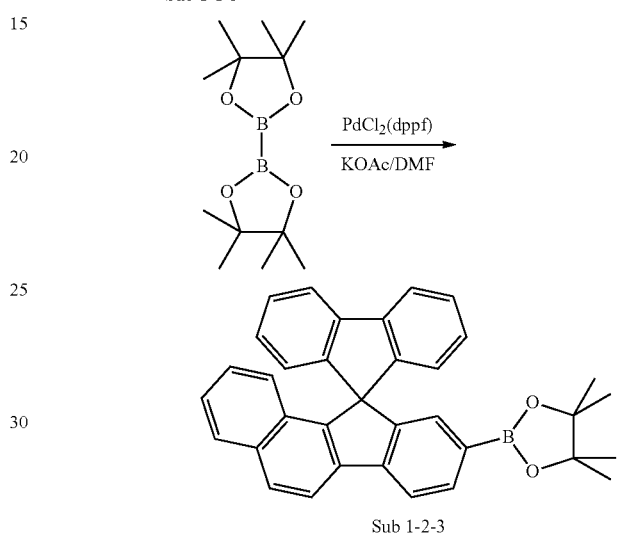

Sub 1-2-3

The same procedure as described in the synthesis method of Sub 1-2-1 was carried out to obtain 39.7 g of the borate compound Sub 1-2-3 (yield: 66%).

Synthesis Examples of Sub 1

1) Synthesis of Sub 1(1)

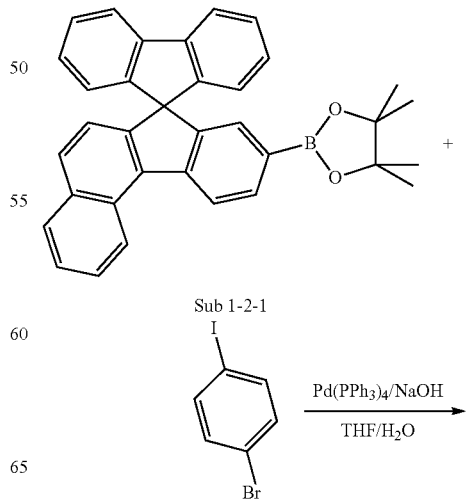

Sub 1-2-1

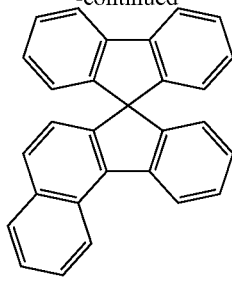

Sub 1(1)

Sub 1-2-1 (39.4 g, 80 mmol), THF 360 mL, 1-bromo-4-iodobenzene (23.8 g, 84 mmol), Pd(PPh$_3$)$_4$ (2.8 g, 2.4 mmol), NaOH (9.6 g, 240 mmol) and 180 mL of water were mixed, and were refluxed with stirring. After the reaction was completed, the reaction mixture was extracted with ether and water. The organic layer was dried over MgSO$_4$ and concentrated. The resulting organic material was separated by silicagel column chromatography and recrystallization to obtain 28.4 g (68%) of the product.

2) Synthesis of Sub 1(2)

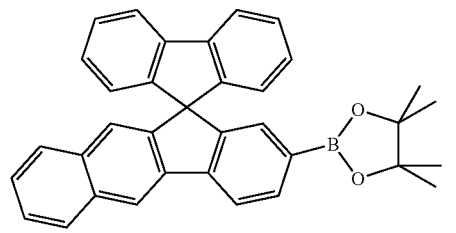

Sub 1-2-2

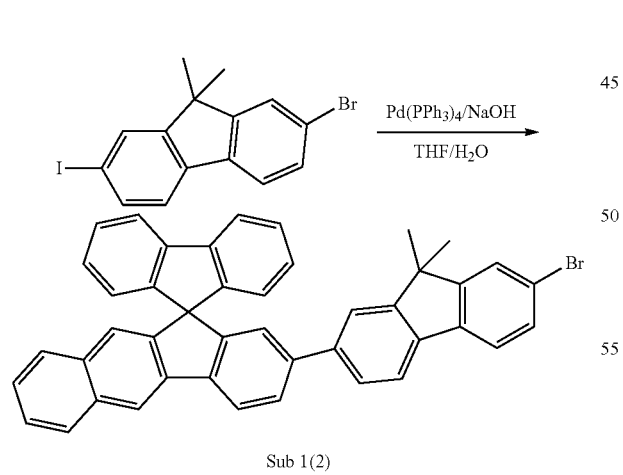

Sub 1(2)

Sub 1-2-2 (39.4 g, 80 mmol), THF 360 mL, 2-bromo-7-iodo-9,9-dimethyl-9H-fluorene (33.5 g, 84 mmol), Pd(PPh$_3$)$_4$ (2.8 g, 2.4 mmol), NaOH (9.6 g, 240 mmol) and 180 mL of water were mixed, the same procedure as described in the synthesis method of Sub 1(1) was carried out to obtain 31.6 g (yield: 62%).

3) Synthesis of Sub 1(3)

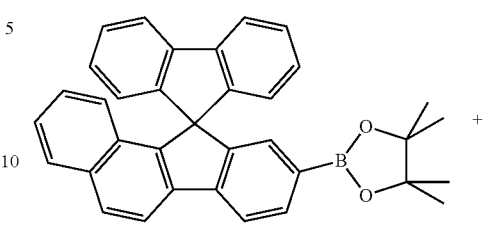

Sub 1-2-3

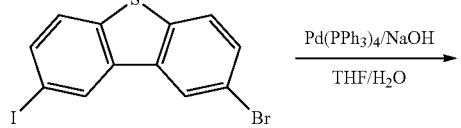

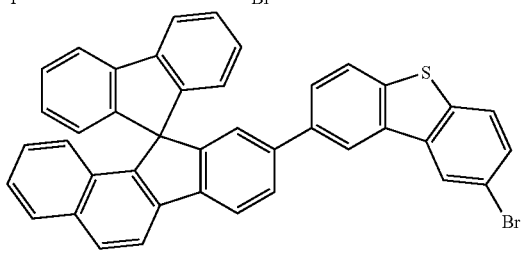

Sub 1(3)

Sub 1-2-3 (39.4 g, 80 mmol), THF 360 mL, 2-bromo-8-iodododibenzo[b,d]thiophene (32.7 g, 84 mmol), Pd(PPh$_3$)$_4$ (2.8 g, 2.4 mmol), NaOH (9.6 g, 240 mmol) and 180 mL of water were mixed, the same procedure as described in the synthesis method of Sub 1(1) was carried out to obtain 32.1 g (yield: 64%).

Examples of Sub 1 include, but are not limited thereto, the following compounds.

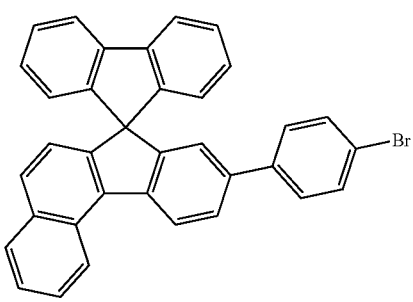

Sub 1(1)

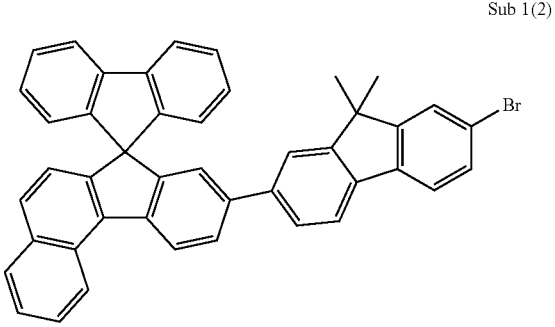

Sub 1(2)

Sub 1(3)
Sub 1(4)
Sub 1(5)
Sub 1(6)
Sub 1(7)
Sub 1(8)
Sub 1(9)
Sub 1(10)
Sub 1(11)
Sub 1(12)
Sub 1(13)

Sub 1(14)
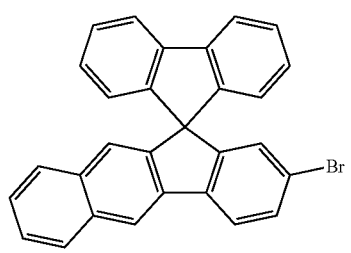
Sub 1(15)
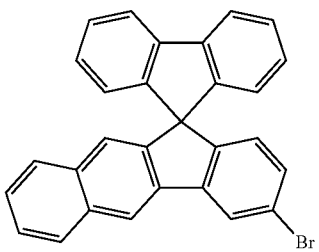
Sub 1(16)
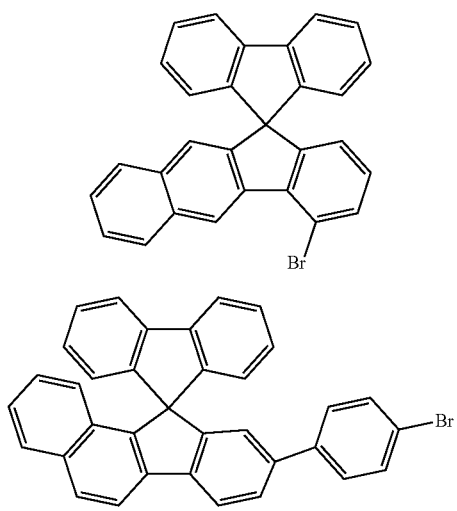
Sub 1(17)
Sub 1(18)
Sub 1(19)
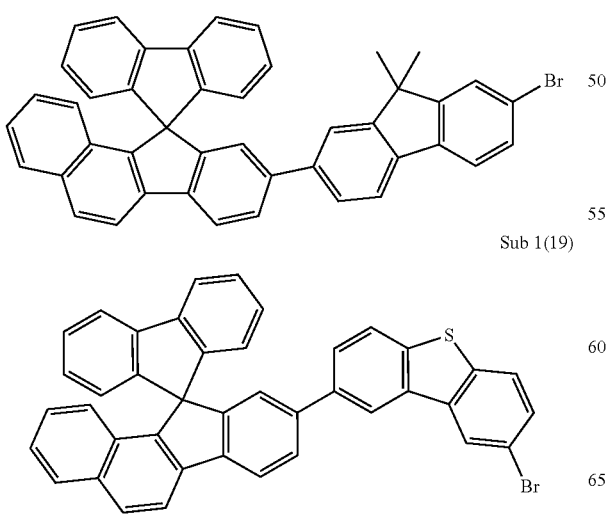
Sub 1(20)
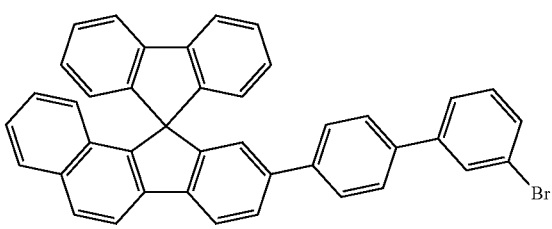
Sub 1(21)
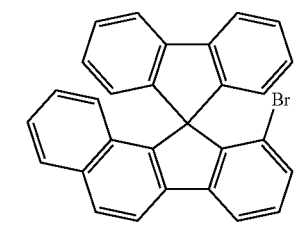
Sub 1(22)
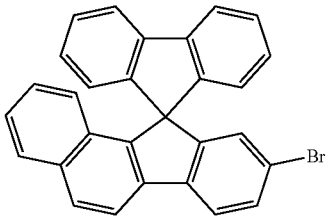
Sub 1(23)
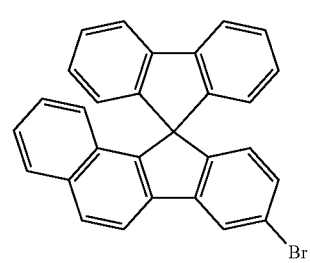
Sub 1(24)
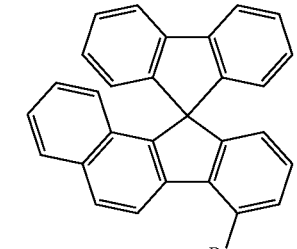
Sub 1(25)
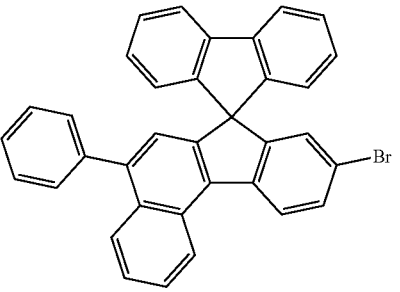

Synthesis Examples of Sub 2-28

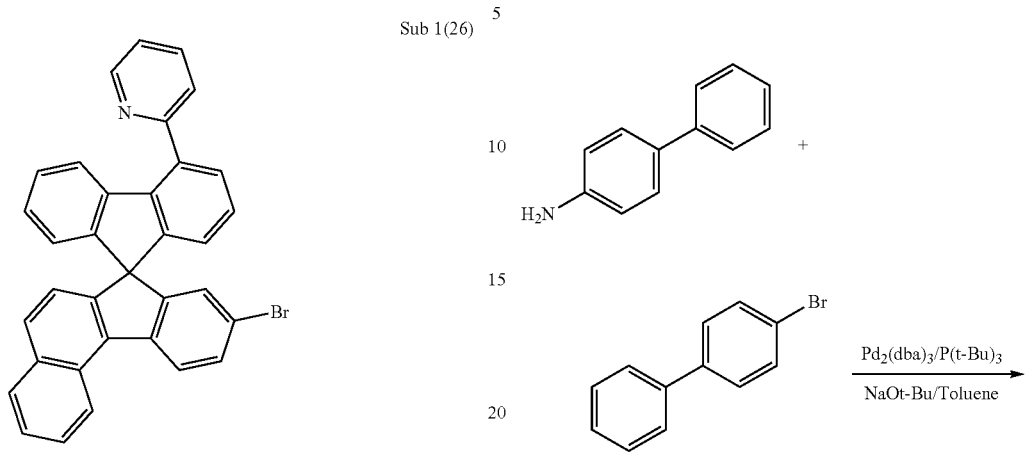

TABLE 1

| compound | FD-MS | compound | FD-MS |
|---|---|---|---|
| Sub 1(1) | m/z = 520.08($C_{35}H_{21}Br$ = 521.45) | Sub 1(2) | m/z = 636.15($C_{44}H_{29}Br$ = 637.61) |
| Sub 1(3) | m/z = 626.07($C_{41}H_{23}BrS$ = 627.59) | Sub 1(4) | m/z = 596.11($C_{41}H_{25}Br$ = 597.54) |
| Sub 1(5) | m/z = 400.10($C_{29}H_{17}Cl$ = 400.90) | Sub 1(6) | m/z = 400.10($C_{29}H_{17}Cl$ = 400.90) |
| Sub 1(7) | m/z = 400.10($C_{29}H_{17}Cl$ = 400.90) | Sub 1(8) | m/z = 400.10($C_{29}H_{17}Cl$ = 400.90) |
| Sub 1(9) | m/z = 520.08($C_{35}H_{21}Br$ = 521.45) | Sub 1(10) | m/z = 636.15($C_{44}H_{29}Br$ = 637.61) |
| Sub 1(11) | m/z = 626.07($C_{41}H_{23}BrS$ = 627.59) | Sub 1(12) | m/z = 596.11($C_{41}H_{25}Br$ = 597.54) |
| Sub 1(13) | m/z = 400.10($C_{29}H_{17}Cl$ = 400.90) | Sub 1(14) | m/z = 400.10($C_{29}H_{17}Cl$ = 400.90) |
| Sub 1(15) | m/z = 400.10($C_{29}H_{17}Cl$ = 400.90) | Sub 1(16) | m/z = 400.10($C_{29}H_{17}Cl$ = 400.90) |
| Sub 1(17) | m/z = 520.08($C_{35}H_{21}Br$ = 521.45) | Sub 1(18) | m/z = 636.15($C_{44}H_{29}Br$ = 637.61) |
| Sub 1(19) | m/z = 626.07($C_{41}H_{23}BrS$ = 627.59) | Sub 1(20) | m/z = 596.11($C_{41}H_{25}Br$ = 597.54) |
| Sub 1(21) | m/z = 400.10($C_{29}H_{17}Cl$ = 400.90) | Sub 1(22) | m/z = 400.10($C_{29}H_{17}Cl$ = 400.90) |
| Sub 1(23) | m/z = 400.10($C_{29}H_{17}Cl$ = 400.90) | Sub 1(24) | m/z = 400.10($C_{29}H_{17}Cl$ = 400.90) |
| Sub 1(25) | m/z = 476.13($C_{35}H_{21}Cl$ = 476.99) | Sub 1(26) | m/z = 477.13($C_{34}H_{20}ClN$ = 477.98) |

Synthesis Examples of Sub 2

Sub 1 of reaction scheme 1 can be synthesized by the reaction path of reaction scheme 2 below, but is not limited thereto.

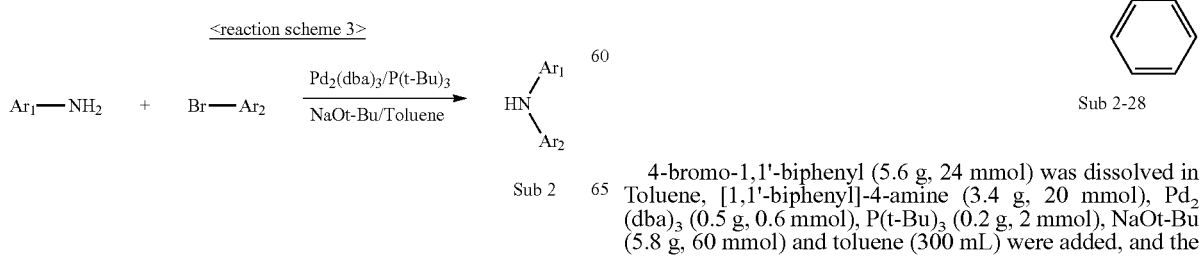

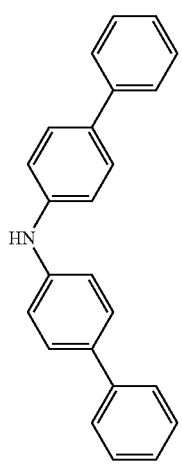

4-bromo-1,1'-biphenyl (5.6 g, 24 mmol) was dissolved in Toluene, [1,1'-biphenyl]-4-amine (3.4 g, 20 mmol), Pd$_2$(dba)$_3$ (0.5 g, 0.6 mmol), P(t-Bu)$_3$ (0.2 g, 2 mmol), NaOt-Bu (5.8 g, 60 mmol) and toluene (300 mL) were added, and the mixture was refluxed at 100° C. for 24 hours. After the reaction was completed, the reaction mixture was extracted with ether and water. The organic layer was dried over MgSO$_4$ and concentrated. The resulting organic material was separated by silicagel column chromatography and recrystallization to obtain 6.2 g of the final product. (yield: 80%)

Examples of Sub 2 include, but are not limited thereto, the following.

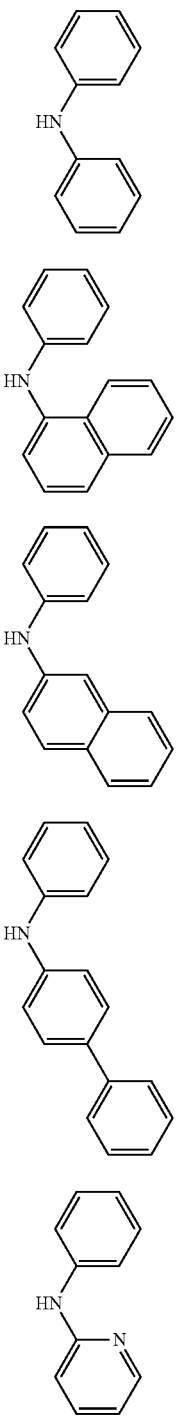

Sub 2-1

Sub 2-2

Sub 2-3

Sub 2-4

Sub 2-5

-continued

Sub 2-6

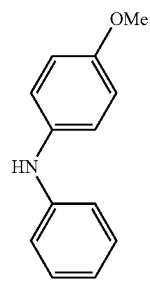

Sub 2-7

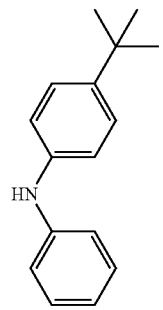

Sub 2-8

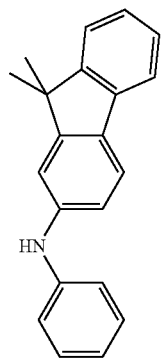

Sub 2-9

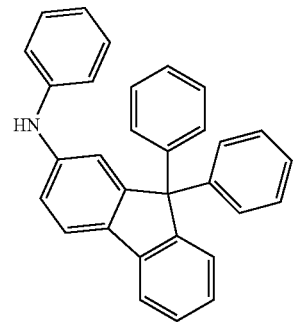

Sub 2-10

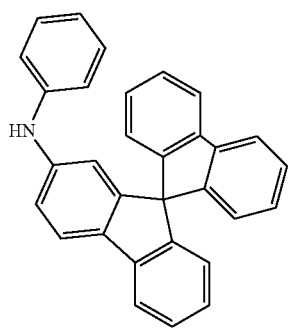

-continued
Sub 2-11
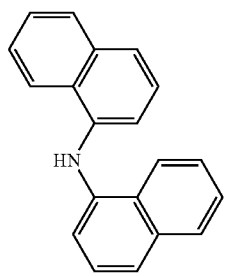
Sub 2-12
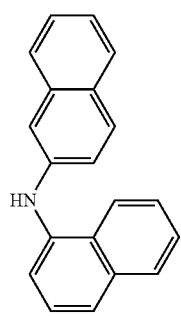
Sub 2-13
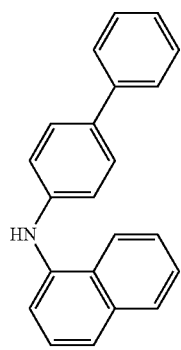
Sub 2-14
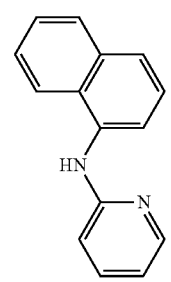
Sub 2-15
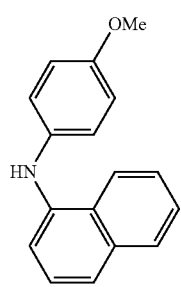
-continued
Sub 2-16
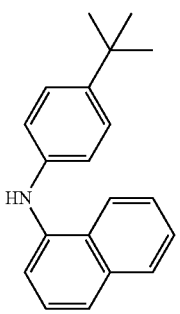
Sub 2-17
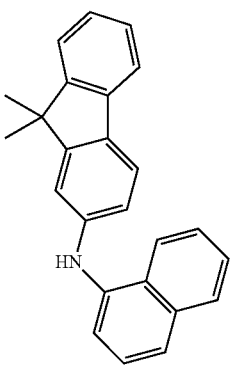
Sub 2-18
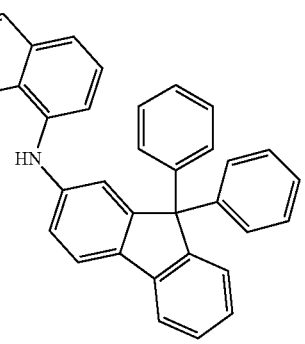
Sub 2-19
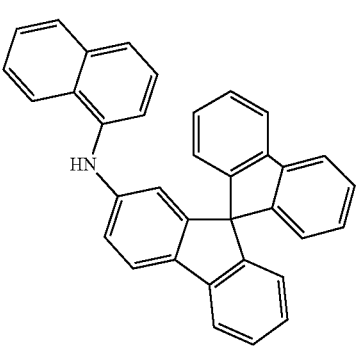

-continued
Sub 2-20
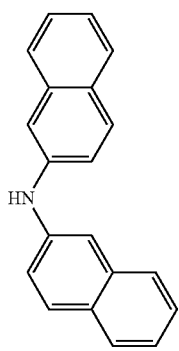
Sub 2-21
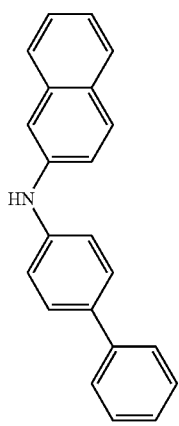
Sub 2-22
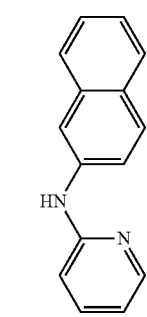
Sub 2-23
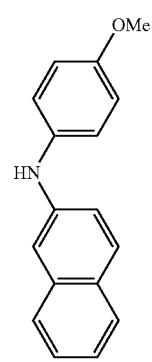
-continued
Sub 2-24
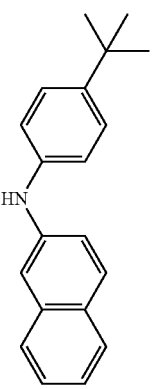
Sub 2-25
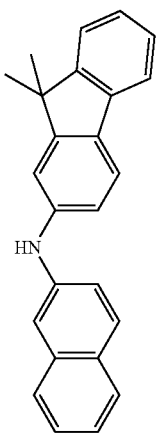
Sub 2-26
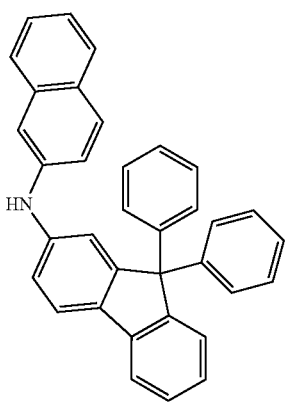
Sub 2-27
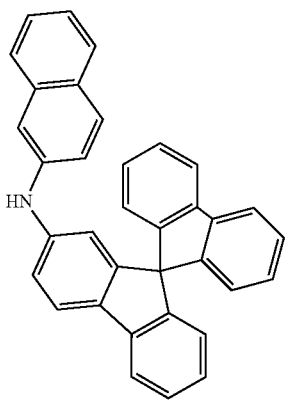

Sub 2-28
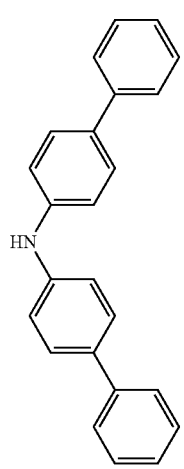
Sub 2-29
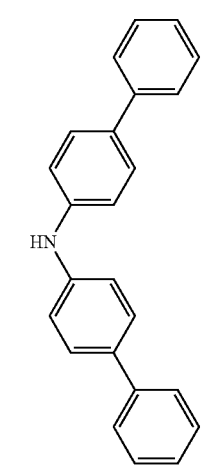
Sub 2-30
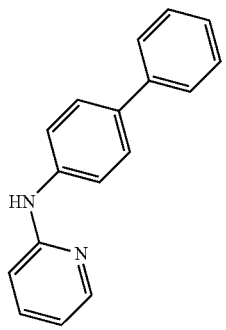
Sub 2-31
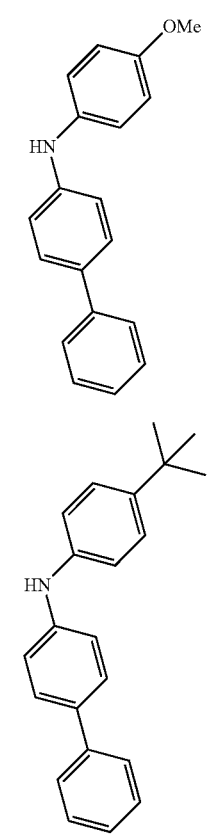
Sub 2-32
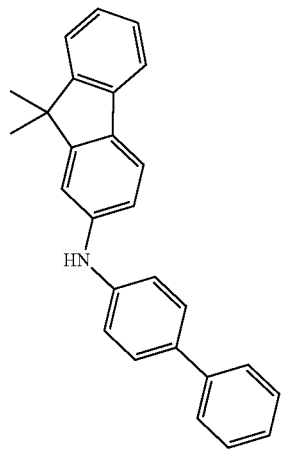
Sub 2-33
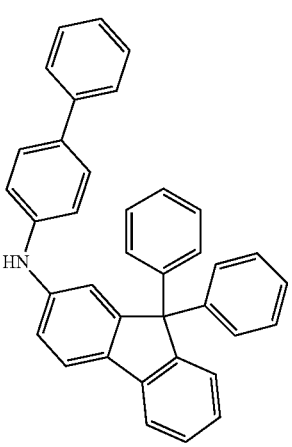
Sub 2-34
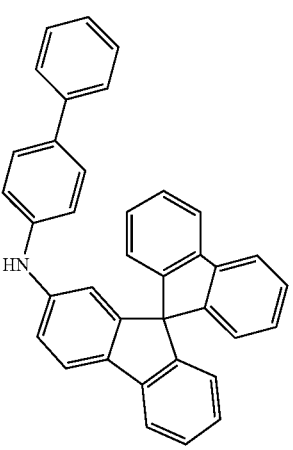
Sub 2-35
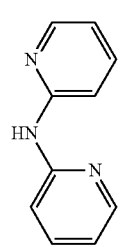

| | |
|---|---|
| Sub 2-36 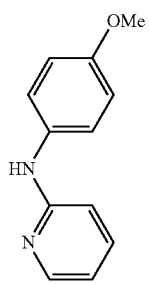 | Sub 2-41 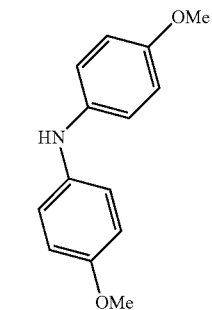 |
| Sub 2-37 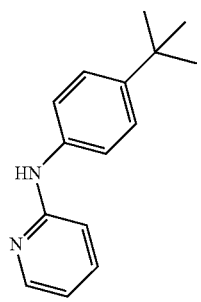 | Sub 2-42 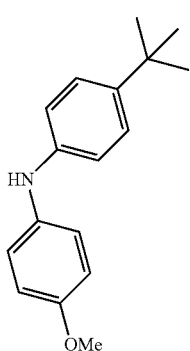 |
| Sub 2-38 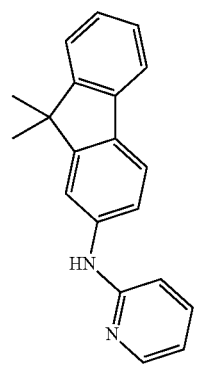 | Sub 2-43 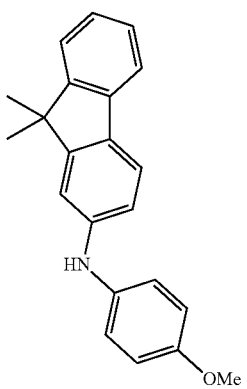 |
| Sub 2-39 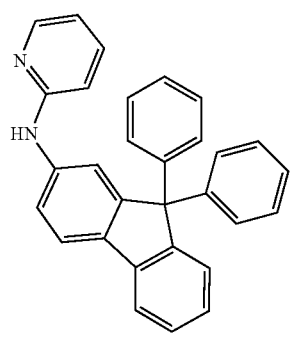 | Sub 2-44 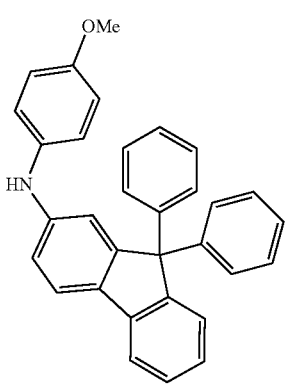 |
| Sub 2-40 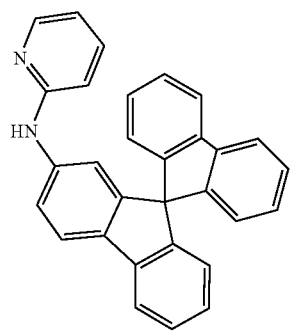 | |

Sub 2-45
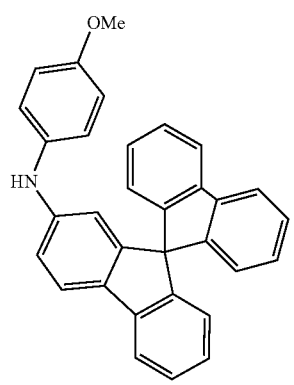
Sub 2-46
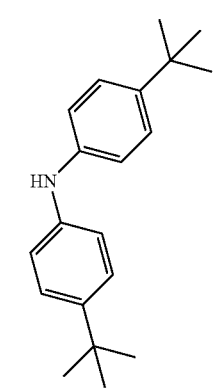
Sub 2-47
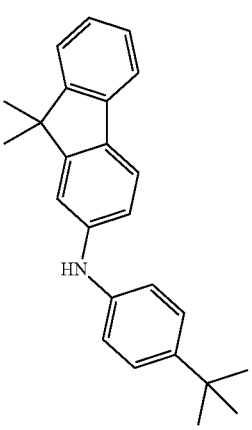
Sub 2-48
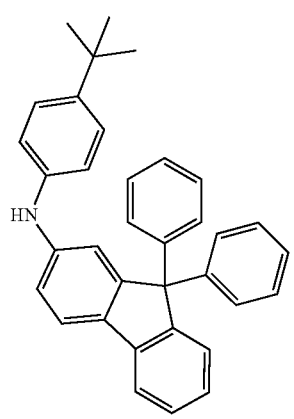
Sub 2-49
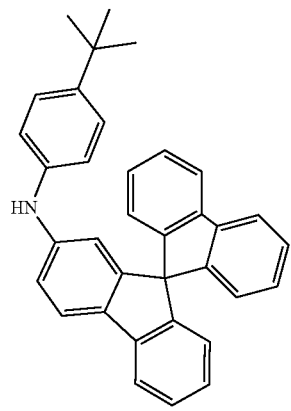
Sub 2-50
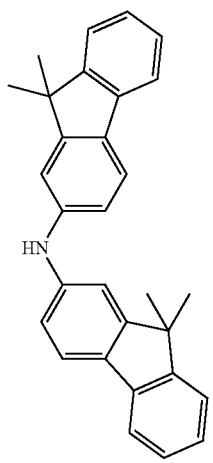
Sub 2-51
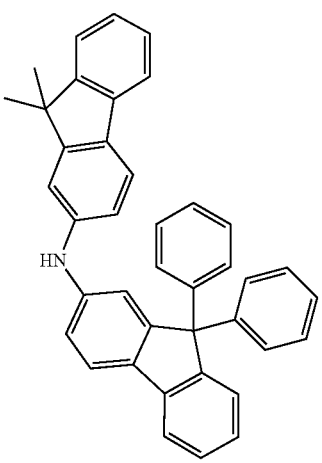

Sub 2-52
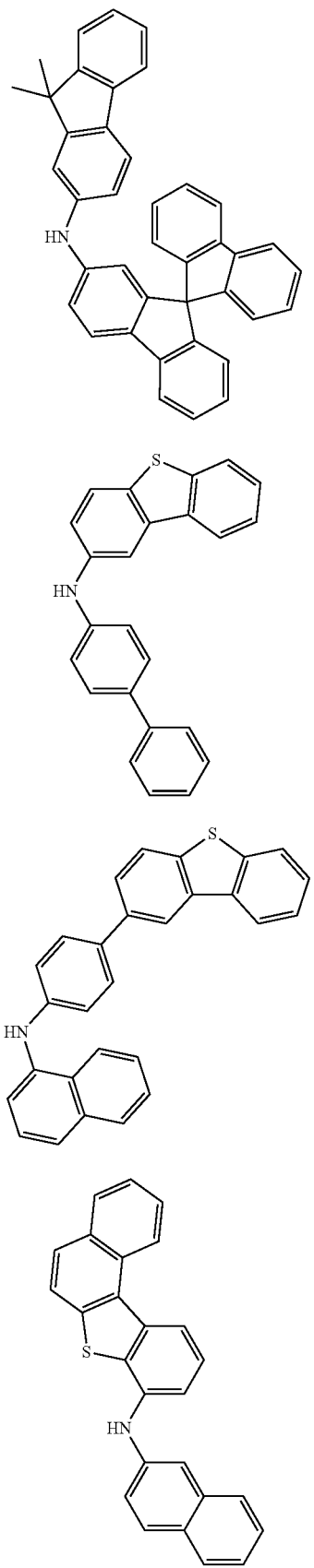
Sub 2-53
Sub 2-54
Sub 2-55
Sub 2-56
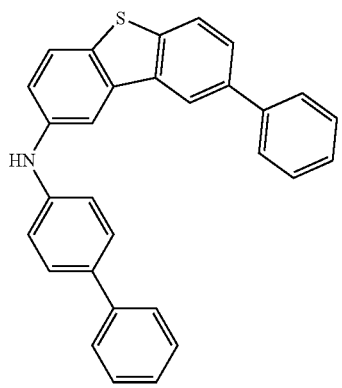
Sub 2-57
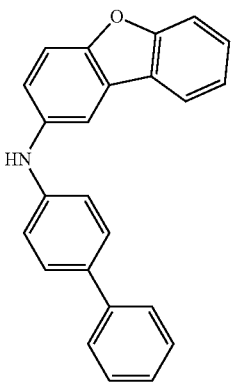
Sub 2-58
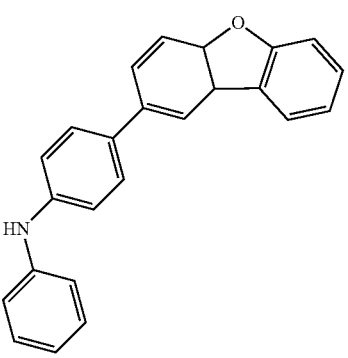
Sub 2-59
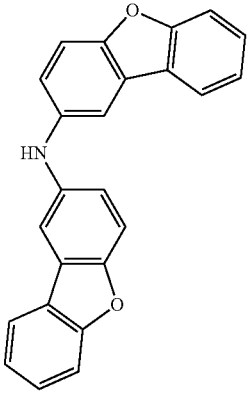

Sub 2-60

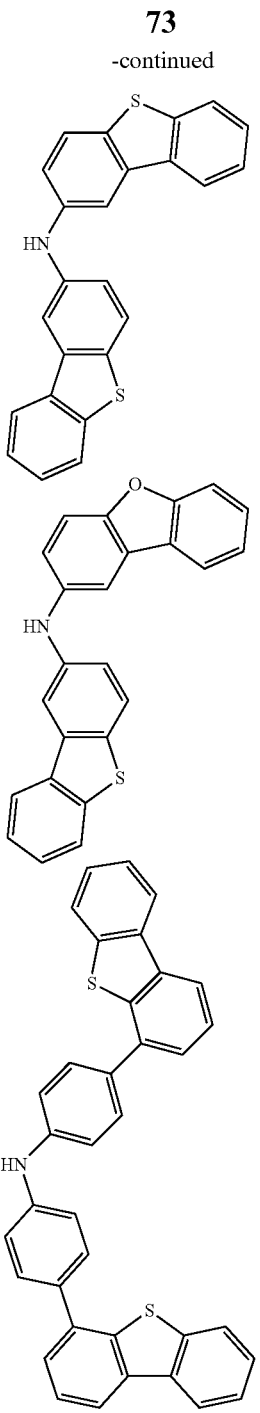

Sub 2-61

Sub 2-62

Sub 2-63

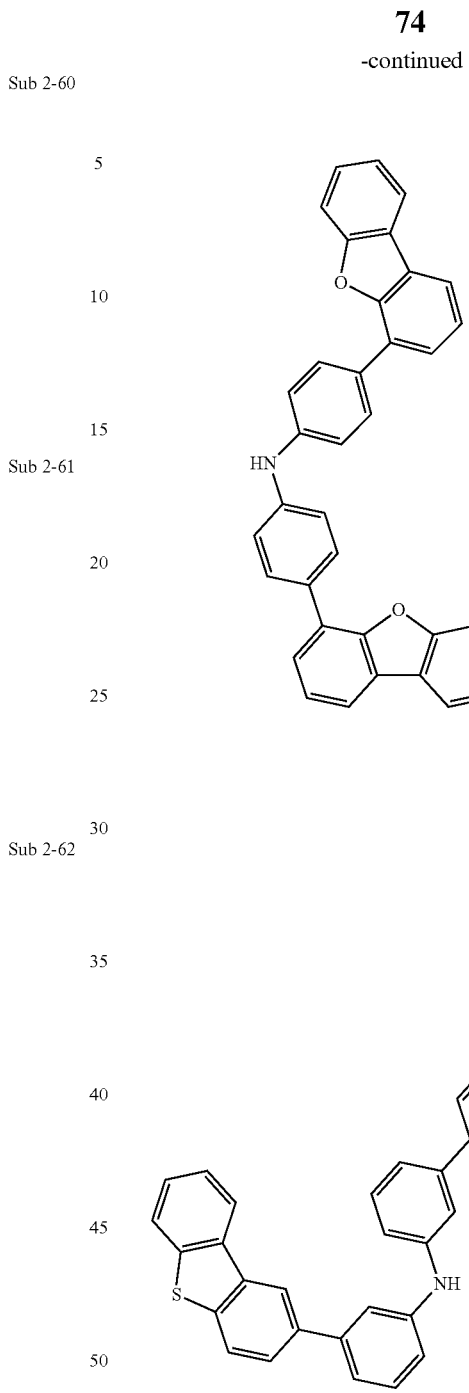

Sub 2-64

TABLE 2

| compound | FD-MS | compound | FD-MS |
|---|---|---|---|
| Sub 2-1 | m/z = 169.09($C_{12}H_{11}N$ = 169.22) | Sub 2-2 | m/z = 219.10($C_{16}H_{13}N$ = 219.28) |
| Sub 2-3 | m/z = 219.10($C_{16}H_{13}N$ = 219.28) | Sub 2-4 | m/z = 245.12($C_{18}H_{15}N$ = 245.32) |
| Sub 2-5 | m/z = 170.08($C_{11}H_{10}N_2$ = 170.21) | Sub 2-6 | m/z = 199.10($C_{10}H_{13}NO$ = 199.25) |
| Sub 2-7 | m/z = 225.15($C_{16}H_{19}N$ = 225.33) | Sub 2-8 | m/z = 285.15($C_{21}H_{19}N$ = 285.38) |
| Sub 2-9 | m/z = 409.18($C_{31}H_{23}N$ = 409.52) | Sub 2-10 | m/z = 407.17($C_{31}H_{21}N$ = 407.51) |
| Sub 2-11 | m/z = 269.12($C_{20}H_{15}N$ = 269.34) | Sub 2-12 | m/z = 269.12($C_{20}H_{15}N$ = 269.34) |
| Sub 2-13 | m/z = 295.14($C_{22}H_{17}N$ = 295.38) | Sub 2-14 | m/z = 220.10($C_{15}H_{12}N_2$ = 220.27) |
| Sub 2-15 | m/z = 249.12($C_{17}H_{12}NO$ = 249.31) | Sub 2-16 | m/z = 275.17($C_{20}H_{21}N$ = 275.39) |
| Sub 2-17 | m/z = 335.17($C_{25}H_{21}N$ = 335.44) | Sub 2-18 | m/z = 459.20($C_{35}H_{25}N$ = 459.58) |
| Sub 2-19 | m/z = 457.18($C_{35}H_{23}N$ = 457.56) | Sub 2-20 | m/z = 269.12($C_{20}H_{15}N$ = 269.34) |
| Sub 2-21 | m/z = 295.14($C_{22}H_{17}N$ = 295.38) | Sub 2-22 | m/z = 220.10($C_{15}H_2N_2$ = 220.27) |

TABLE 2-continued

| compound | FD-MS | compound | FD-MS |
|---|---|---|---|
| Sub 2-23 | m/z = 249.12($C_{17}H_{15}NO$ = 249.31) | Sub 2-24 | m/z = 275.17($C_{20}H_{21}N$ = 275.39) |
| Sub 2-25 | m/z = 335.17($C_{25}H_{21}N$ = 335.44) | Sub 2-26 | m/z = 459.20($C_{35}H_{25}N$ = 459.58) |
| Sub 2-27 | m/z = 457.18($C_{35}H_{23}N$ = 457.56) | Sub 2-28 | m/z = 321.15($C_{24}H_{19}N$ = 321.41) |
| Sub 2-29 | m/z = 246.12($C_{17}H_{14}N_2$ = 246.31) | Sub 2-30 | m/z = 275.13($C_{19}H_{17}NO$ = 275.34) |
| Sub 2-31 | m/z = 301.18($C_{22}H_{23}N$ = 301.42) | Sub 2-32 | m/z = 361.18($C_{27}H_{23}N$ = 361.48) |
| Sub 2-33 | m/z = 485.21($C_{37}H_{27}N$ = 485.62) | Sub 2-34 | m/z = 483.20($C_{37}H_{25}N$ = 483.60) |
| Sub 2-35 | m/z = 171.08($C_{10}H_{09}N_3$ = 171.20) | Sub 2-36 | m/z = 200.09($C_{12}H_{12}N_2O$ = 200.24) |
| Sub 2-37 | m/z = 226.15($C_{15}H_{18}N_2$ = 226.32) | Sub 2-38 | m/z = 286.15($C_{20}H_{18}N_2$ = 286.37) |
| Sub 2-39 | m/z = 410.18($C_{30}H_{22}N_2$ = 410.51) | Sub 2-40 | m/z = 408.16($C_{30}H_{20}N_2$ = 408.49) |
| Sub 2-41 | m/z = 229.11($C_{14}H_{15}NO_2$ = 229.27) | Sub 2-42 | m/z = 255.16($C_{17}H_{21}NO$ = 255.35) |
| Sub 2-43 | m/z = 315.16($C_{22}H_{21}NO$ = 315.41) | Sub 2-44 | m/z = 439.19($C_{32}H_{25}NO$ = 439.55) |
| Sub 2-45 | m/z = 437.18($C_{32}H_{23}NO$ = 437.53) | Sub 2-46 | m/z = 281.21($C_{20}H_{27}N$ = 281.44) |
| Sub 2-47 | m/z = 341.21($C_{25}H_{27}N$ = 341.49) | Sub 2-48 | m/z = 465.25($C_{35}H_{31}N$ = 465.63) |
| Sub 2-49 | m/z = 463.23($C_{35}H_{29}N$ = 463.61) | Sub 2-50 | m/z = 401.21($C_{30}H_{27}N$ = 401.54) |
| Sub 2-51 | m/z = 525.25($C_{40}H_{31}N$ = 525.68) | Sub 2-52 | m/z = 523.23($C_{40}H_{29}N$ = 523.66) |
| Sub 2-53 | m/z = 351.11($C_{24}H_{17}NS$ = 351.46) | Sub 2-54 | m/z = 401.12($C_{28}H_{19}NS$ = 401.52) |
| Sub 2-55 | m/z = 357.11($C_{26}H_{17}NS$ = 375.48) | Sub 2-56 | m/z = 427.14($C_{30}H_{21}NS$ = 427.56) |
| Sub 2-57 | m/z = 335.13($C_{24}H_{17}NO$ = 335.40) | Sub 2-58 | m/z = 335.13($C_{24}H_{17}NO$ = 335.40) |
| Sub 2-59 | m/z = 349.11($C_{24}H_{15}NO_2$ = 349.38) | Sub 2-60 | m/z = 381.06($C_{24}H_{15}NS_2$ = 381.51) |
| Sub 2-61 | m/z = 365.09($C_{24}H_{15}NOS$ = 365.45) | Sub 2-62 | m/z = 533.13($C_{36}H_{23}NS_2$ = 533.70) |
| Sub 2-63 | m/z = 501.17($C_{36}H_{23}NO_2$ = 501.57) | Sub 2-64 | m/z = 517.15($C_{36}H_{23}NOS$ = 349.38) |

Synthesis Example of Final Products

Synthesis Example of 1-12

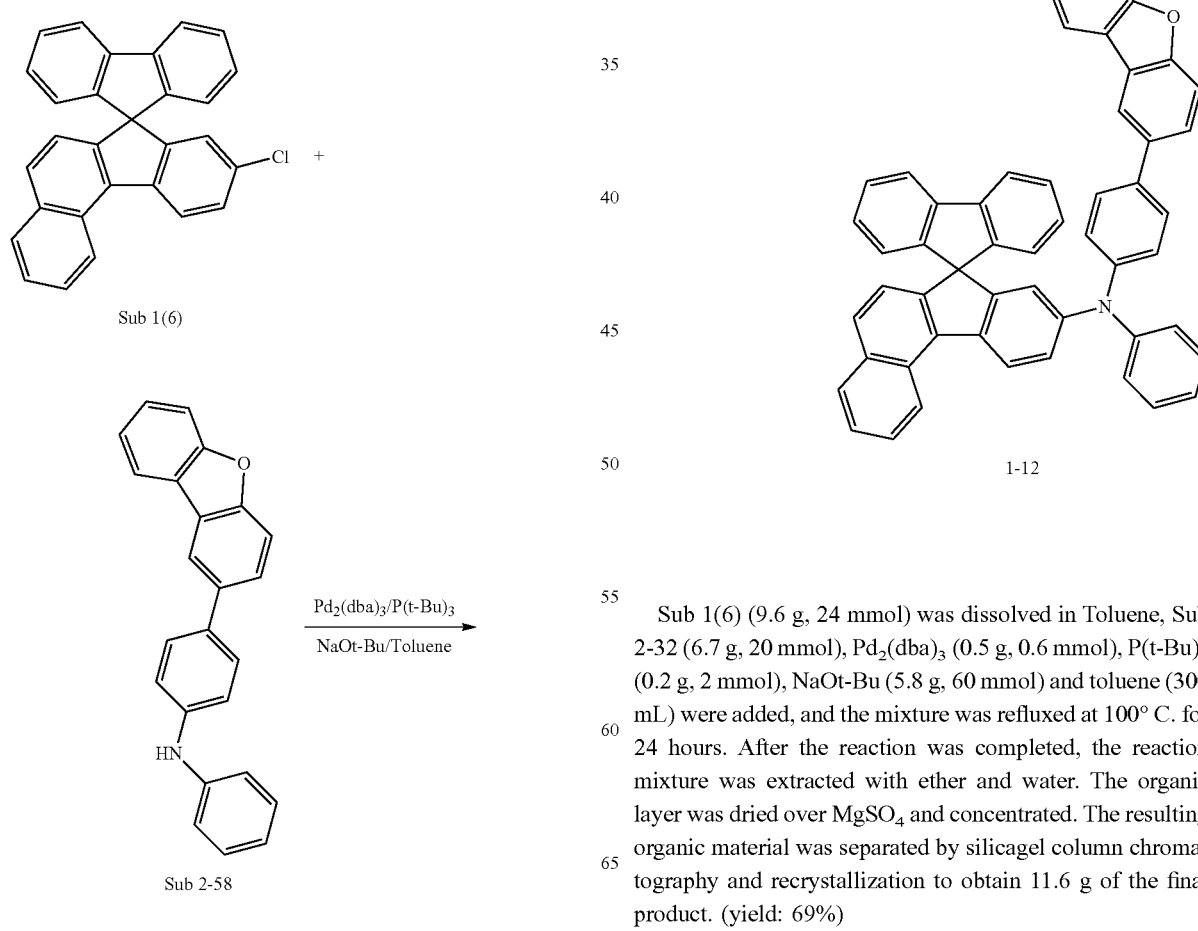

Sub 1(6) (9.6 g, 24 mmol) was dissolved in Toluene, Sub 2-32 (6.7 g, 20 mmol), Pd$_2$(dba)$_3$ (0.5 g, 0.6 mmol), P(t-Bu)$_3$ (0.2 g, 2 mmol), NaOt-Bu (5.8 g, 60 mmol) and toluene (300 mL) were added, and the mixture was refluxed at 100° C. for 24 hours. After the reaction was completed, the reaction mixture was extracted with ether and water. The organic layer was dried over MgSO$_4$ and concentrated. The resulting organic material was separated by silicagel column chromatography and recrystallization to obtain 11.6 g of the final product. (yield: 69%)

Synthesis Example of 1-13

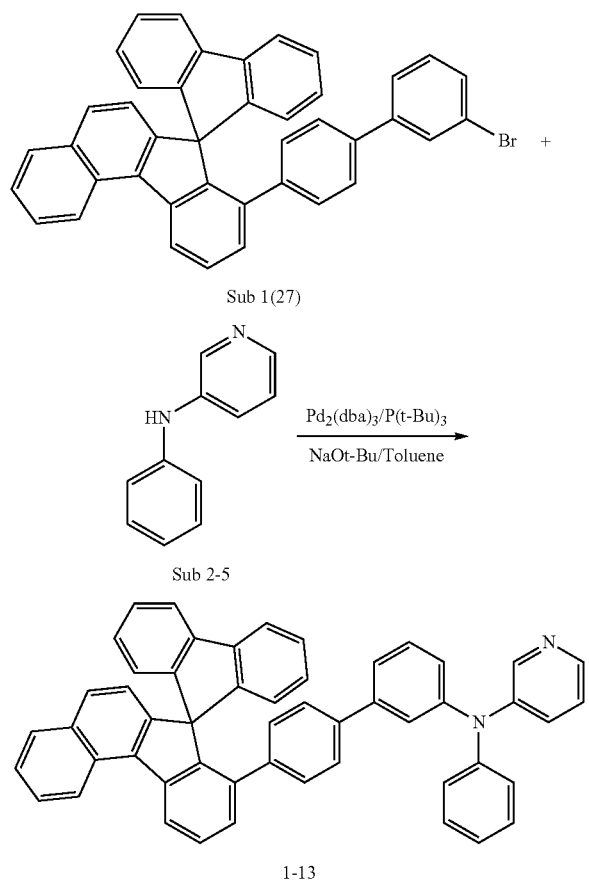

Sub 1(27)

Sub 2-5

1-13

Sub 1(27) (14.3 g, 24 mmol) was dissolved in Toluene, Sub 2-5 (3.4 g, 20 mmol), Pd$_2$(dba)$_3$ (0.5 g, 0.6 mmol), P(t-Bu)$_3$ (0.2 g, 2 mmol), NaOt-Bu (5.8 g, 60 mmol) and toluene (300 mL) were added, the same procedure as described in the synthesis method of the 1-12 was carried out to obtain 10.1 g of the final product. (yield: 61%).

Synthesis Example of 1-15

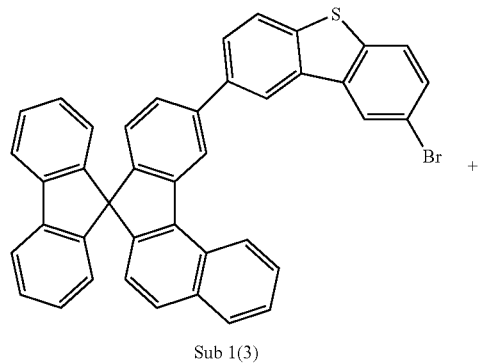

Sub 1(3)

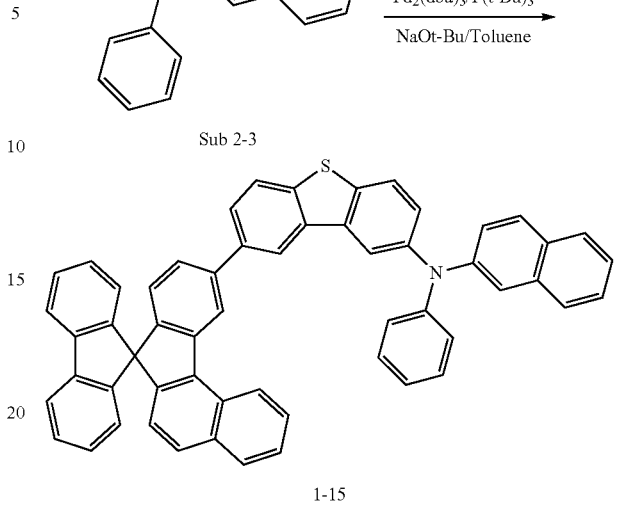

Sub 2-3

1-15

Sub 1(3) (15.1 g, 24 mmol) was dissolved in Toluene, Sub 2-3 (4.4 g, 20 mmol), Pd$_2$(dba)$_3$ (0.5 g, 0.6 mmol), P(t-Bu)$_3$ (0.2 g, 2 mmol), NaOt-Bu (5.8 g, 60 mmol) and toluene (300 mL) were added, the same procedure as described in the synthesis method of the 1-12 was carried out to obtain 10.7 g of the final product. (yield: 65%).

Synthesis Example of 1-22

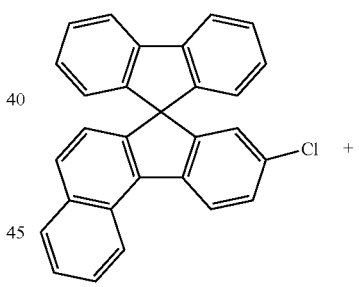

Sub 1(6)

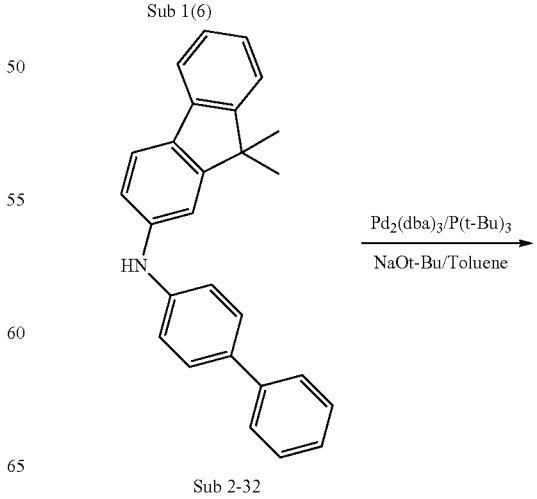

Sub 2-32

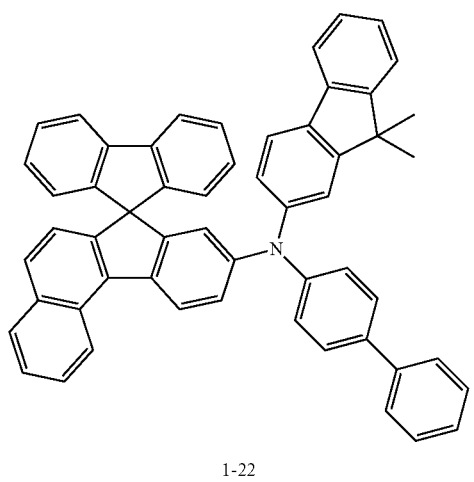

1-22

Sub 1(6) (9.6 g, 24 mmol) was dissolved in Toluene, Sub 2-32 (7.2 g, 20 mmol), Pd$_2$(dba)$_3$ (0.5 g, 0.6 mmol), P(t-Bu)$_3$ (0.2 g, 2 mmol), NaOt-Bu (5.8 g, 60 mmol) and toluene (300 mL) were added, the same procedure as described in the synthesis method of the 1-12 was carried out to obtain 11.3 g of the final product. (yield: 65%).

Synthesis Example of 1-30

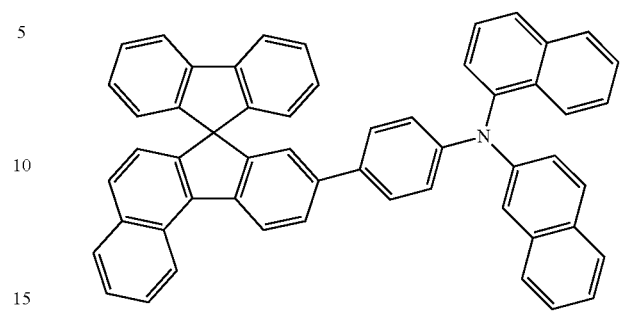

1-30

Sub 1(1) (12.5 g, 24 mmol) was dissolved in Toluene, Sub 2-12 (5.4 g, 20 mmol), Pd$_2$(dba)$_3$ (0.5 g, 0.6 mmol), P(t-Bu)$_3$ (0.2 g, 2 mmol), NaOt-Bu (5.8 g, 60 mmol) and toluene (300 mL) were added, the same procedure as described in the synthesis method of the 1-12 was carried out to obtain 11.2 g of the final product. (yield: 66%).

Synthesis Example of 1-32

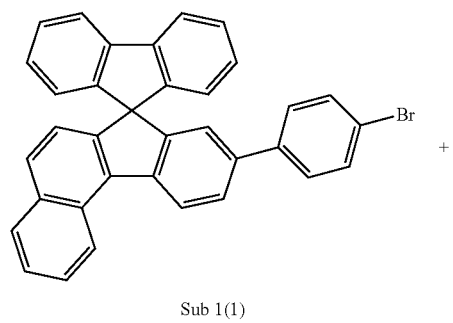

Sub 1(1)

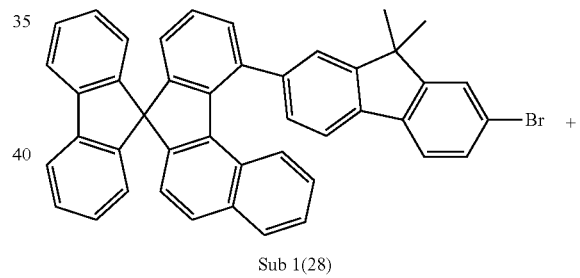

Sub 1(28)

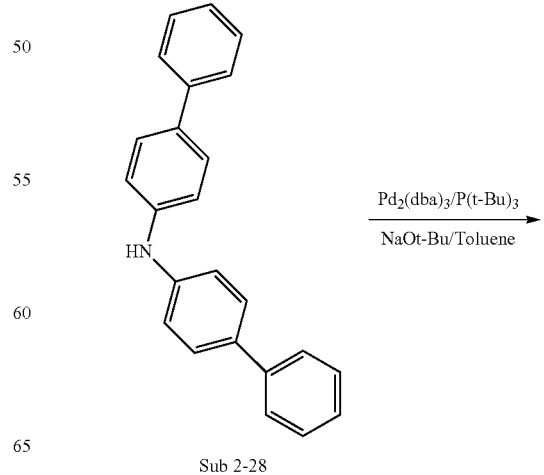

Sub 2-12

Sub 2-28

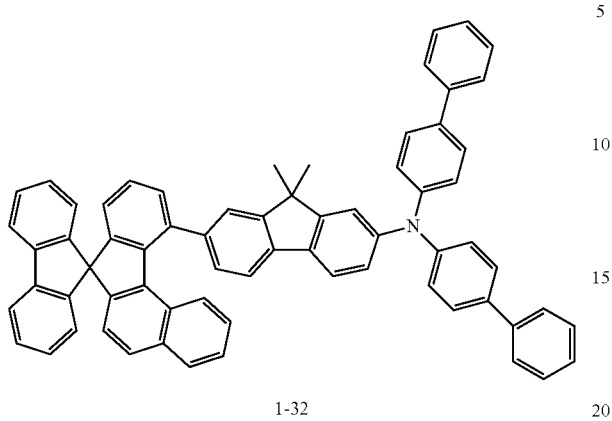

1-32

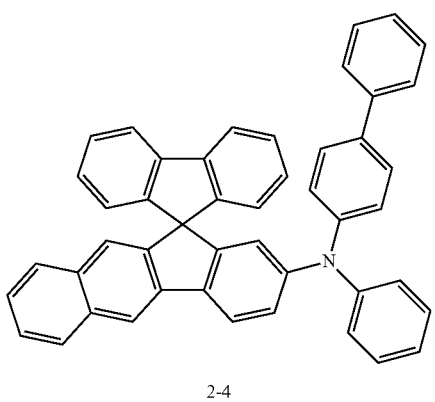

2-4

Sub 1(28) (15.3 g, 24 mmol) was dissolved in Toluene, Sub 2-28 (6.4 g, 20 mmol), Pd$_2$(dba)$_3$ (0.5 g, 0.6 mmol), P(t-Bu)$_3$ (0.2 g, 2 mmol), NaOt-Bu (5.8 g, 60 mmol) and toluene (300 mL) were added, the same procedure as described in the synthesis method of the 1-12 was carried out to obtain 12.6 g of the final product. (yield: 60%).

Synthesis Example of 2-4

Sub 1(14) (9.6 g, 24 mmol) was dissolved in Toluene, Sub 2-4 (4.9 g, 20 mmol), Pd$_2$(dba)$_3$ (0.5 g, 0.6 mmol), P(t-Bu)$_3$ (0.2 g, 2 mmol), NaOt-Bu (5.8 g, 60 mmol) and toluene (300 mL) were added, the same procedure as described in the synthesis method of the 1-12 was carried out to obtain 10.1 g of the final product. (yield: 69%).

Synthesis Example of 2-8

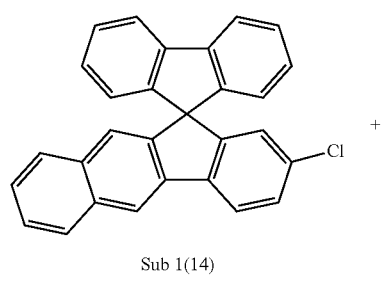

Sub 1(14)

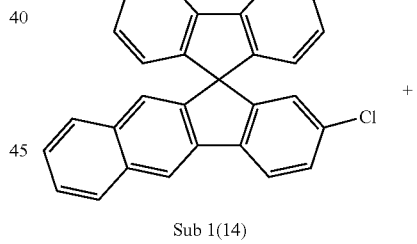

Sub 1(14)

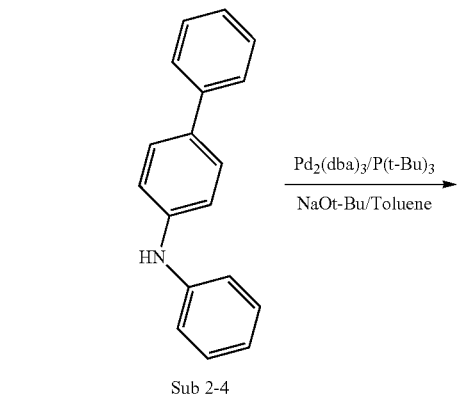

Sub 2-4

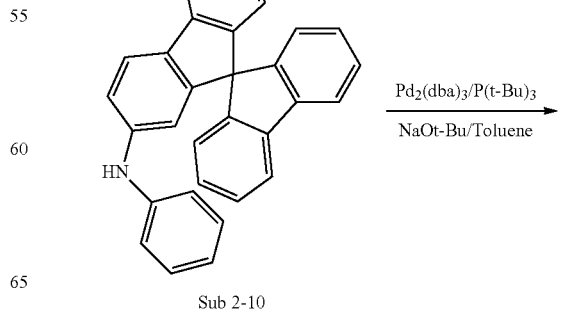

Sub 2-10

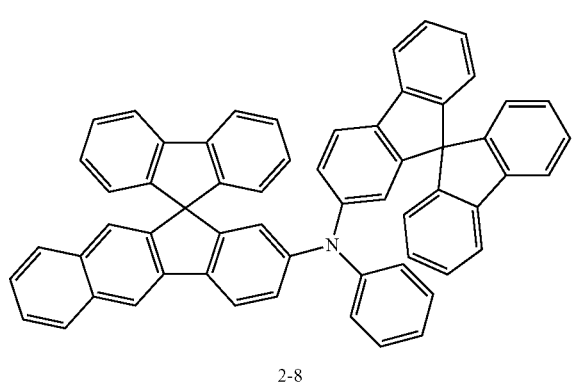

2-8

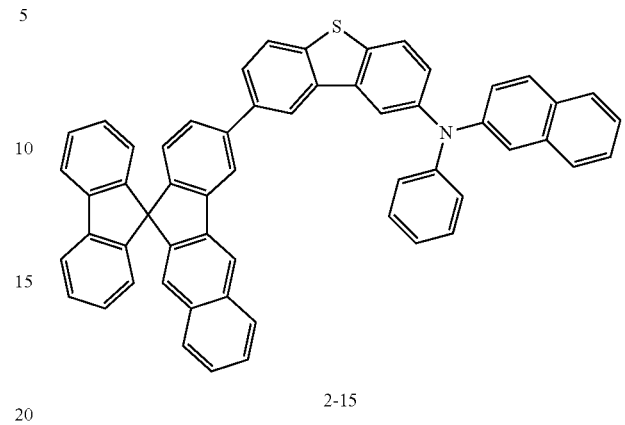

2-15

Sub 1(14) (9.6 g, 24 mmol) was dissolved in Toluene, Sub 2-10 (8.2 g, 20 mmol), Pd$_2$(dba)$_3$ (0.5 g, 0.6 mmol), P(t-Bu)$_3$ (0.2 g, 2 mmol), NaOt-Bu (5.8 g, 60 mmol) and toluene (300 mL) were added, the same procedure as described in the synthesis method of the 1-12 was carried out to obtain 11.7 g of the final product. (yield: 63%).

Synthesis Example of 2-15

Sub 1(11) (15.1 g, 24 mmol) was dissolved in Toluene, Sub 2-3 (4.4 g, 20 mmol), Pd$_2$(dba)$_3$ (0.5 g, 0.6 mmol), P(t-Bu)$_3$ (0.2 g, 2 mmol), NaOt-Bu (5.8 g, 60 mmol) and toluene (300 mL) were added, the same procedure as described in the synthesis method of the 1-12 was carried out to obtain 11.6 g of the final product. (yield: 64%).

Synthesis Example of 2-16

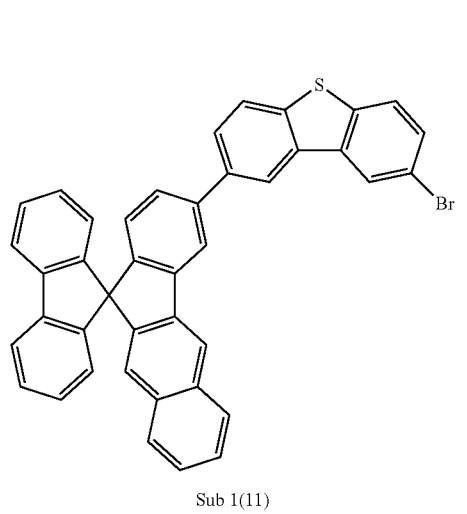

Sub 1(11)

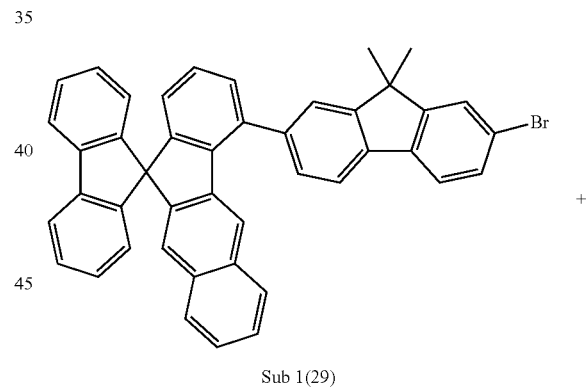

Sub 1(29)

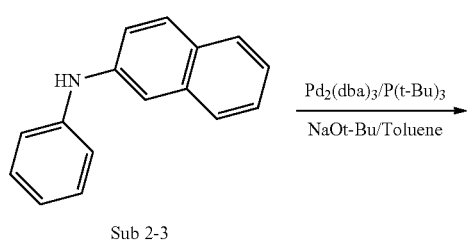

Sub 2-3

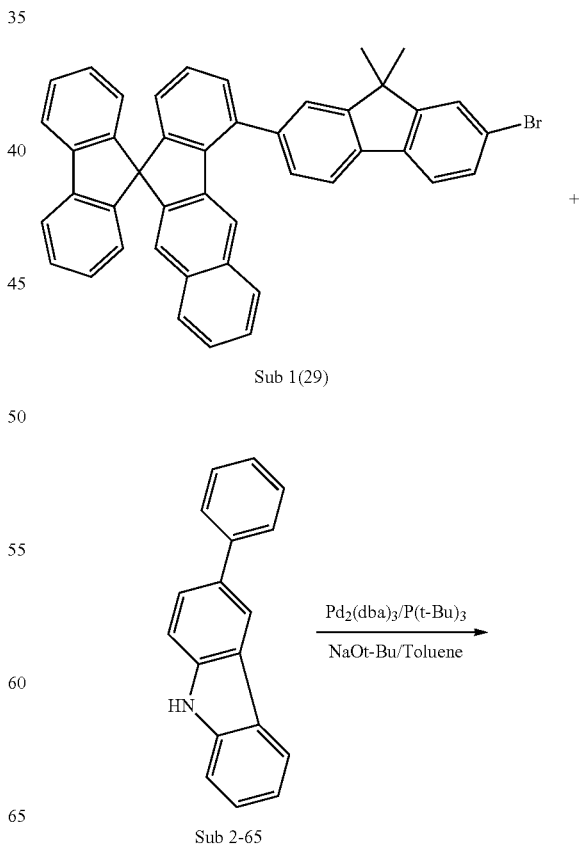

Sub 2-65

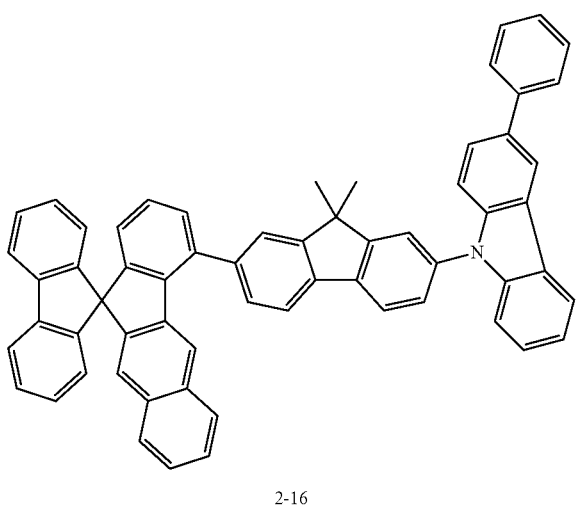

2-16

Sub 1(29) (15.3 g, 24 mmol) was dissolved in Toluene, Sub 2-65 (4.9 g, 20 mmol), Pd$_2$(dba)$_3$ (0.5 g, 0.6 mmol), P(t-Bu)$_3$ (0.2 g, 2 mmol), NaOt-Bu (5.8 g, 60 mmol) and toluene (300 mL) were added, the same procedure as described in the synthesis method of the 1-12 was carried out to obtain 11.9 g of the final product. (yield: 62%).

Synthesis Example of 2-30

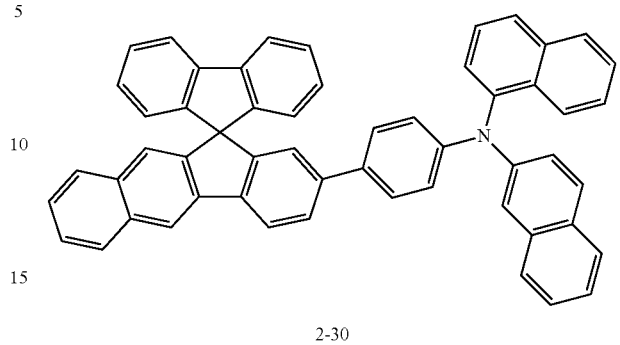

2-30

Sub 1(9) (12.5 g, 24 mmol) was dissolved in Toluene, Sub 2-12 (5.4 g, 20 mmol), Pd$_2$(dba)$_3$ (0.5 g, 0.6 mmol), P(t-Bu)$_3$ (0.2 g, 2 mmol), NaOt-Bu (5.8 g, 60 mmol) and toluene (300 mL) were added, the same procedure as described in the synthesis method of the 1-12 was carried out to obtain 11.6 g of the final product. (yield: 68%).

Synthesis Example of 2-37

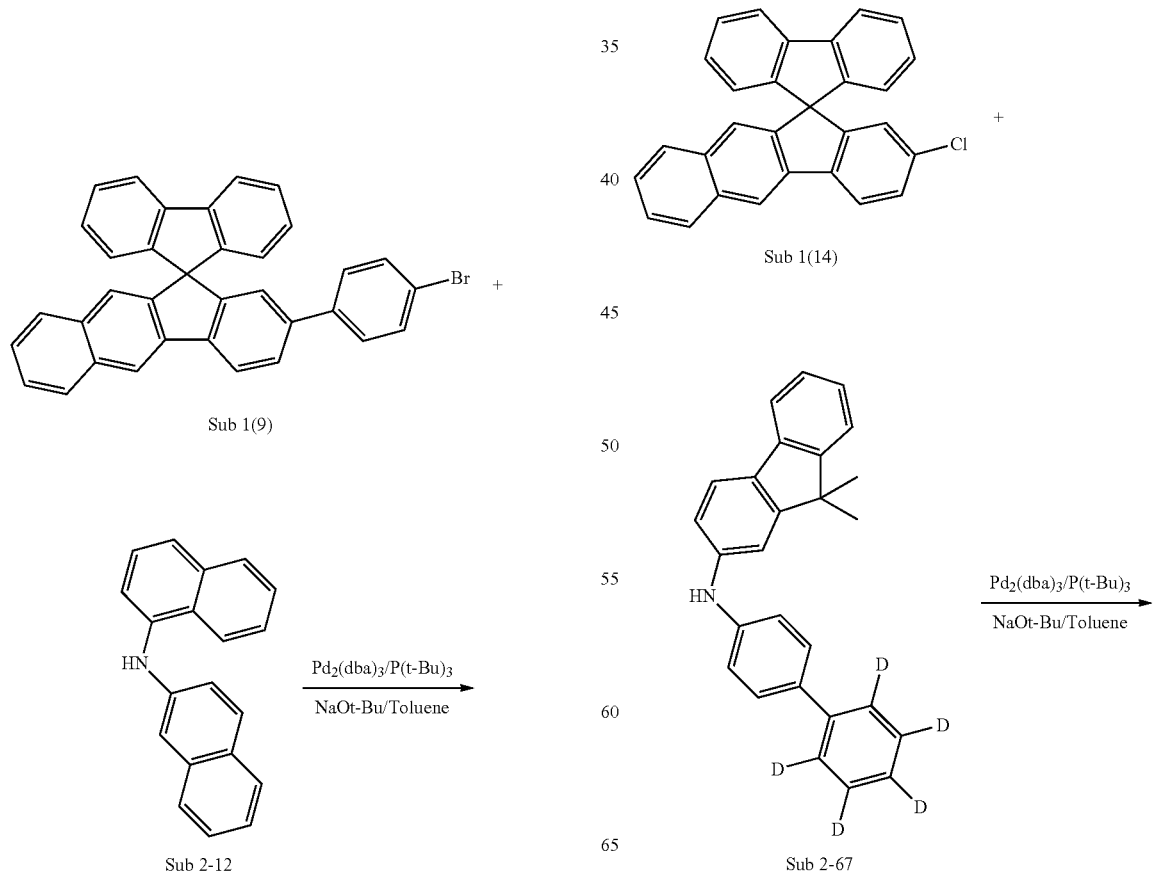

-continued

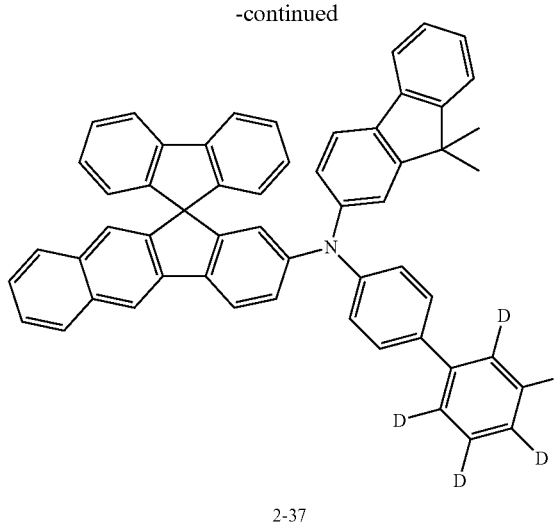

2-37

Sub 1(14) (9.6 g, 24 mmol) was dissolved in Toluene, Sub 2-67 (7.3 g, 20 mmol), Pd$_2$(dba)$_3$ (0.5 g, 0.6 mmol), P(t-Bu)$_3$ (0.2 g, 2 mmol), NaOt-Bu (5.8 g, 60 mmol) and toluene (300 mL) were added, the same procedure as described in the synthesis method of the 1-12 was carried out to obtain 11.2 g of the final product. (yield: 64%).

Synthesis Example of 3-5

Sub 1(22) (9.6 g, 24 mmol) was dissolved in Toluene, Sub 2-66 (4.9 g, 20 mmol), Pd$_2$(dba)$_3$ (0.5 g, 0.6 mmol), P(t-Bu)$_3$ (0.2 g, 2 mmol), NaOt-Bu (5.8 g, 60 mmol) and toluene (300 mL) were added, the same procedure as described in the synthesis method of the 1-12 was carried out to obtain 9.7 g of the final product. (yield: 66%).

Synthesis Example of 3-12

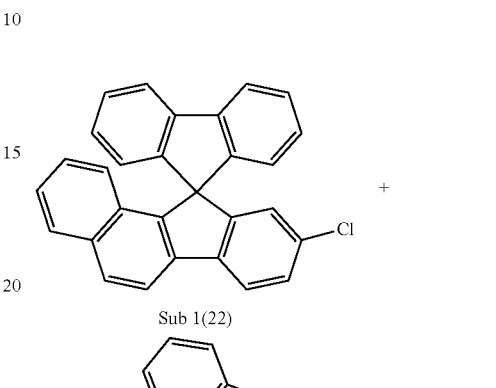

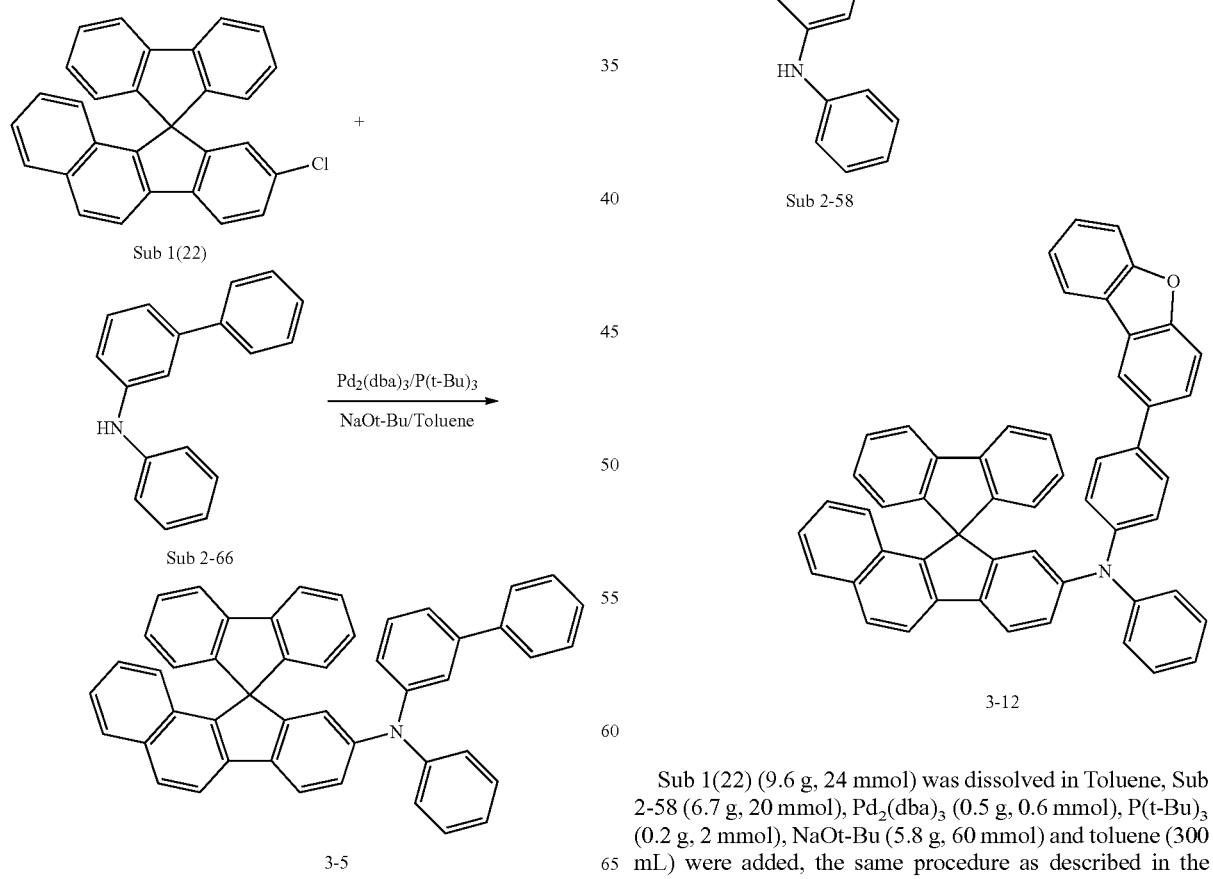

Sub 1(22) (9.6 g, 24 mmol) was dissolved in Toluene, Sub 2-58 (6.7 g, 20 mmol), Pd$_2$(dba)$_3$ (0.5 g, 0.6 mmol), P(t-Bu)$_3$ (0.2 g, 2 mmol), NaOt-Bu (5.8 g, 60 mmol) and toluene (300 mL) were added, the same procedure as described in the synthesis method of the 1-12 was carried out to obtain 10.2 g of the final product. (yield: 61%).

Synthesis Example of 3-14

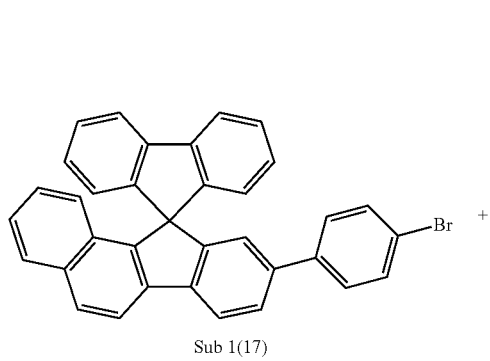

Sub 1(17)

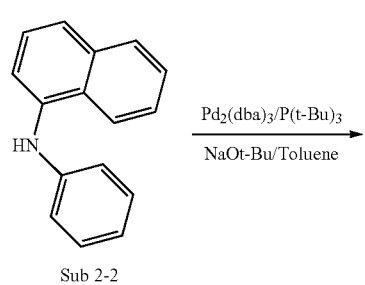

Sub 2-2

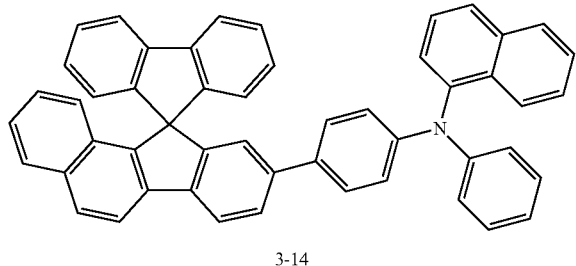

3-14

Sub 1(17) (12.5 g, 24 mmol) was dissolved in Toluene, Sub 2-2 (4.4 g, 20 mmol), Pd$_2$(dba)$_3$ (0.5 g, 0.6 mmol), P(t-Bu)$_3$ (0.2 g, 2 mmol), NaOt-Bu (5.8 g, 60 mmol) and toluene (300 mL) were added, the same procedure as described in the synthesis method of the 1-12 was carried out to obtain 10.8 g of the final product. (yield: 68%).

Synthesis Example of 3-29

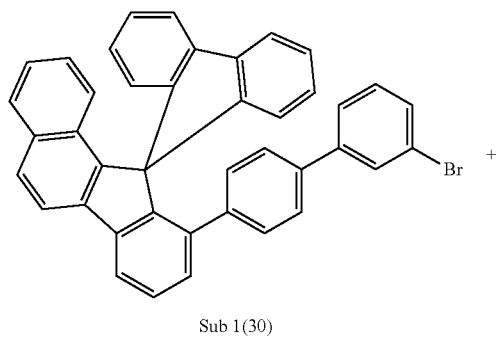

Sub 1(30)

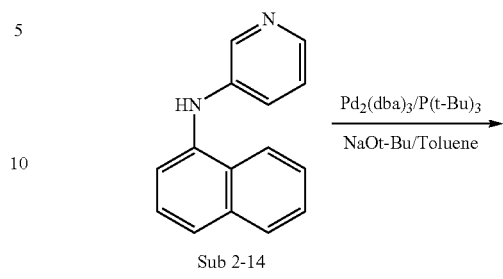

Sub 2-14

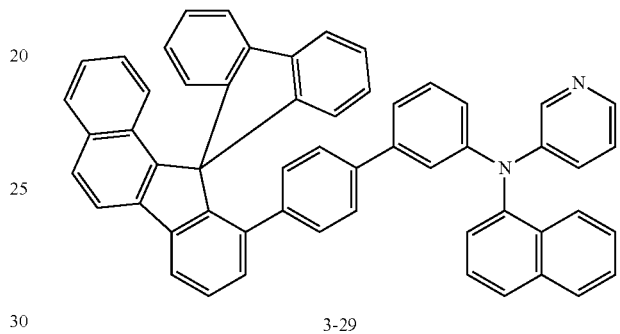

3-29

Sub 1(30) (14.3 g, 24 mmol) was dissolved in Toluene, Sub 2-14 (4.4 g, 20 mmol), Pd$_2$(dba)$_3$ (0.5 g, 0.6 mmol), P(t-Bu)$_3$ (0.2 g, 2 mmol), NaOt-Bu (5.8 g, 60 mmol) and toluene (300 mL) were added, the same procedure as described in the synthesis method of the 1-12 was carried out to obtain 10.4 g of the final product. (yield: 59%).

Synthesis Example of 3-31

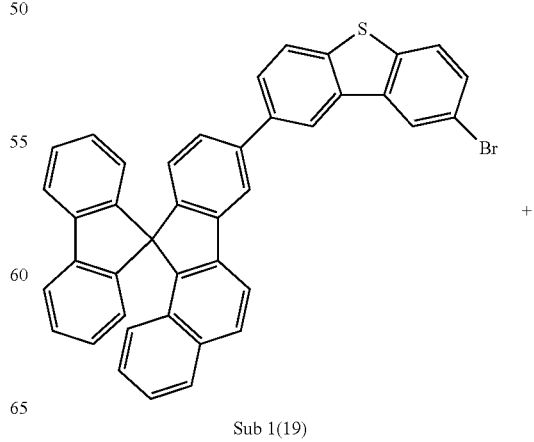

Sub 1(19)

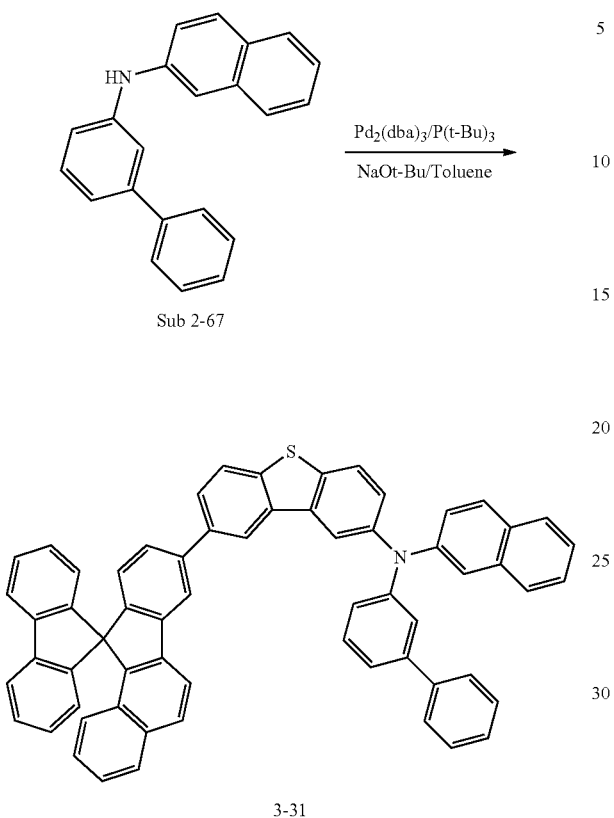

Sub 1(19) (15.1 g, 24 mmol) was dissolved in Toluene, Sub 2-67 (5.9 g, 20 mmol), Pd$_2$(dba)$_3$ (0.5 g, 0.6 mmol), P(t-Bu)$_3$ (0.2 g, 2 mmol), NaOt-Bu (5.8 g, 60 mmol) and toluene (300 mL) were added, the same procedure as described in the synthesis method of the 1-12 was carried out to obtain 12.5 g of the final product. (yield: 62%).

Synthesis Example of 3-32

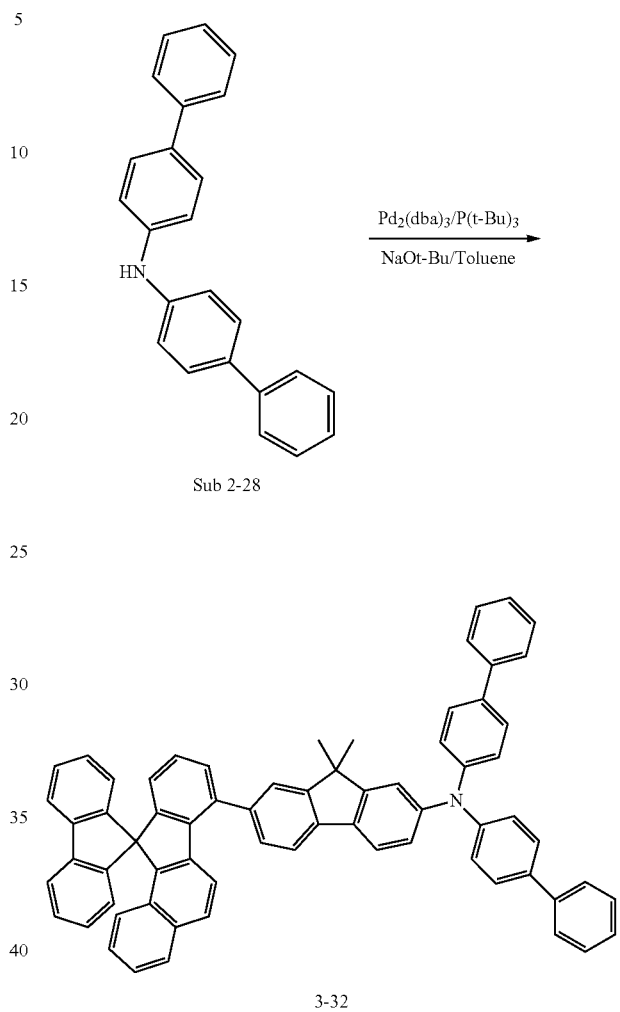

Sub 1(31) (15.3 g, 24 mmol) was dissolved in Toluene, Sub 2-28 (6.4 g, 20 mmol), Pd$_2$(dba)$_3$ (0.5 g, 0.6 mmol), P(t-Bu)$_3$ (0.2 g, 2 mmol), NaOt-Bu (5.8 g, 60 mmol) and toluene (300 mL) were added, the same procedure as described in the synthesis method of the 1-12 was carried out to obtain 13.5 g of the final product. (yield: 64%).

Synthesis Example of 3-40

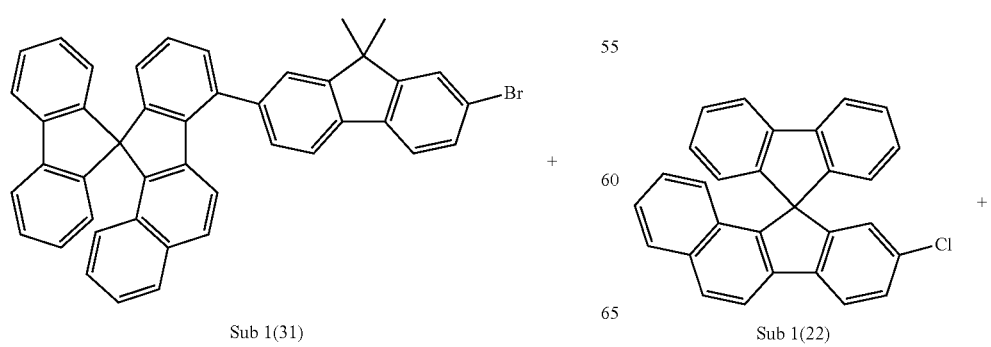

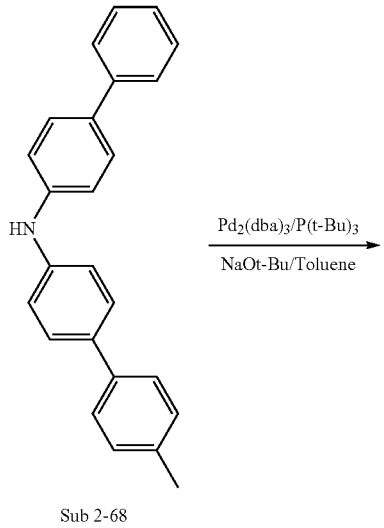

Sub 2-68

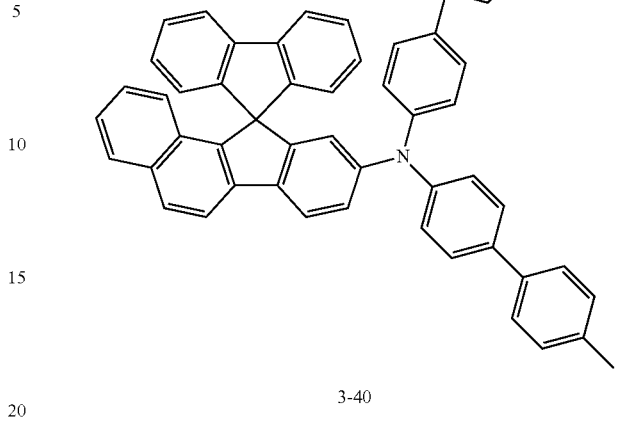

3-40

Sub 1(22) (9.6 g, 24 mmol) was dissolved in Toluene, Sub 2-68 (7.3 g, 20 mmol), $Pd_2(dba)_3$ (0.5 g, 0.6 mmol), $P(t-Bu)_3$ (0.2 g, 2 mmol), NaOt-Bu (5.8 g, 60 mmol) and toluene (300 mL) were added, the same procedure as described in the synthesis method of the 1-12 was carried out to obtain 10.2 g of the final product. (yield: 61%).

TABLE 3

| compound | FD-MS | compound | FD-MS |
|---|---|---|---|
| 1-1 | m/z = 533.21($C_{41}H_{27}N$ = 533.66) | 1-2 | m/z = 583.23($C_{45}H_{29}N$ = 583.72) |
| 1-3 | m/z = 583.23($C_{45}H_{29}N$ = 583.72) | 1-4 | m/z = 609.25($C_{47}H_{31}N$ = 609.76) |
| 1-5 | m/z = 609.25($C_{47}H_{31}N$ = 609.76) | 1-6 | m/z = 649.28($C_{50}H_{35}N$ = 649.82) |
| 1-7 | m/z = 773.31($C_{60}H_{39}N$ = 773.96) | 1-8 | m/z = 771.29($C_{60}H_{37}N$ = 771.94) |
| 1-9 | m/z = 821.31($C_{64}H_{39}N$ = 822.00) | 1-10 | m/z = 639.20($C_{47}H_{29}NS$ = 639.80) |
| 1-11 | m/z = 698.27($C_{53}H_{34}N_2$ = 698.85) | 1-12 | m/z = 699.26($C_{53}H_{33}NO$ = 699.84) |
| 1-13 | m/z = 686.27($C_{52}H_{34}N_2$ = 686.84) | 1-14 | m/z = 659.26($C_{51}H_{33}N$ = 659.81) |
| 1-15 | m/z = 765.25($C_{57}H_{35}NS$ = 765.96) | 1-16 | m/z = 801.34($C_{62}H_{43}N$ = 802.01) |
| 1-17 | m/z = 609.25($C_{47}H_{31}N$ = 609.76) | 1-18 | m/z = 659.26($C_{51}H_{33}N$ = 659.81) |
| 1-19 | m/z = 659.26($C_{51}H_{33}N$ = 659.81) | 1-20 | m/z = 685.28($C_{53}H_{35}N$ = 685.85) |
| 1-21 | m/z = 685.28($C_{53}H_{35}N$ = 685.85) | 1-22 | m/z = 725.31($C_{56}H_{39}N$ = 725.92) |
| 1-23 | m/z = 849.34($C_{66}H_{43}N$ = 850.05) | 1-24 | m/z = 847.32($C_{66}H_{41}N$ = 848.04) |
| 1-25 | m/z = 897.34($C_{70}H_{43}N$ = 898.10) | 1-26 | m/z = 715.23($C_{53}H_{33}NS$ = 715.90) |
| 1-27 | m/z = 774.30($C_{59}H_{38}N_2$ = 774.95) | 1-28 | m/z = 775.29($C_{59}H_{37}NO$ = 775.93) |
| 1-29 | m/z = 736.29($C_{56}H_{36}N_2$ = 736.90) | 1-30 | m/z = 709.28($C_{55}H_{35}N$ = 709.87) |
| 1-31 | m/z = 841.28($C_{63}H_{39}NS$ = 842.06) | 1-32 | m/z = 877.37($C_{68}H_{47}N$ = 878.11) |
| 1-33 | m/z = 761.31($C_{59}H_{39}N$ = 761.95) | 1-34 | m/z = 761.31($C_{59}H_{39}N$ = 761.95) |
| 1-35 | m/z = 762.30($C_{58}H_{38}N_2$ = 762.94) | 1-36 | m/z = 761.31($C_{59}H_{39}N$ = 761.95) |
| 1-37 | m/z = 730.34($C_{56}H_{34}D_5N$ = 730.95) | 1-39 | m/z = 739.32($C_{57}H_{41}N$ = 739.94) |
| 1-39 | m/z = 690.31($C_{53}H_{30}D_5N$ = 690.88) | 1-40 | m/z = 699.29($C_{54}H_{37}N$ = 699.88) |
| 2-1 | m/z = 533.21($C_{41}H_{27}N$ = 533.66) | 2-2 | m/z = 583.23($C_{45}H_{29}N$ = 583.72) |
| 2-3 | m/z = 583.23($C_{45}H_{29}N$ = 583.72) | 2-4 | m/z = 609.25($C_{47}H_{31}N$ = 609.76) |
| 2-5 | m/z = 609.25($C_{47}H_{31}N$ = 609.76) | 2-6 | m/z = 649.28($C_{50}H_{35}N$ = 649.82) |
| 2-7 | m/z = 773.31($C_{60}H_{39}N$ = 773.96) | 2-8 | m/z = 771.29($C_{60}H_{37}N$ = 771.94) |
| 2-9 | m/z = 821.31($C_{64}H_{39}N$ = 822.00) | 2-10 | m/z = 639.20($C_{47}H_{29}NS$ = 639.80) |
| 2-11 | m/z = 698.27($C_{53}H_{34}N_2$ = 698.85) | 2-12 | m/z = 699.26($C_{53}H_{33}NO$ = 699.84) |
| 2-13 | m/z = 686.27($C_{52}H_{34}N_2$ = 686.84) | 2-14 | m/z = 659.26($C_{51}H_{33}N$ = 659.81) |
| 2-15 | m/z = 765.25($C_{57}H_{35}NS$ = 765.96) | 2-16 | m/z = 801.34($C_{62}H_{43}N$ = 802.01) |
| 2-17 | m/z = 609.25($C_{47}H_{31}N$ = 609.76) | 2-18 | m/z = 659.26($C_{51}H_{33}N$ = 659.81) |
| 2-19 | m/z = 659.26($C_{51}H_{33}N$ = 659.81) | 2-20 | m/z = 685.28($C_{53}H_{35}N$ = 685.85) |
| 2-21 | m/z = 685.28($C_{53}H_{35}N$ = 685.85) | 2-22 | m/z = 725.31($C_{56}H_{39}N$ = 725.92) |
| 2-23 | m/z = 849.34($C_{66}H_{43}N$ = 850.05) | 2-24 | m/z = 847.32($C_{66}H_{41}N$ = 848.04) |
| 2-25 | m/z = 897.34($C_{70}H_{43}N$ = 898.10) | 2-26 | m/z = 715.23($C_{53}H_{33}NS$ = 715.90) |
| 2-27 | m/z = 774.30($C_{59}H_{38}N_2$ = 774.95) | 2-28 | m/z = 775.29($C_{59}H_{37}NO$ = 775.93) |
| 2-29 | m/z = 736.29($C_{56}H_{36}N_2$ = 736.90) | 2-30 | m/z = 709.28($C_{55}H_{35}N$ = 709.87) |
| 2-31 | m/z = 841.28($C_{63}H_{39}NS$ = 842.06) | 2-32 | m/z = 877.37($C_{68}H_{47}N$ = 878.11) |
| 2-33 | m/z = 761.31($C_{59}H_{39}N$ = 761.95) | 2-34 | m/z = 761.31($C_{59}H_{39}N$ = 761.95) |
| 2-35 | m/z = 762.30($C_{59}H_{38}N_2$ = 762.94) | 2-36 | m/z = 761.31($C_{59}H_{39}N$ = 761.95) |
| 2-37 | m/z = 730.34($C_{56}H_{34}D_5N$ = 730.95) | 2-39 | m/z = 739.32($C_{57}H_{41}N$ = 739.94) |
| 2-39 | m/z = 690.31($C_{53}H_{30}D_5N$ = 690.88) | 2-40 | m/z = 699.29($C_{54}H_{37}N$ = 699.88) |
| 3-1 | m/z = 533.21($C_{41}H_{27}N$ = 533.66) | 3-2 | m/z = 583.23($C_{45}H_{29}N$ = 583.72) |
| 3-3 | m/z = 583.23($C_{45}H_{29}N$ = 583.72) | 3-4 | m/z = 609.25($C_{47}H_{31}N$ = 609.76) |
| 3-5 | m/z = 609.25($C_{47}H_{31}N$ = 609.76) | 3-6 | m/z = 649.28($C_{50}H_{35}N$ = 649.82) |

TABLE 3-continued

| compound | FD-MS | compound | FD-MS |
|---|---|---|---|
| 3-7 | m/z = 773.31($C_{60}H_{39}N$ = 773.96) | 3-8 | m/z = 771.29($C_{60}H_{37}N$ = 771.94) |
| 3-9 | m/z = 821.31($C_{64}H_{39}N$ = 822.00) | 3-10 | m/z = 639.20($C_{47}H_{29}NS$ = 639.80) |
| 3-11 | m/z = 698.27($C_{53}H_{34}N$ = 698.85) | 3-12 | m/z = 699.26($C_{53}H_{33}NO$ = 699.84) |
| 3-13 | m/z = 686.27($C_{52}H_{34}N_2$ = 686.84) | 3-14 | m/z = 659.26($C_{51}H_{33}N$ = 659.81) |
| 3-15 | m/z = 765.25($C_{57}H_{35}NS$ = 765.96) | 3-16 | m/z = 801.34($C_{62}H_{43}N$ = 802.01) |
| 3-17 | m/z = 609.25($C_{47}H_{31}N$ = 609.76) | 3-18 | m/z = 659.26($C_{51}H_{33}N$ = 659.81) |
| 3-19 | m/z = 659.26($C_{51}H_{33}N$ = 659.81) | 3-20 | m/z = 685.28($C_{53}H_{35}N$ = 685.85) |
| 3-21 | m/z = 685.28($C_{53}H_{35}N$ = 685.85) | 3-22 | m/z = 725.31($C_{56}H_{39}N$ = 725.92) |
| 3-23 | m/z = 849.34($C_{66}H_{43}N$ = 850.05) | 3-24 | m/z = 847.32($C_{66}H_{41}N$ = 848.04) |
| 3-25 | m/z = 897.34($C_{70}H_{43}N$ = 898.10) | 3-26 | m/z = 715.23($C_{53}H_{33}NS$ = 715.90) |
| 3-29 | m/z = 774.30($C_{59}H_{38}N_2$ = 774.95) | 3-30 | m/z = 775.29($C_{59}H_{37}NO$ = 775.93) |
| 3-31 | m/z = 736.29($C_{56}H_{36}N_2$ = 736.90) | 3-32 | m/z = 709.28($C_{55}H_{35}N$ = 709.87) |
| 3-33 | m/z = 841.28($C_{63}H_{39}NS$ = 842.06) | 3-34 | m/z = 877.37($C_{68}H_{47}N$ = 878.11) |
| 3-35 | m/z = 761.31($C_{59}H_{39}N$ = 761.95) | 3-36 | m/z = 761.31($C_{59}H_{39}N$ = 761.95) |
| 3-37 | m/z = 762.30($C_{58}H_{38}N_2$ = 762.94) | 3-39 | m/z = 761.31($C_{59}H_{39}N$ = 761.95) |
| 3-39 | m/z = 730.34($C_{56}H_{34}D_5N$ =730.95) | 3-40 | m/z = 739.32($C_{57}H_{41}N$ = 739.94) |

Manufacture and Evaluation of Organic Electric Element

Example 1) Blue Organic Light Emitting Diode (Hole Transport Layer)

First, on an ITO layer (anode) formed on a glass substrate, $N^1$-naphthalen-2-yl)-$N^4$,$N^4$-bis(4-(naphthalen-2-yl(phenyl)amino)phenyl)-$N^1$-phenyl benzene-1,4-diamine (hereinafter will be abbreviated as 2-TNATA) was vacuum-deposited to form a hole injection layer with a thickness of 60 nm, and on the hole transport layer, the compound 1-1 of the present invention was vacuum deposited to form a hole transport layer with a thickness of 60 nm. Then, on the hole transport layer, an emitting layer with a thickness of 30 nm was deposited using 9,10-di(naphthalen-2-yl)anthracene, as a host doped with BD-052X (Idemitsukosan) as a dopant in a weight ratio of 96:4. (1,1'-bisphenyl)-4-olato)bis(2-methyl-8-quinolinolato)aluminum (hereinafter will be abbreviated as BAlq) was vacuum deposited to form a hole blocking layer with a thickness of 10 nm, and an electron transport layer was formed by vacuum-depositing tris(8-quinolinol) aluminum (hereinafter will be abbreviated as Alq3) to a thickness of 40 nm. After that, an alkali metal halide, LiF was vacuum deposited as an electron injection layer to a thickness of 0.2 nm, and Al was deposited to a thickness of 150 nm to form a cathode to manufacture an OLED.

To the OLEDs which were manufactured by examples and comparative examples, a forward bias direct current voltage was applied, and electroluminescent (EL) properties were measured using PR-650 of Photoresearch Co., and T95 life was measured using a life measuring apparatus manufactured by McScience Inc. with a reference luminance of 500 cd/m². In the following table, the manufacture of a device and the results of evaluation are shown.

Comparative Example A Comparative Example B
Comparative Example C Comparative Example D

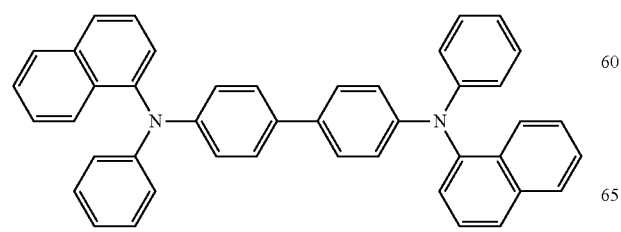

-continued

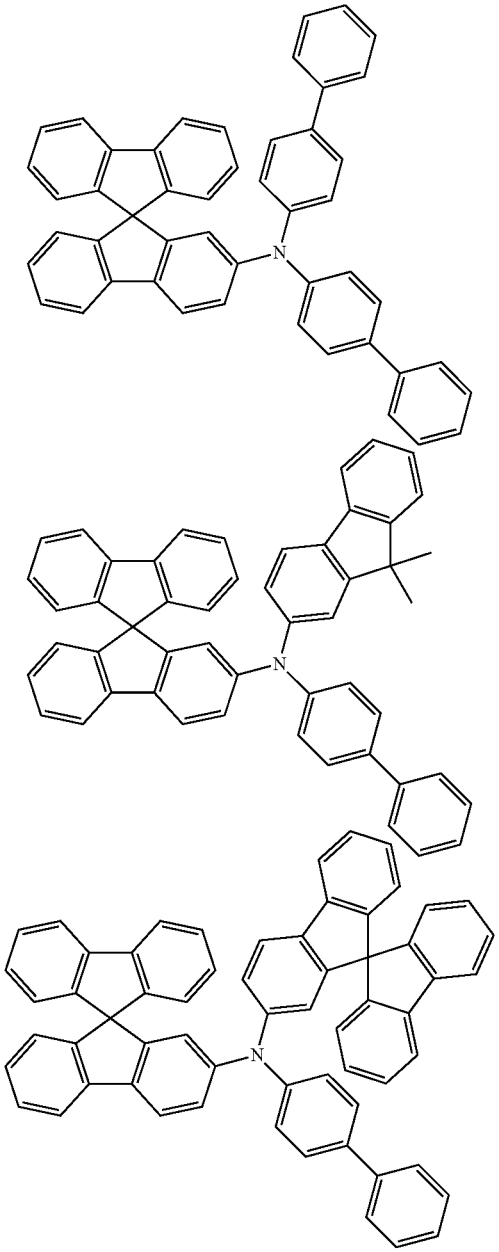

TABLE 4

| | compound | Voltage | Current Density | Brightness (cd/m2) | Efficiency | Lifetime T(95) | CIE (x, y) |
|---|---|---|---|---|---|---|---|
| comparative example(1) | compound (A) | 5.8 | 13.5 | 500.0 | 3.7 | 61.8 | (0.15, 0.13) |
| comparative example(2) | compound (B) | 5.3 | 10.6 | 500.0 | 4.7 | 92.7 | (0.14, 0.14) |
| comparative example(3) | compound (C) | 5.2 | 11.6 | 500.0 | 4.3 | 94.1 | (0.15, 0.14) |
| comparative example(3) | compound (C) | 5.4 | 10.5 | 500.0 | 4.8 | 94.3 | (0.15, 0.14) |
| example(1) | compound (1-1) | 4.6 | 9.9 | 500.0 | 5.1 | 126.1 | (0.15, 0.13) |
| example(2) | compound (1-2) | 4.8 | 9.4 | 500.0 | 5.3 | 124.4 | (0.15, 0.14) |
| example(3) | compound (1-3) | 4.7 | 9.5 | 500.0 | 5.3 | 139.2 | (0.15, 0.13) |
| example(4) | compound (1-4) | 4.6 | 10.0 | 500.0 | 5.0 | 131.5 | (0.14, 0.14) |
| example(5) | compound (1-5) | 4.6 | 9.9 | 500.0 | 5.1 | 122.3 | (0.14, 0.14) |
| example(6) | compound (1-6) | 4.8 | 9.6 | 500.0 | 5.2 | 129.2 | (0.14, 0.14) |
| example(7) | compound (1-7) | 4.7 | 9.6 | 500.0 | 5.2 | 132.0 | (0.15, 0.13) |
| example(8) | compound (1-8) | 4.7 | 9.8 | 500.0 | 5.1 | 123.0 | (0.15, 0.14) |
| example(9) | compound (1-9) | 4.5 | 9.6 | 500.0 | 5.2 | 137.0 | (0.15, 0.14) |
| example(10) | compound (1-10) | 4.5 | 10.0 | 500.0 | 5.0 | 139.5 | (0.15, 0.13) |
| example(11) | compound (1-11) | 4.8 | 9.8 | 500.0 | 5.1 | 123.0 | (0.14, 0.14) |
| example(12) | compound (1-12) | 4.5 | 9.8 | 500.0 | 5.1 | 137.4 | (0.15, 0.14) |
| example(13) | compound (1-13) | 4.8 | 9.8 | 500.0 | 5.1 | 125.1 | (0.15, 0.14) |
| example(14) | compound (1-14) | 4.7 | 9.9 | 500.0 | 5.1 | 135.5 | (0.14, 0.14) |
| example(15) | compound (1-15) | 4.8 | 9.5 | 500.0 | 5.3 | 135.7 | (0.15, 0.13) |
| example(16) | compound (1-16) | 4.7 | 9.5 | 500.0 | 5.3 | 134.5 | (0.15, 0.16) |
| example(17) | compound (1-17) | 4.7 | 9.6 | 500.0 | 5.2 | 134.3 | (0.15, 0.14) |
| example(18) | compound (1-18) | 4.6 | 9.9 | 500.0 | 5.0 | 127.3 | (0.15, 0.13) |
| example(19) | compound (1-19) | 4.6 | 9.9 | 500.0 | 5.0 | 130.4 | (0.14, 0.14) |
| example(20) | compound (1-20) | 4.6 | 9.9 | 500.0 | 5.0 | 139.8 | (0.15, 0.14) |
| example(21) | compound (1-21) | 4.7 | 9.5 | 500.0 | 5.3 | 121.0 | (0.15, 0.13) |
| example(22) | compound (1-22) | 4.6 | 9.8 | 500.0 | 5.1 | 120.3 | (0.14, 0.14) |
| example(23) | compound (1-23) | 4.8 | 9.7 | 500.0 | 5.1 | 137.0 | (0.14, 0.14) |
| example(24) | compound (1-24) | 4.5 | 9.5 | 500.0 | 5.3 | 138.9 | (0.15, 0.13) |
| example(25) | compound (1-25) | 4.6 | 9.8 | 500.0 | 5.1 | 130.3 | (0.15, 0.14) |
| example(26) | compound (1-26) | 4.7 | 9.5 | 500.0 | 5.2 | 126.6 | (0.14, 0.14) |
| example(27) | compound (1-27) | 4.6 | 9.9 | 500.0 | 5.0 | 127.8 | (0.15, 0.14) |
| example(28) | compound (1-28) | 4.7 | 9.8 | 500.0 | 5.1 | 137.0 | (0.15, 0.14) |
| example(29) | compound (1-29) | 4.8 | 9.5 | 500.0 | 5.3 | 131.3 | (0.15, 0.13) |
| example(30) | compound (1-30) | 4.6 | 9.7 | 500.0 | 5.1 | 120.7 | (0.14, 0.14) |
| example(31) | compound (1-31) | 4.6 | 9.6 | 500.0 | 5.2 | 125.8 | (0.14, 0.14) |
| example(32) | compound (1-32) | 4.6 | 9.8 | 500.0 | 5.1 | 121.2 | (0.14, 0.14) |
| example(33) | compound (1-33) | 4.7 | 9.6 | 500.0 | 5.2 | 122.4 | (0.15, 0.13) |
| example(34) | compound (1-34) | 4.7 | 9.9 | 500.0 | 5.1 | 131.5 | (0.15, 0.14) |

TABLE 4-continued

| | compound | Voltage | Current Density | Brightness (cd/m2) | Efficiency | Lifetime T(95) | CIE (x, y) |
|---|---|---|---|---|---|---|---|
| example(35) | compound (1-35) | 4.6 | 9.7 | 500.0 | 5.1 | 139.6 | (0.15, 0.14) |
| example(36) | compound (1-36) | 4.7 | 9.9 | 500.0 | 5.1 | 132.5 | (0.15, 0.13) |
| example(37) | compound (1-37) | 4.6 | 9.9 | 500.0 | 5.0 | 139.9 | (0.15, 0.14) |
| example(38) | compound (1-38) | 4.6 | 9.7 | 500.0 | 5.1 | 134.2 | (0.15, 0.13) |
| example(39) | compound (1-39) | 4.5 | 9.5 | 500.0 | 5.3 | 121.7 | (0.14, 0.14) |
| example(40) | compound (1-40) | 4.7 | 9.7 | 500.0 | 5.2 | 129.0 | (0.14, 0.14) |
| example(41) | compound (2-1) | 4.6 | 9.5 | 500.0 | 5.3 | 133.9 | (0.15, 0.14) |
| example(42) | compound (2-2) | 4.7 | 9.9 | 500.0 | 5.1 | 120.3 | (0.15, 0.14) |
| example(43) | compound (2-3) | 4.6 | 9.5 | 500.0 | 5.3 | 125.3 | (0.14, 0.14) |
| example(44) | compound (2-4) | 4.8 | 9.9 | 500.0 | 5.0 | 129.1 | (0.15, 0.14) |
| example(45) | compound (2-5) | 4.6 | 9.8 | 500.0 | 5.1 | 128.9 | (0.14, 0.14) |
| example(46) | compound (2-6) | 4.6 | 9.8 | 500.0 | 5.1 | 124.6 | (0.15, 0.15) |
| example(47) | compound (2-7) | 4.6 | 9.9 | 500.0 | 5.0 | 130.2 | (0.15, 0.13) |
| example(48) | compound (2-8) | 4.5 | 9.4 | 500.0 | 5.3 | 127.9 | (0.15, 0.14) |
| example(49) | compound (2-9) | 4.7 | 9.9 | 500.0 | 5.0 | 123.6 | (0.15, 0.16) |
| example(50) | compound (2-10) | 4.5 | 9.9 | 500.0 | 5.1 | 137.3 | (0.15, 0.14) |
| example(51) | compound (2-11) | 4.7 | 10.0 | 500.0 | 5.0 | 129.8 | (0.14, 0.14) |
| example(52) | compound (2-12) | 4.5 | 10.0 | 500.0 | 5.0 | 122.9 | (0.14, 0.14) |
| example(53) | compound (2-13) | 4.7 | 9.5 | 500.0 | 5.3 | 133.8 | (0.15, 0.13) |
| example(54) | compound (2-14) | 4.7 | 10.0 | 500.0 | 5.0 | 139.8 | (0.15, 0.15) |
| example(55) | compound (2-15) | 4.6 | 9.9 | 500.0 | 5.1 | 123.8 | (0.15, 0.16) |
| example(56) | compound (2-16) | 4.6 | 9.8 | 500.0 | 5.1 | 136.1 | (0.15, 0.14) |
| example(57) | compound (2-17) | 4.6 | 9.9 | 500.0 | 5.0 | 126.2 | (0.15, 0.14) |
| example(58) | compound (2-18) | 4.7 | 9.9 | 500.0 | 5.1 | 122.7 | (0.15, 0.15) |
| example(59) | compound (2-19) | 4.7 | 9.9 | 500.0 | 5.0 | 136.4 | (0.15, 0.14) |
| example(60) | compound (2-20) | 4.7 | 9.9 | 500.0 | 5.1 | 121.5 | (0.15, 0.14) |
| example(61) | compound (2-21) | 4.7 | 9.9 | 500.0 | 5.1 | 124.9 | (0.14, 0.14) |
| example(62) | compound (2-22) | 4.5 | 9.9 | 500.0 | 5.1 | 129.1 | (0.15, 0.14) |
| example(63) | compound (2-23) | 4.5 | 9.8 | 500.0 | 5.1 | 132.2 | (0.15, 0.13) |
| example(64) | compound (2-24) | 4.6 | 9.6 | 500.0 | 5.2 | 139.6 | (0.15, 0.14) |
| example(65) | compound (2-25) | 4.6 | 10.0 | 500.0 | 5.0 | 130.3 | (0.15, 0.14) |
| example(66) | compound (2-26) | 4.7 | 9.7 | 500.0 | 5.2 | 122.3 | (0.15, 0.14) |
| example(67) | compound (2-27) | 4.6 | 9.7 | 500.0 | 5.2 | 135.0 | (0.15, 0.13) |
| example(68) | compound (2-28) | 4.8 | 9.4 | 500.0 | 5.3 | 127.9 | (0.15, 0.13) |
| example(69) | compound (2-29) | 4.5 | 9.4 | 500.0 | 5.3 | 133.9 | (0.15, 0.14) |
| example(70) | compound (2-30) | 4.7 | 9.7 | 500.0 | 5.1 | 124.5 | (0.15, 0.15) |
| example(71) | compound (2-31) | 4.5 | 9.7 | 500.0 | 5.1 | 129.3 | (0.15, 0.15) |
| example(72) | compound (2-32) | 4.7 | 9.5 | 500.0 | 5.3 | 135.4 | (0.15, 0.14) |

TABLE 4-continued

| | compound | Voltage | Current Density | Brightness (cd/m2) | Efficiency | Lifetime T(95) | CIE (x, y) |
|---|---|---|---|---|---|---|---|
| example(73) | compound (2-33) | 4.7 | 9.6 | 500.0 | 5.2 | 136.7 | (0.15, 0.14) |
| example(74) | compound (2-34) | 4.6 | 9.4 | 500.0 | 5.3 | 131.4 | (0.15, 0.16) |
| example(75) | compound (2-35) | 4.8 | 9.5 | 500.0 | 5.3 | 130.6 | (0.14, 0.14) |
| example(76) | compound (2-36) | 4.6 | 9.6 | 500.0 | 5.2 | 126.7 | (0.15, 0.13) |
| example(77) | compound (2-37) | 4.8 | 9.8 | 500.0 | 5.1 | 133.4 | (0.15, 0.14) |
| example(78) | compound (2-38) | 4.6 | 9.9 | 500.0 | 5.0 | 120.7 | (0.15, 0.13) |
| example(79) | compound (2-39) | 4.7 | 9.8 | 500.0 | 5.1 | 121.6 | (0.14, 0.14) |
| example(80) | compound (2-40) | 4.7 | 9.8 | 500.0 | 5.1 | 130.8 | (0.14, 0.14) |
| example(81) | compound (3-1) | 4.6 | 9.4 | 500.0 | 5.3 | 130.7 | (0.15, 0.13) |
| example(82) | compound (3-2) | 4.6 | 9.6 | 500.0 | 5.2 | 133.0 | (0.15, 0.14) |
| example(83) | compound (3-3) | 4.5 | 9.5 | 500.0 | 5.2 | 124.5 | (0.15, 0.14) |
| example(84) | compound (3-4) | 4.5 | 9.5 | 500.0 | 5.3 | 132.9 | (0.15, 0.15) |
| example(85) | compound (3-5) | 4.7 | 9.7 | 500.0 | 5.1 | 136.0 | (0.15, 0.13) |
| example(86) | compound (3-6) | 4.6 | 10.0 | 500.0 | 5.0 | 126.3 | (0.15, 0.14) |
| example(87) | compound (3-7) | 4.6 | 9.6 | 500.0 | 5.2 | 136.7 | (0.15, 0.13) |
| example(88) | compound (3-8) | 4.8 | 9.6 | 500.0 | 5.2 | 124.9 | (0.15, 0.14) |
| example(89) | compound (3-9) | 4.7 | 9.5 | 500.0 | 5.3 | 127.1 | (0.15, 0.14) |
| example(90) | compound (3-10) | 4.6 | 9.9 | 500.0 | 5.1 | 137.2 | (0.15, 0.14) |
| example(91) | compound (3-11) | 4.8 | 9.5 | 500.0 | 5.3 | 135.2 | (0.15, 0.14) |
| example(92) | compound (3-12) | 4.6 | 9.8 | 500.0 | 5.1 | 120.1 | (0.14, 0.14) |
| example(93) | compound (3-13) | 4.6 | 9.7 | 500.0 | 5.2 | 135.6 | (0.14, 0.14) |
| example(94) | compound (3-14) | 4.5 | 9.8 | 500.0 | 5.1 | 140.0 | (0.15, 0.14) |
| example(95) | compound (3-15) | 4.5 | 9.9 | 500.0 | 5.1 | 133.0 | (0.15, 0.13) |
| example(96) | compound (3-16) | 4.7 | 9.7 | 500.0 | 5.1 | 125.8 | (0.15, 0.15) |
| example(97) | compound (3-17) | 4.8 | 9.8 | 500.0 | 5.1 | 136.0 | (0.15, 0.13) |
| example(98) | compound (3-18) | 4.7 | 9.7 | 500.0 | 5.2 | 121.0 | (0.15, 0.14) |
| example(99) | compound (3-19) | 4.7 | 9.7 | 500.0 | 5.2 | 128.4 | (0.15, 0.14) |
| example(100) | compound (3-20) | 4.8 | 9.5 | 500.0 | 5.3 | 125.8 | (0.14, 0.14) |
| example(101) | compound (3-21) | 4.6 | 9.6 | 500.0 | 5.2 | 126.8 | (0.15, 0.13) |
| example(102) | compound (3-22) | 4.5 | 9.4 | 500.0 | 5.3 | 121.0 | (0.15, 0.14) |
| example(103) | compound (3-23) | 4.7 | 9.8 | 500.0 | 5.1 | 126.3 | (0.15, 0.14) |
| example(104) | compound (3-24) | 4.6 | 9.8 | 500.0 | 5.1 | 129.9 | (0.14, 0.14) |
| example(105) | compound (3-25) | 4.7 | 9.7 | 500.0 | 5.2 | 133.4 | (0.15, 0.16) |
| example(106) | compound (3-26) | 4.7 | 9.5 | 500.0 | 5.2 | 129.1 | (0.15, 0.13) |
| example(107) | compound (3-27) | 4.8 | 9.6 | 500.0 | 5.2 | 120.1 | (0.15, 0.14) |
| example(108) | compound (3-28) | 4.5 | 9.9 | 500.0 | 5.1 | 132.0 | (0.15, 0.14) |
| example(109) | compound (3-29) | 4.8 | 9.8 | 500.0 | 5.1 | 120.6 | (0.15, 0.14) |
| example(110) | compound (3-30) | 4.5 | 9.8 | 500.0 | 5.1 | 139.0 | (0.15, 0.16) |

TABLE 4-continued

|  | compound | Voltage | Current Density | Brightness (cd/m2) | Efficiency | Lifetime T(95) | CIE (x, y) |
|---|---|---|---|---|---|---|---|
| example(111) | compound (3-31) | 4.6 | 9.6 | 500.0 | 5.2 | 127.8 | (0.14, 0.14) |
| example(112) | compound (3-32) | 4.7 | 9.7 | 500.0 | 5.2 | 127.1 | (0.15, 0.14) |
| example(113) | compound (3-33) | 4.6 | 9.8 | 500.0 | 5.1 | 133.6 | (0.14, 0.14) |
| example(114) | compound (3-34) | 4.6 | 9.4 | 500.0 | 5.3 | 138.7 | (0.15, 0.15) |
| example(115) | compound (3-35) | 4.7 | 9.7 | 500.0 | 5.1 | 136.4 | (0.15, 0.13) |
| example(116) | compound (3-36) | 4.7 | 9.6 | 500.0 | 5.2 | 123.8 | (0.15, 0.14) |
| example(117) | compound (3-37) | 4.7 | 9.7 | 500.0 | 5.1 | 138.8 | (0.15, 0.14) |
| example(118) | compound (3-38) | 4.8 | 9.9 | 500.0 | 5.0 | 138.6 | (0.15, 0.13) |
| example(119) | compound (3-39) | 4.6 | 9.5 | 500.0 | 5.2 | 123.1 | (0.14, 0.14) |
| example(120) | compound (3-40) | 4.5 | 9.8 | 500.0 | 5.1 | 124.9 | (0.14, 0.14) |

As it is apparent from the results of Table 4, when the compound of the present invention is used as hole transport layer, the driving voltage and life span can be remarkably improved.

In other words, Comparative Examples 2 to 4 using Comparative Compounds B to D in which tertiary amines were substituted with spirobifluorene as a hole transport layer showed better results in terms of driving voltage, efficiency, and life span than Comparative Example 1 using NPB as a hole transport layer, and Examples 1 to 120 using the compound of the present invention substituted the spirobifluorene fused to the tertiary amine showed a slightly improved efficiency but a remarkably improved driving voltage and life span than Comparative Examples 2 to 4.

[Hole injection: 1 mA/cm$^2$]

TABLE 5

TABLE 5-continued

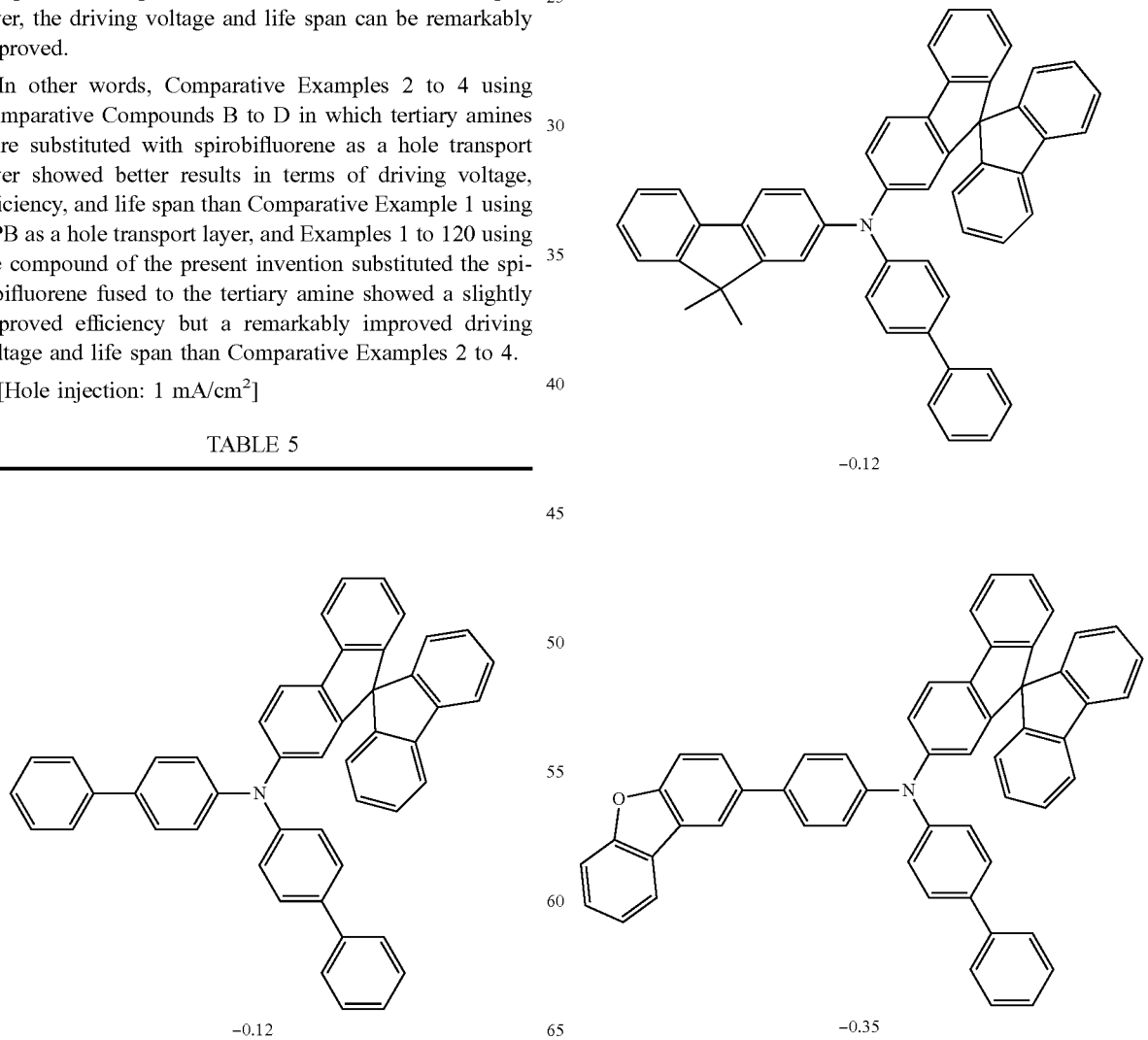

TABLE 5-continued
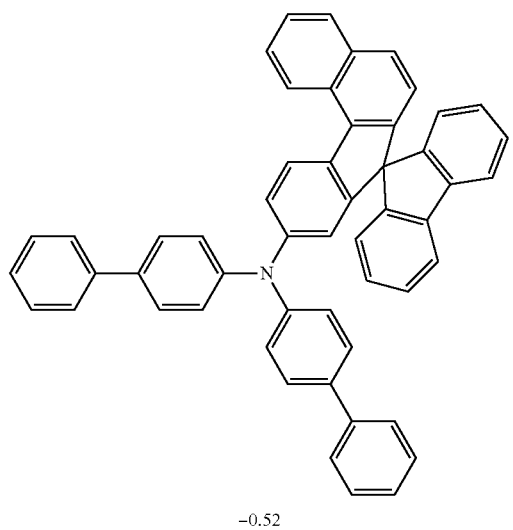
−0.52
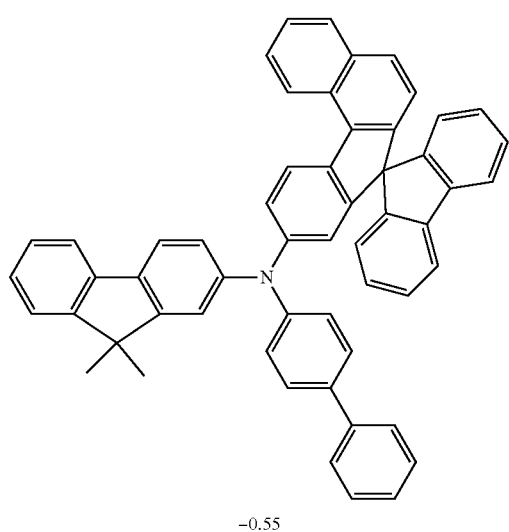
−0.55
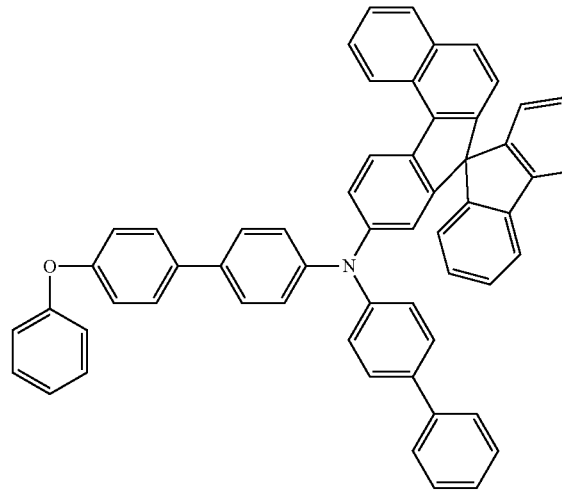
−0.58
[Hole mobility: 100 mA/cm$^2$]
TABLE 6
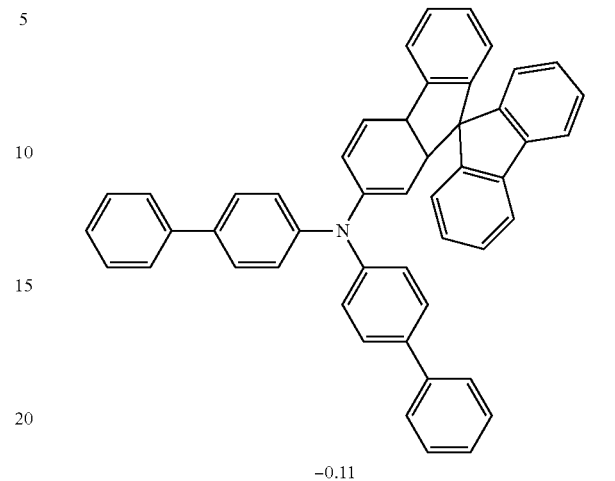
−0.11
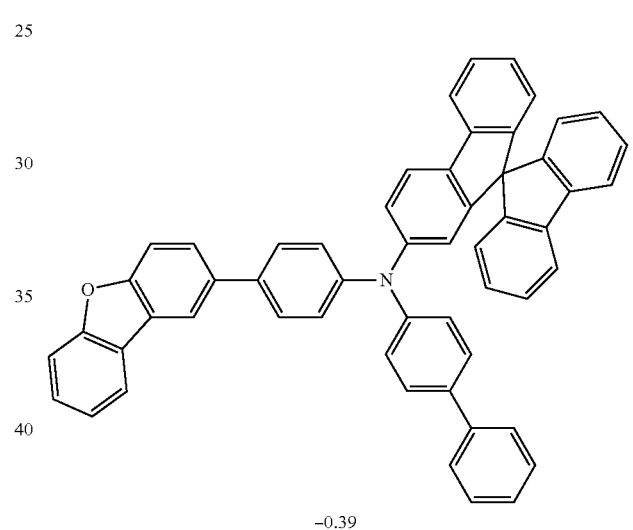
−0.39
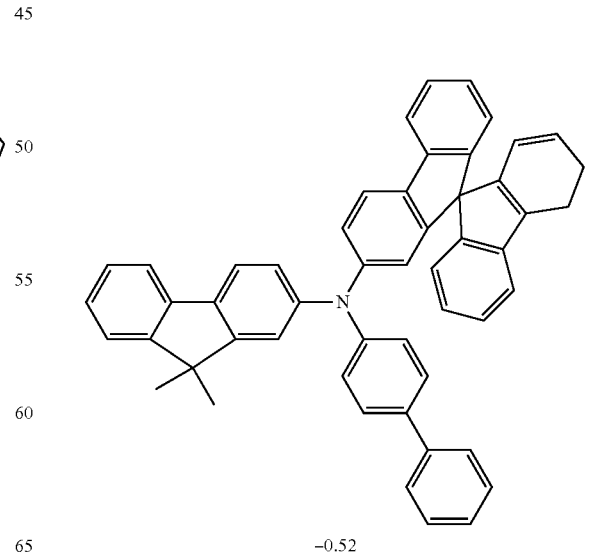
−0.52

TABLE 6-continued

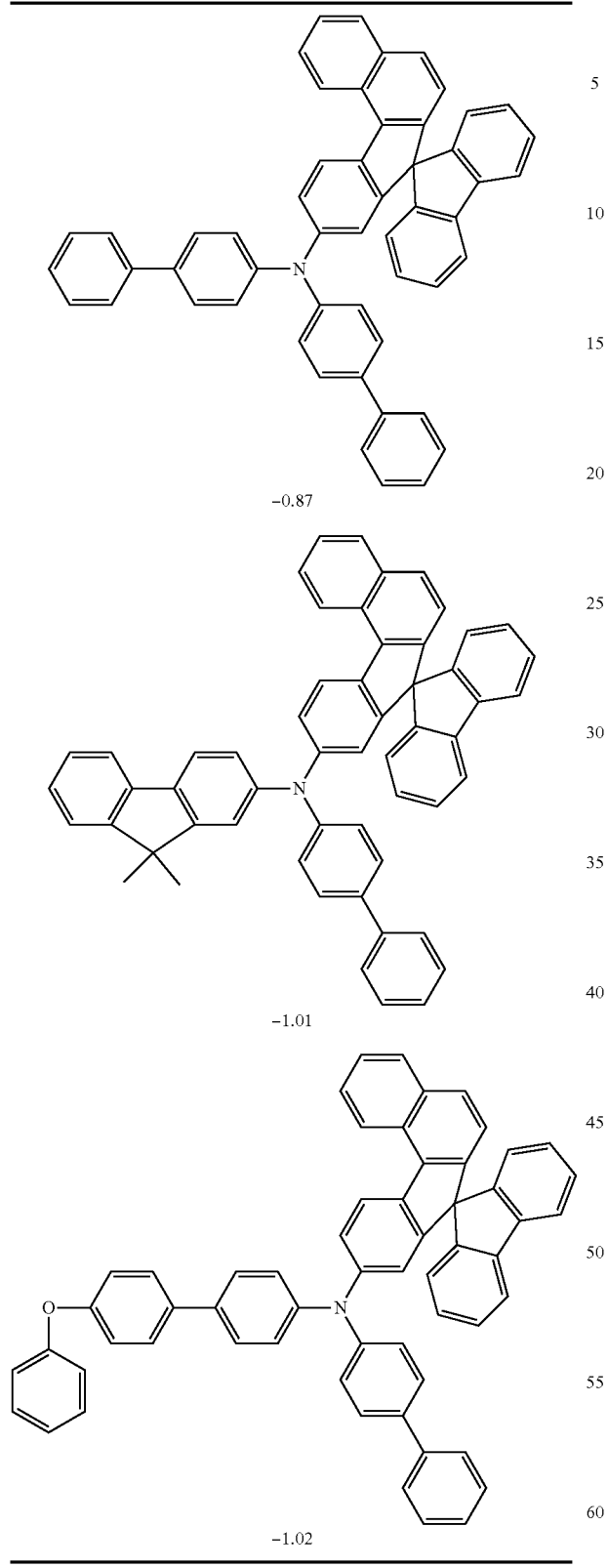

−0.87

−1.01

−1.02

As a result of the experiment, evaluation of Hole injection and mobility of the compound, compounds of the present invention wherein the fused spirofluorene is substituted was much higher in hole injection and was faster in mobility than Comparative compounds B to D substituted with spirobifluorene. Therefore, as the hole injection and mobility abilities are improved, deterioration is reduced at the ITO and HTL interface, and the life span of the element is improved. As more holes move into the emitting layer, the charge balance in the emitting layer of holes and electrons is increased and light emission is well performed inside the emitting layer rather than at the interface of the hole transport layer and thereby maximizing the driving voltage, efficiency and lifetime. This suggests that the physical properties of the compound and the result of the element may vary significantly as the spirofluorene is fused.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment.

The scope of the present invention shall be construed on the basis of the accompanying claims, and it shall be construed that all of the technical ideas included within the scope equivalent to the claims belong to the present invention.

What is claimed is:
1. A compound represented by Formula (1):

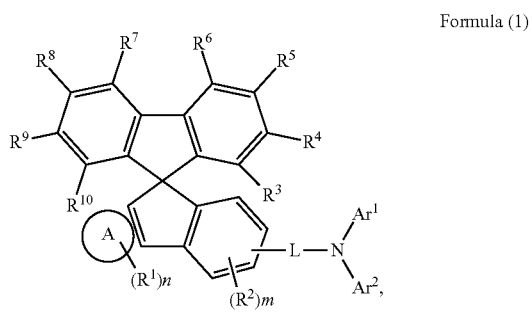

Formula (1)

wherein
1) $R^1$, $R^2$, $R^3$, $R^4$, $R^5$, $R^6$, $R^7$, $R^8$, $R^9$ and $R^{10}$ are each independently selected from hydrogen; deuterium; a halogen; a $C_6$-$C_{30}$ aryl group; a fluorenyl group; a $C_2$-$C_{30}$ heterocyclic group including at least one hetero atom of O, N, S, Si and P; a fused ring group of a $C_3$-$C_{30}$ aliphatic ring and a $C_6$-$C_{30}$ aromatic ring; a $C_1$-$C_{20}$ alkyl group; a $C_2$-$C_{20}$ alkenyl group; a $C_2$-$C_{20}$ alkynyl group; a $C_1$-$C_{20}$ alkoxyl group; and a $C_6$-$C_{20}$ aryloxy group,
2) A is an aryl group of $C_{10}$,
3) L is selected from the group consisting of a single bond; a $C_6$-$C_{30}$ arylene group; a fluorenylene group; a fused ring group of a $C_3$-$C_{30}$ aliphatic ring and a $C_6$-$C_{30}$ aromatic ring; and a $C_2$-$C_{30}$ heterocyclic group including at least one hetero atom of O, N, S, Si and P,
4) $Ar^1$, $Ar^2$ are each independently selected from the group consisting of a $C_6$-$C_{30}$ aryl group; a fluorenyl group; a $C_2$-$C_{30}$ heterocyclic group including at least one hetero atom of O, N, S, Si and P; and a fused ring group of a $C_3$-$C_{30}$ aliphatic ring and a $C_6$-$C_{30}$ aromatic ring;

5) m is an integer of 0 to 3,
6) n is an integer of 0 to 6,
wherein, each of the aryl group, fluorenyl group, arylene group, heterocyclic group, and fused ring group may be substituted by one or more of the substituents selected from the group consisting of deuterium; halogen; a $C_1$-$C_{20}$ alkylthio group; a $C_1$-$C_{20}$ alkoxyl group; a $C_1$-$C_{20}$ alkyl group; a $C_2$-$C_{20}$ alkenyl group; a $C_2$-$C_{20}$ alkynyl group; a $C_6$-$C_{20}$ aryl group; a $C_6$-$C_{20}$ aryl group substituted by deuterium; fluorenyl group; a $C_2$-$C_{20}$ heterocyclic group; a $C_3$-$C_{20}$ cycloalkyl group; a $C_7$-$C_{20}$ arylalkyl group, and a $C_8$-$C_{20}$ arylalkenyl group, and also may combine to each other to form a ring, wherein the 'ring' means an aliphatic ring having 3 to 30 carbon atoms, or an aromatic ring having 6 to 30 carbon atoms, or a hetero ring having 2 to 30 carbon atoms, or a fused ring formed by combination of the groups, and includes a saturated or unsaturated ring.

2. The compound of claim 1, wherein Formula (1) is represented by Formula (2), Formula (3), or Formula (4):

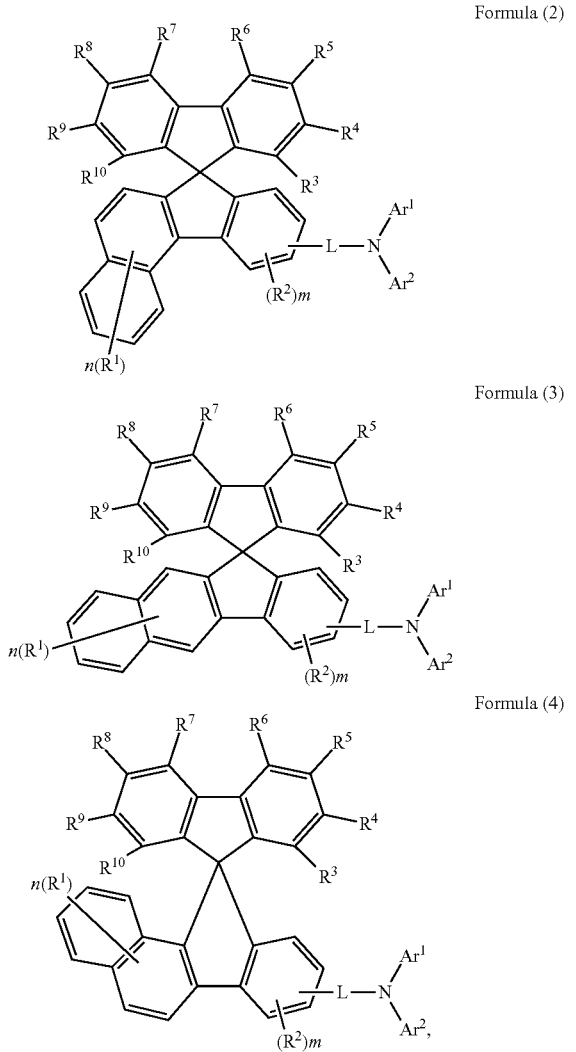

wherein
$R^1$, $R^2$, $R^3$, $R^4$, $R^5$, $R^6$, $R^7$, $R^8$, $R^9$, $R^{10}$, L, $Ar^1$, $Ar^2$, n and m are the same as defined for Formula (1) in claim 1.

3. The compound of claim 1, wherein Formula (1) is represented by Formula (5):

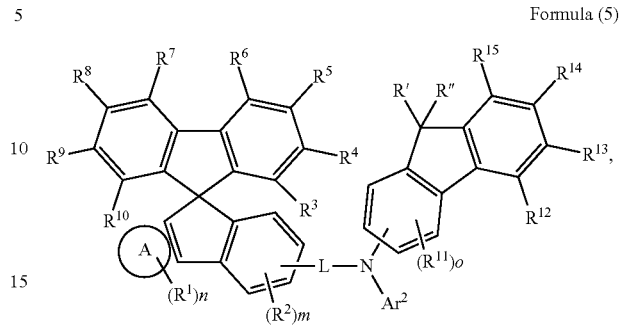

wherein
1) $R^1$, $R^2$, $R^3$, $R^4$, $R^5$, $R^6$, $R^7$, $R^8$, $R^9$, $R^{10}$, A, L, $Ar^2$, n and m are the same as defined in Formula (1) in claim 1,
2) R', R" are each selected from the group consisting of hydrogen; a $C_6$-$C_{30}$ aryl group; a $C_2$-$C_{30}$ heterocyclic group including at least one hetero atom of O, N, S, Si and P; a fused ring group of a $C_3$-$C_{30}$ aliphatic ring and a $C_6$-$C_{30}$ aromatic ring; a $C_1$-$C_{20}$ alkyl group; a $C_2$-$C_{20}$ alkenyl group, or R' and R" may combine each other and form a spiro ring,
3) o is an integer of 0 to 3,
4) $R^{11}$, $R^{12}$, $R^{13}$, $R^{14}$ and $R^{15}$ are each independently selected from hydrogen; deuterium; a halogen; a $C_6$-$C_{30}$ aryl group; a fluorenyl group; a $C_2$-$C_{30}$ heterocyclic group including at least one hetero atom of O, N, S, Si and P; a fused ring group of a $C_3$-$C_{30}$ aliphatic ring and a $C_6$-$C_{30}$ aromatic ring; a $C_1$-$C_{20}$ alkyl group; a $C_2$-$C_{20}$ alkenyl group; a $C_2$-$C_{20}$ alkynyl group; a $C_1$-$C_{30}$ alkoxyl group; and a $C_6$-$C_{30}$ aryloxy group; or two adjacent $R^{11}$s, $R^{12}$ and $R^{13}$, $R^{13}$ and $R^{14}$, $R^{14}$ and $R^{15}$ may combine to form an aromatic or a heterocyclic ring.

4. The compound of claim 1, wherein Formula (1) is represented by Formula (6):

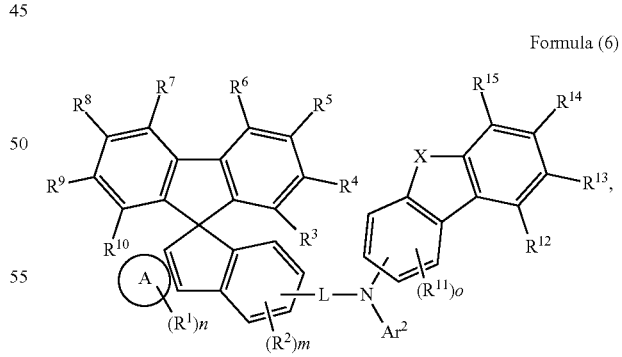

wherein
1) $R^1$, $R^2$, $R^3$, $R^4$, $R^5$, $R^6$, $R^7$, $R^8$, $R^9$, $R^{10}$, A, L, $Ar^2$, n and m are the same as defined for Formula (1) in claim 1,
2) o is an integer of 0 to 3,
3) $R^{11}$, $R^{12}$, $R^{13}$, $R^{13}$, $R^{14}$ and $R^{15}$ are each independently selected from hydrogen; deuterium; a halogen; a $C_6$-$C_{30}$ aryl group; a fluorenyl group; a $C_2$-$C_{30}$ heterocyclic group including at least one hetero atom of O, N, S, Si and P; a fused ring group of a $C_3$-$C_{30}$ aliphatic ring and a $C_6$-$C_{30}$ aromatic ring; a $C_1$-$C_{20}$ alkyl group; a $C_2$-$C_{20}$ alkenyl group; a $C_2$-$C_{20}$ alkynyl group; a $C_1$-$C_{30}$ alkoxyl group; and a $C_6$-$C_{30}$ aryloxy group; or two adjacent $R^{11}$s, $R^{12}$ and $R^{13}$, $R^{13}$ and $R^{14}$, $R^{14}$ and $R^{15}$ may combine to form an aromatic or a heterocyclic ring, and 4) X is O or S.

5. A compound selected from the group consisting of the following compounds:

1-1

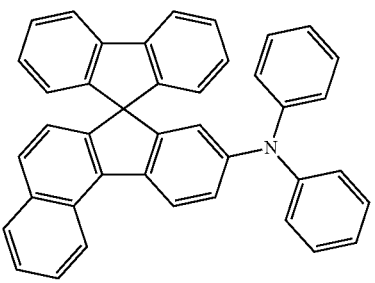

1-2

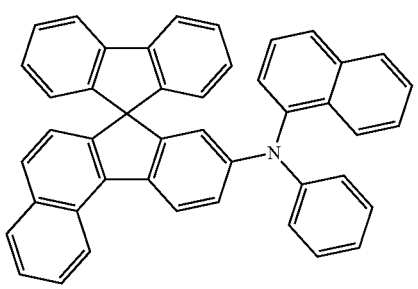

1-3

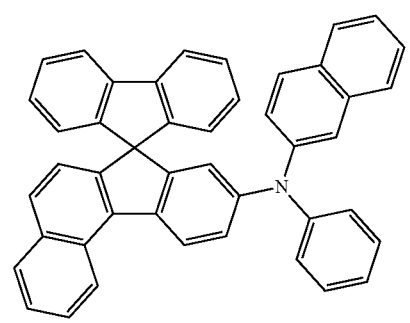

1-4

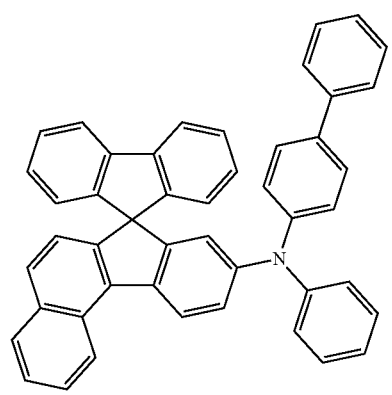

1-5

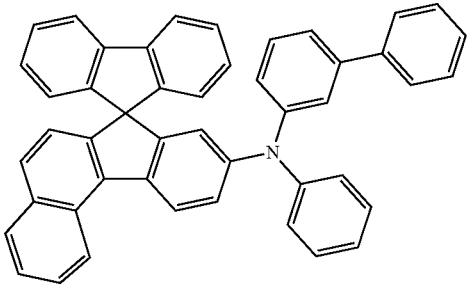

1-6

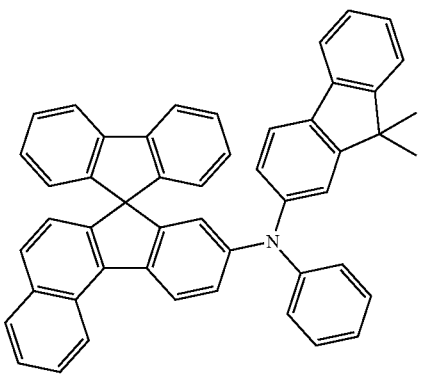

1-7

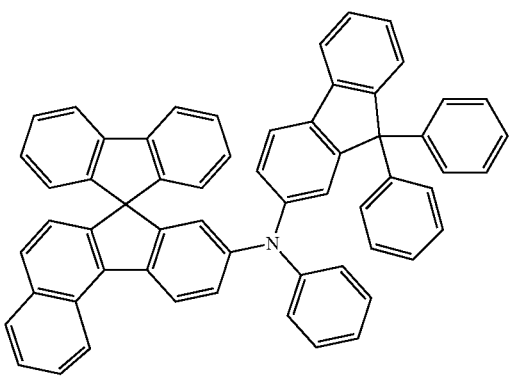

1-8

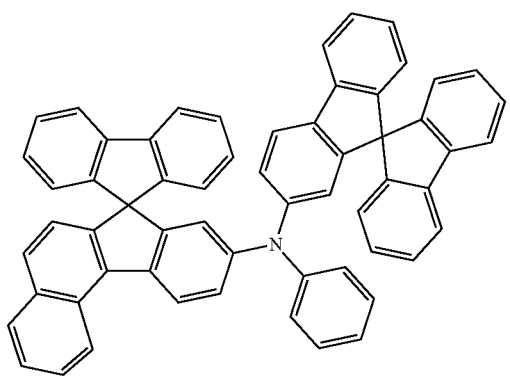

1-9
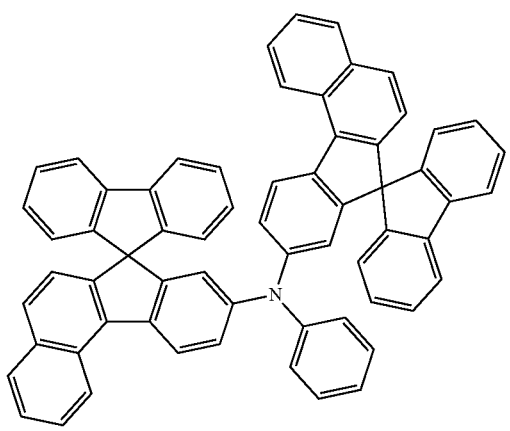
1-10
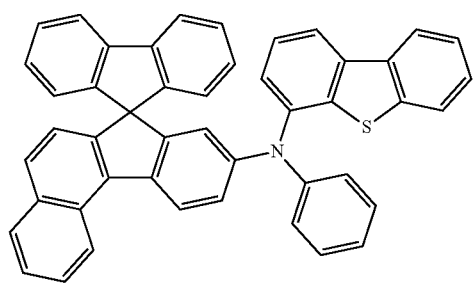
1-11
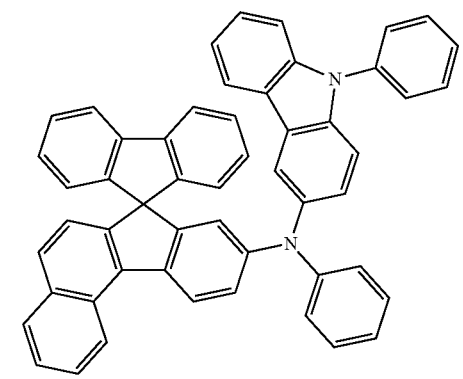
1-12
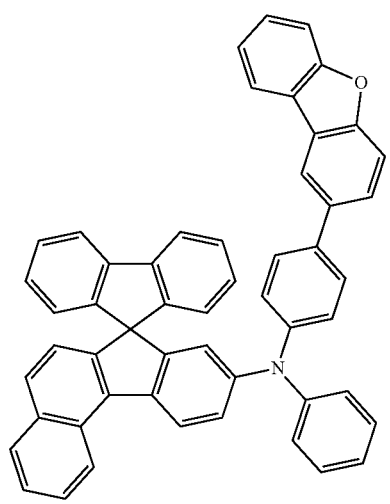
1-13
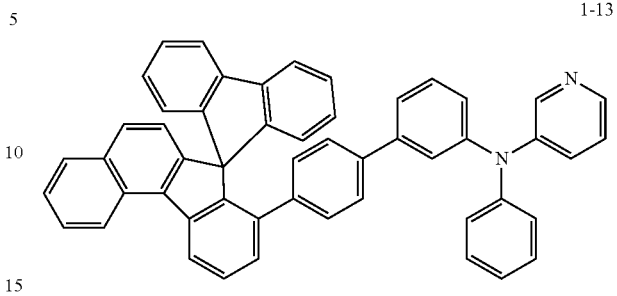
1-14
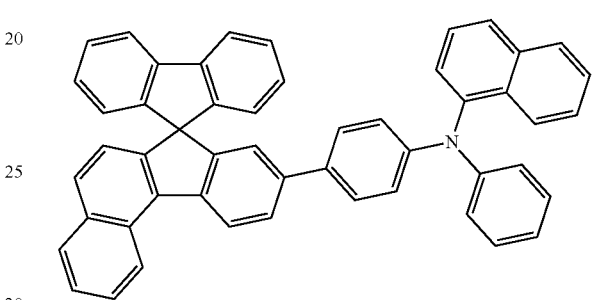
1-15
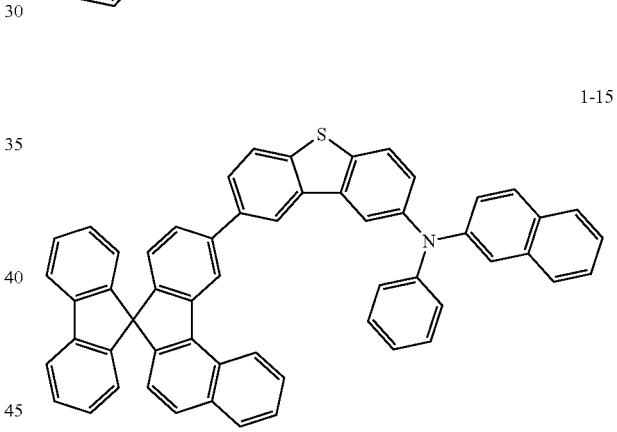
1-16
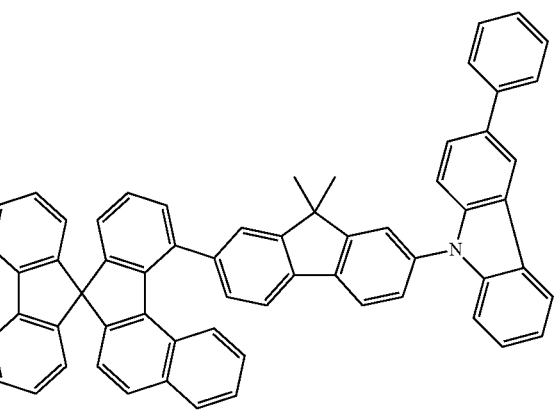

1-17
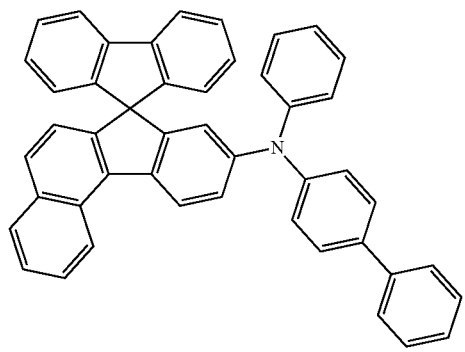
1-18
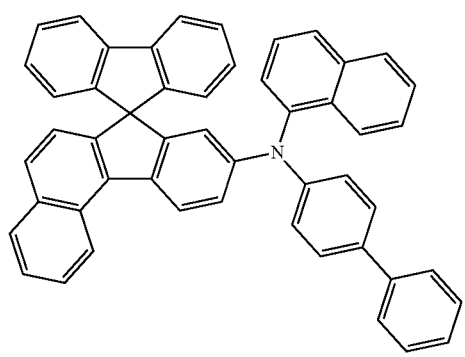
1-19
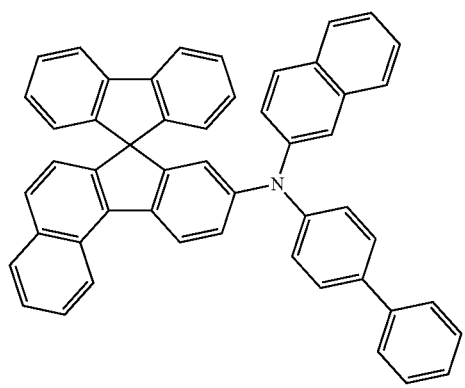
1-20
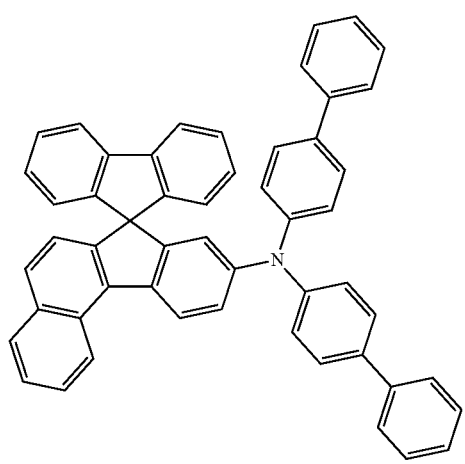
1-21
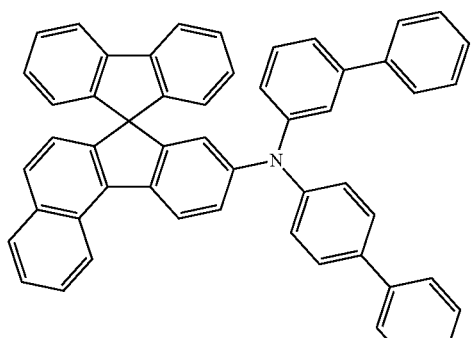
1-22
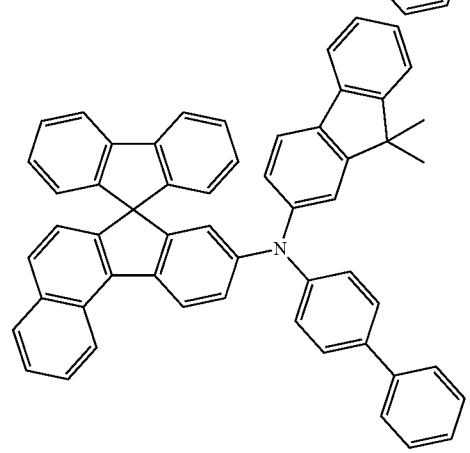
1-23
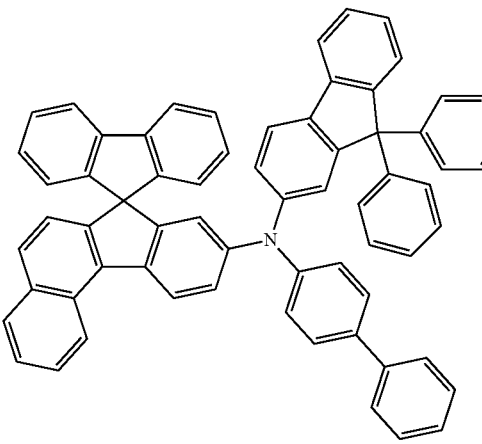
1-24
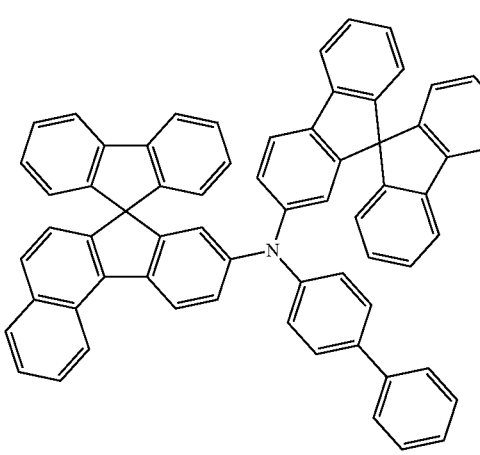

1-25
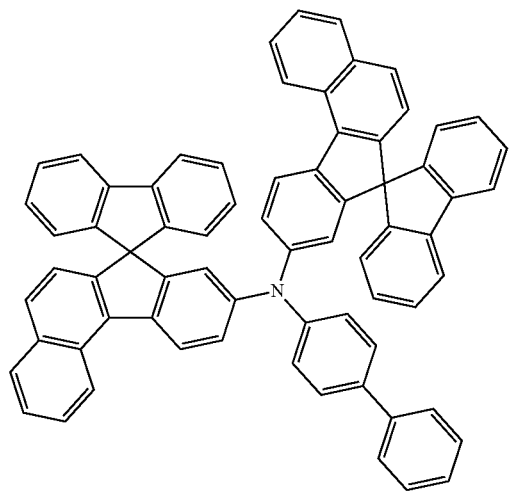
1-26
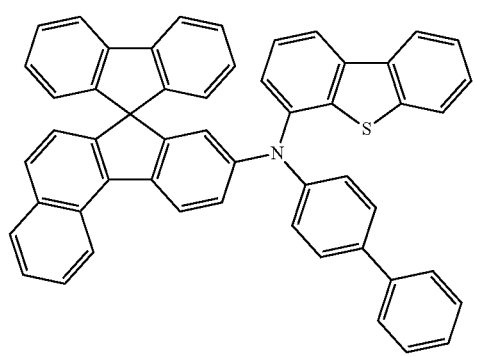
1-27
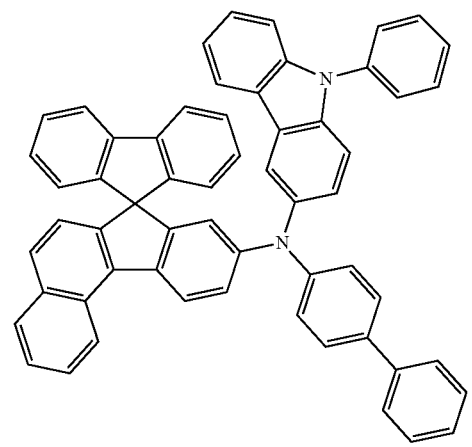
1-28
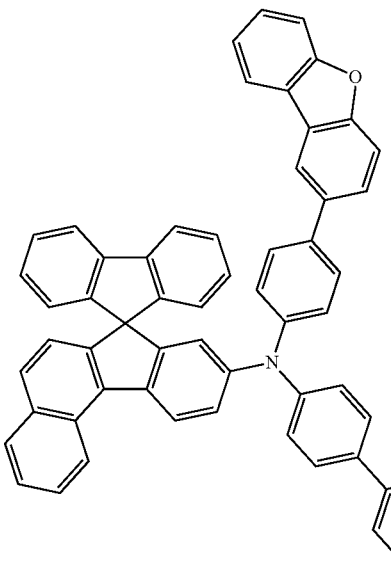
1-29
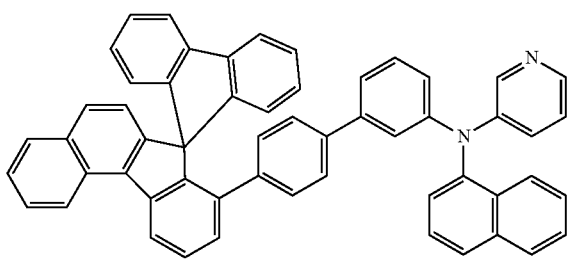
1-30
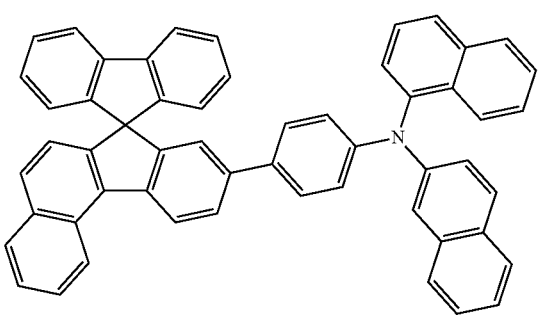
1-31
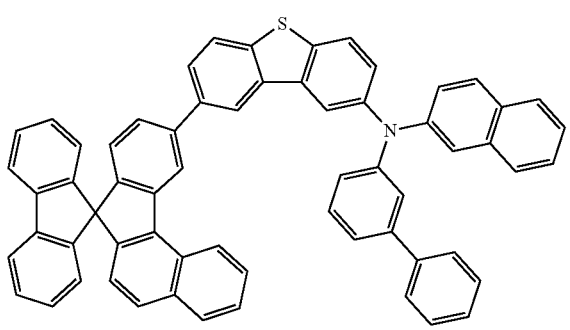

1-32
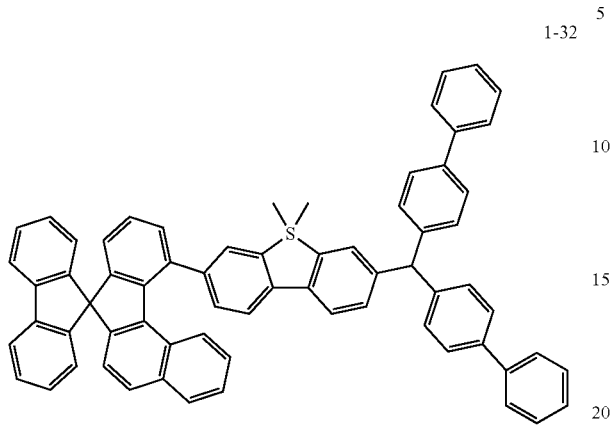
1-33
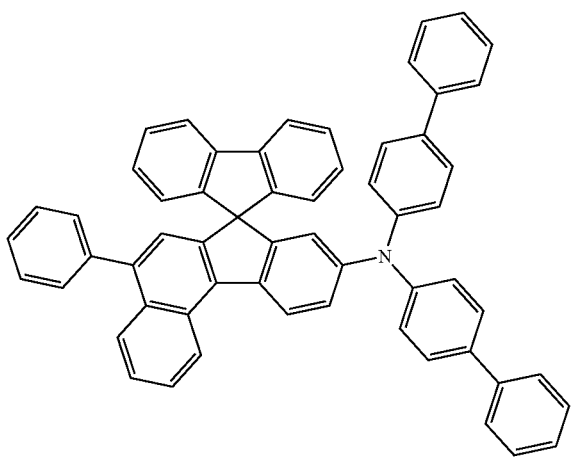
1-34
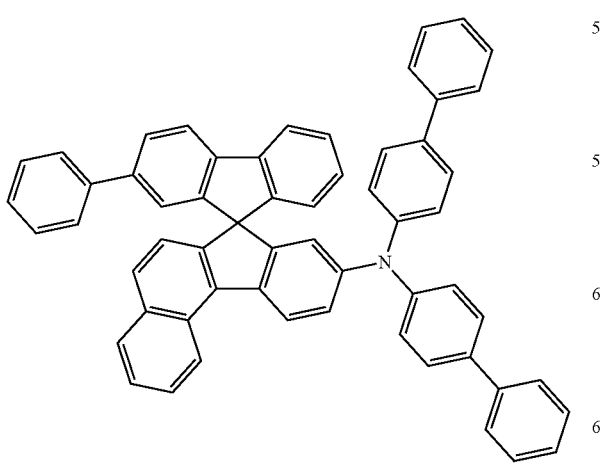
1-35
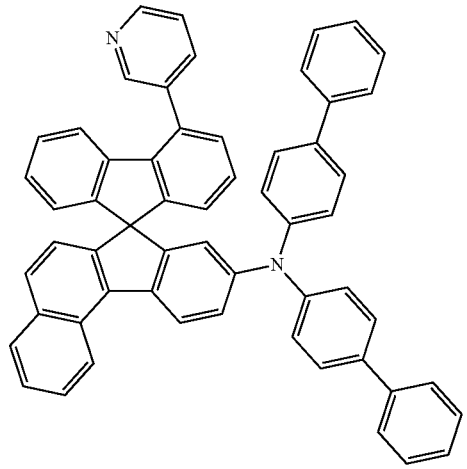
1-36
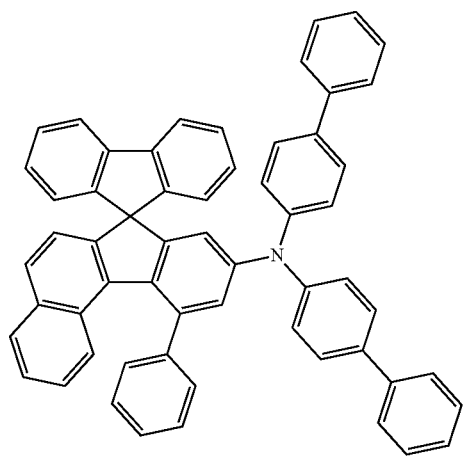
1-37
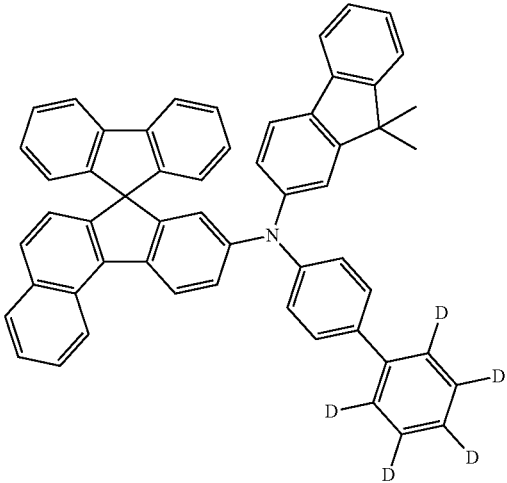

121
-continued
1-38
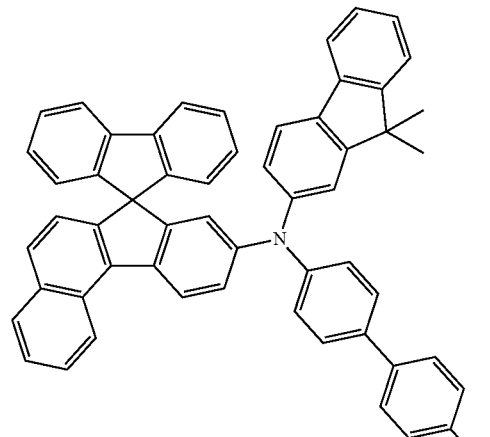
1-39
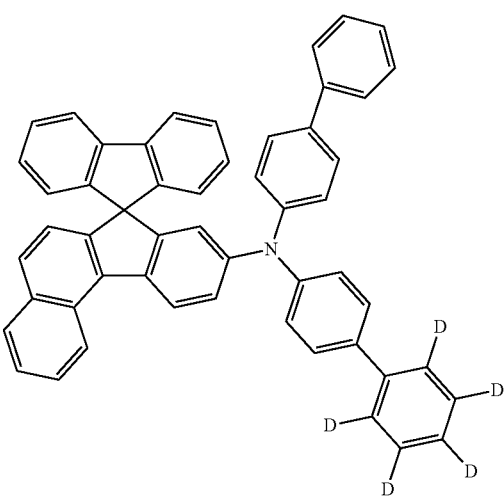
1-40
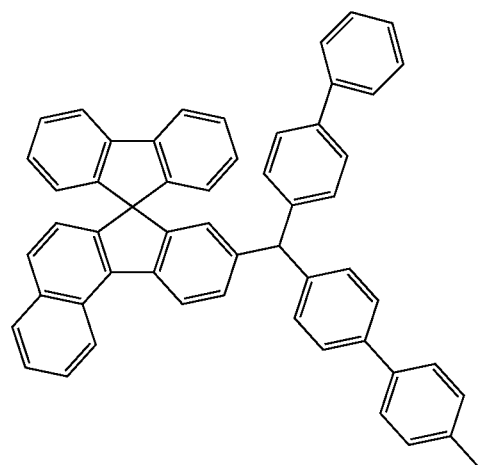
122
-continued
2-1
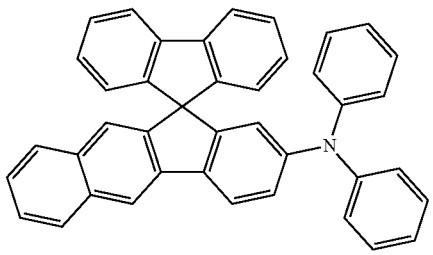
2-2
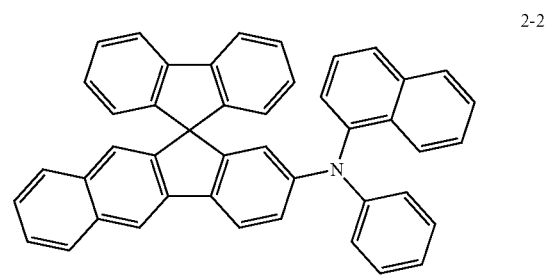
2-3
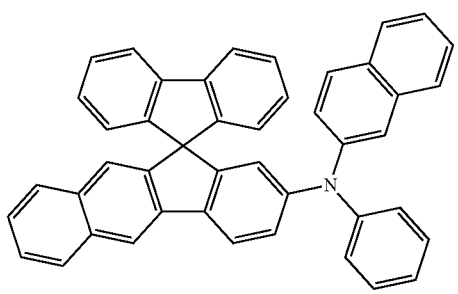
2-4
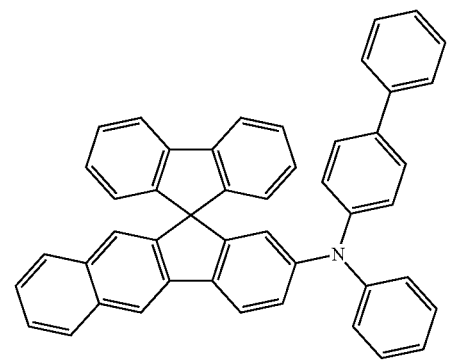
2-5
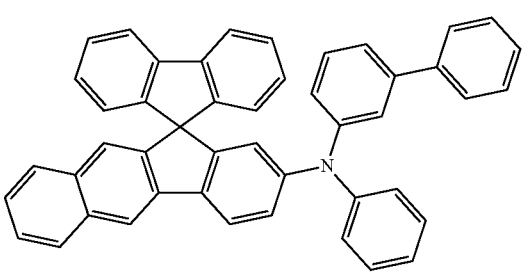

2-6
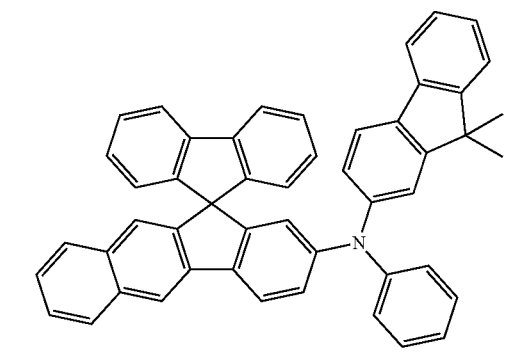
2-7
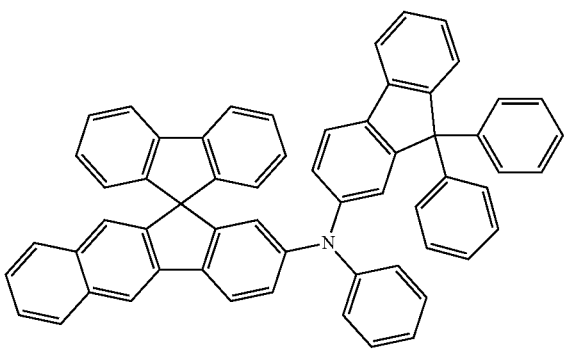
2-8
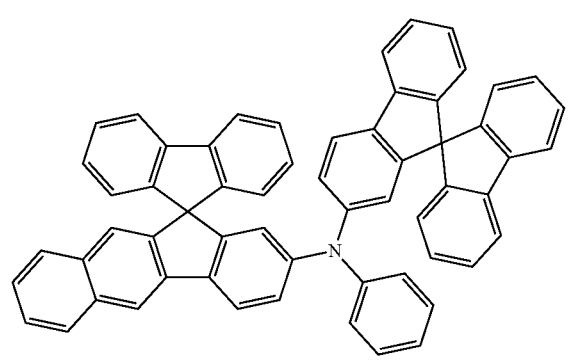
2-9
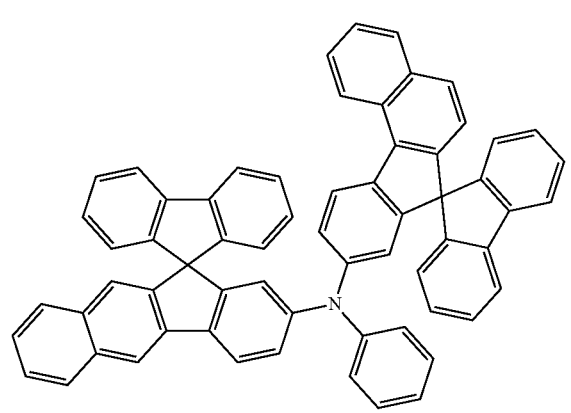
2-10
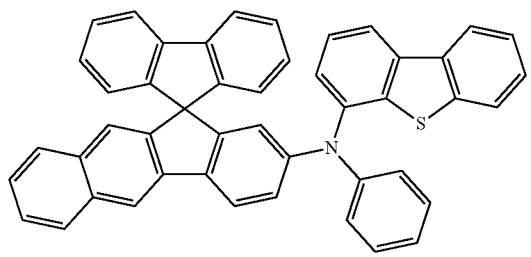
2-11
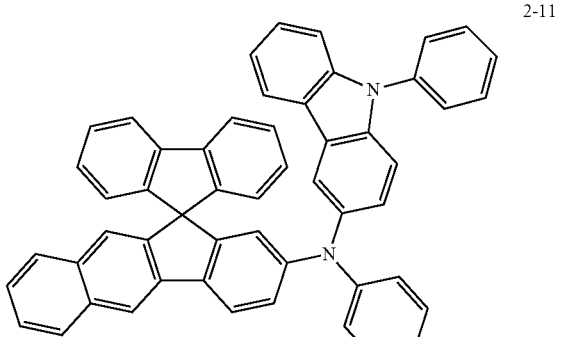
2-12
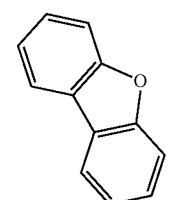
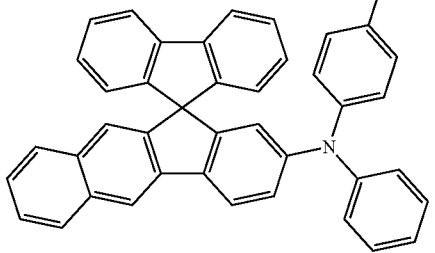
2-13
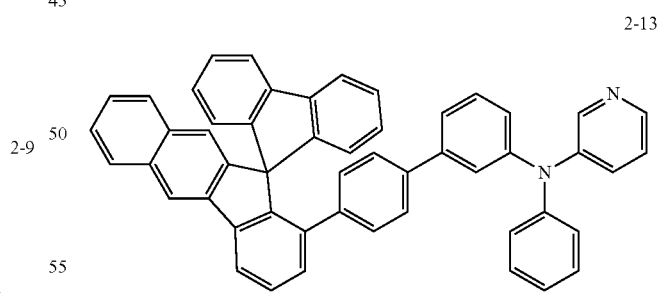
2-14
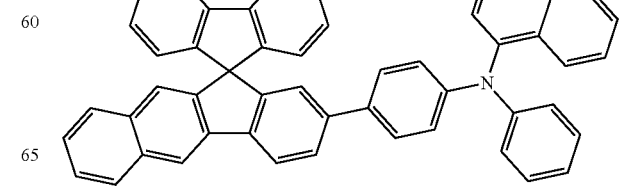

2-15
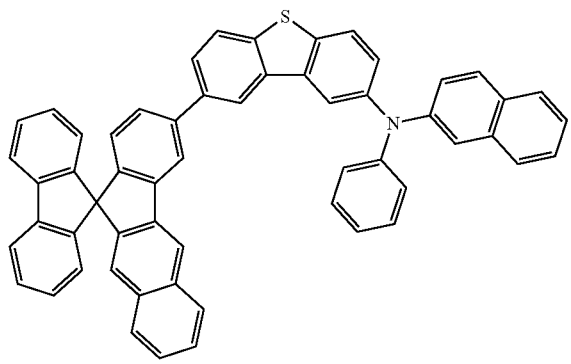
2-16
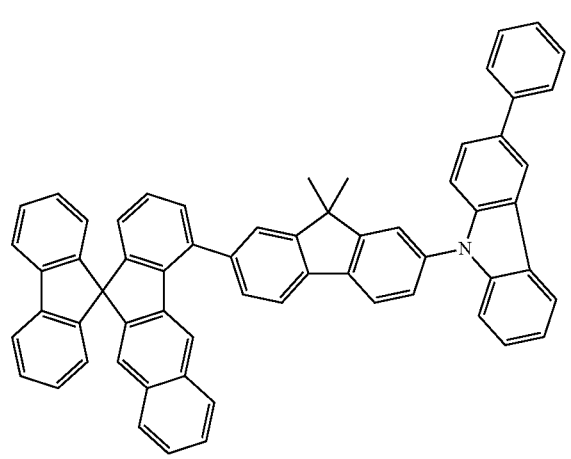
2-17
2-18
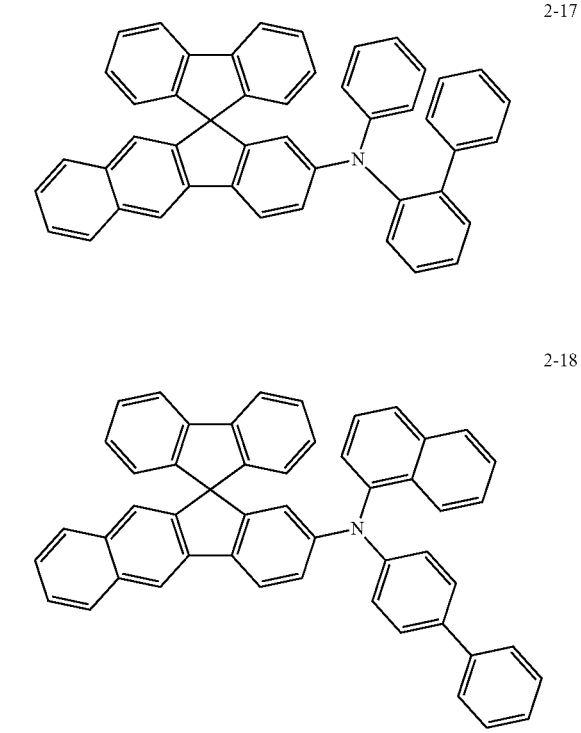
2-19
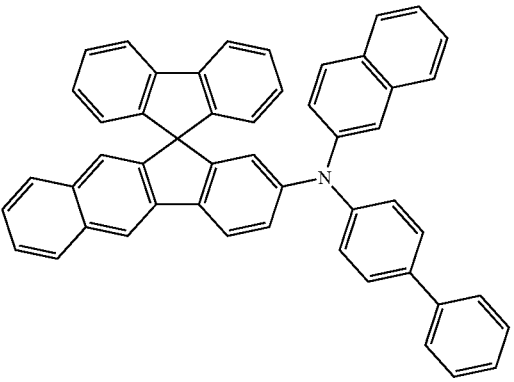
2-20
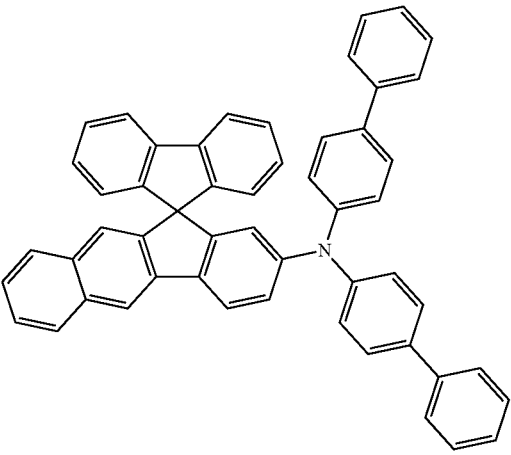
2-21
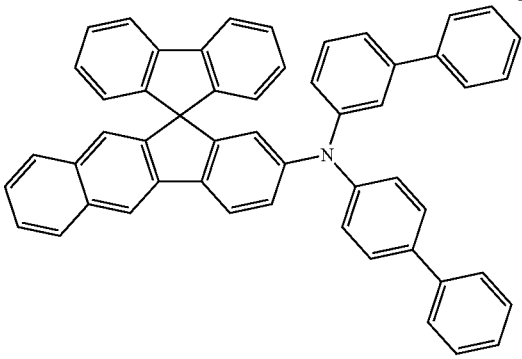
2-22
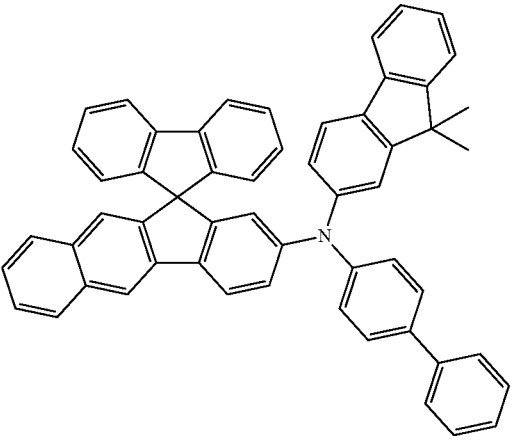

2-23
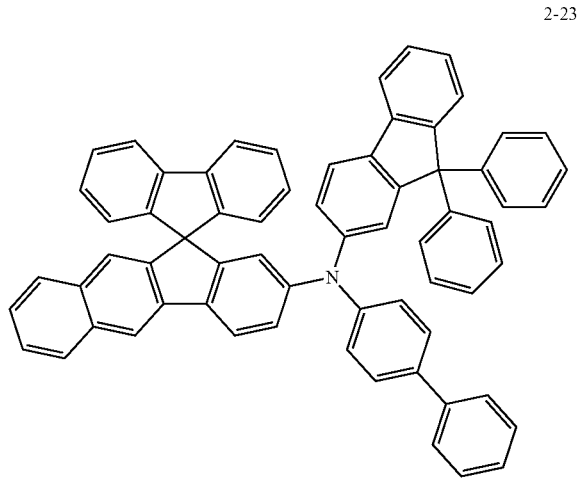
2-24
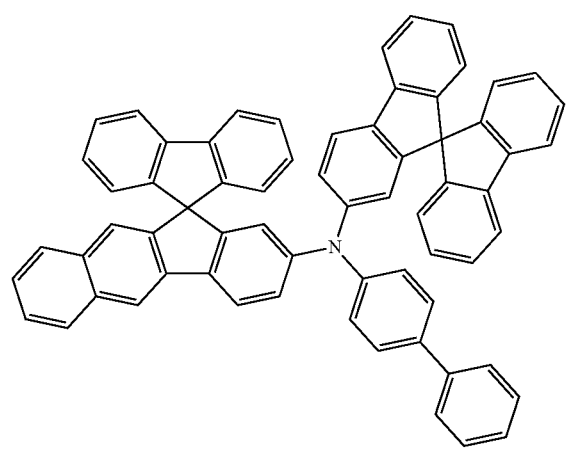
2-25
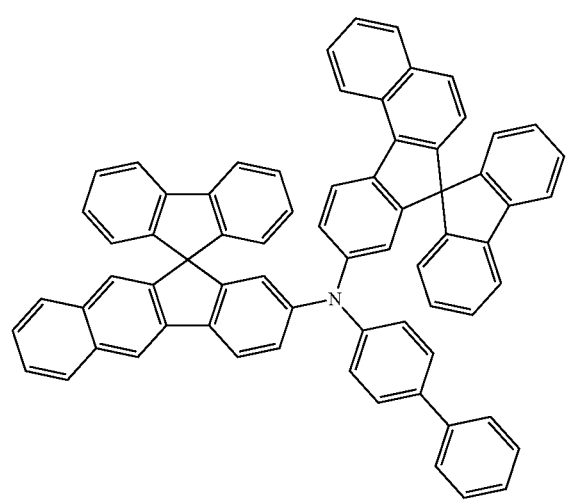
2-26
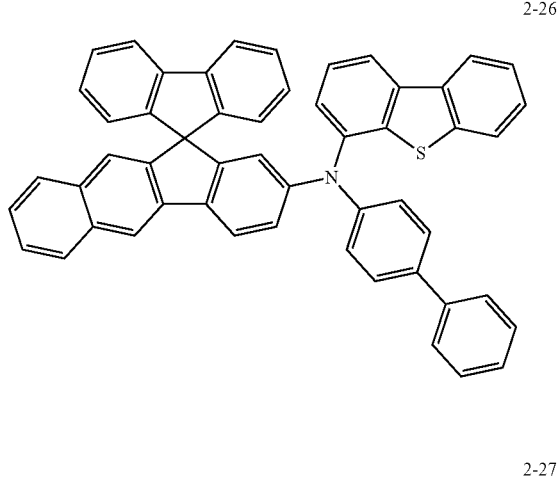
2-27
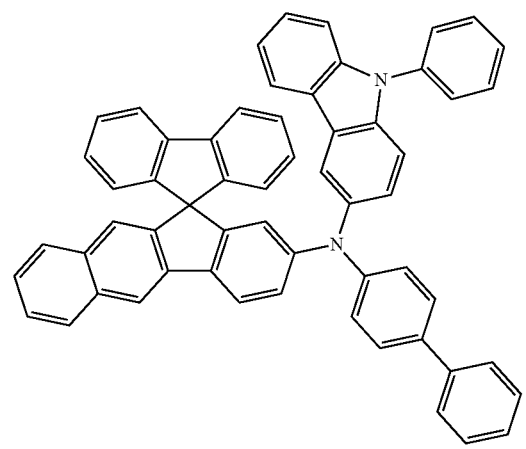
2-28
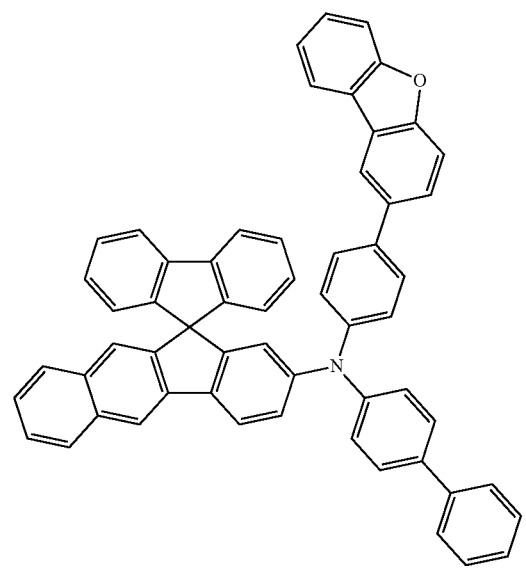

2-29
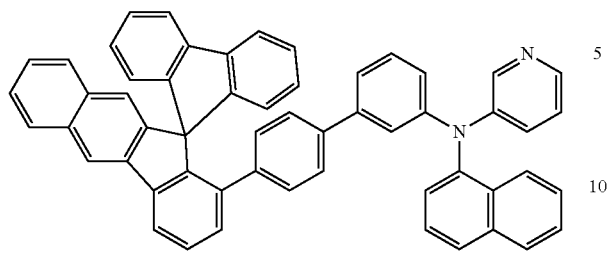
2-30
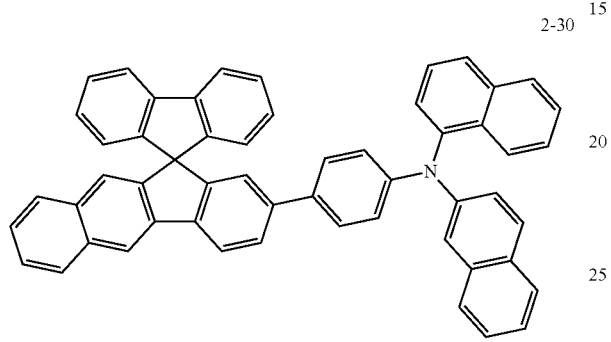
2-31
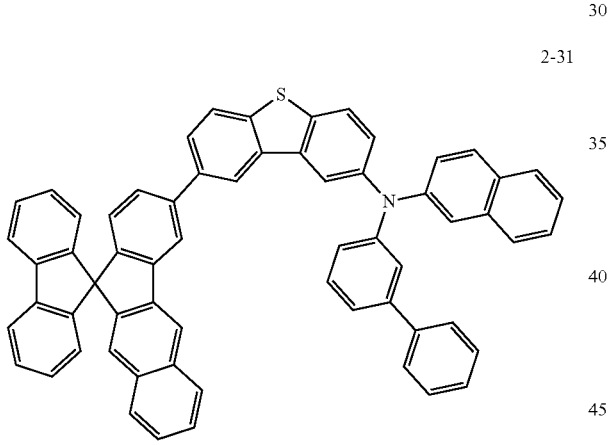
2-32
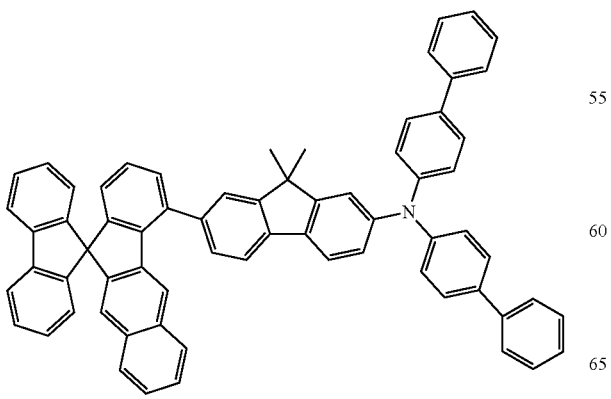
2-33
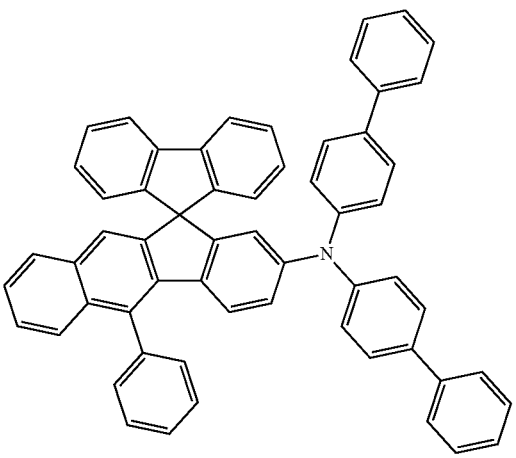
2-34
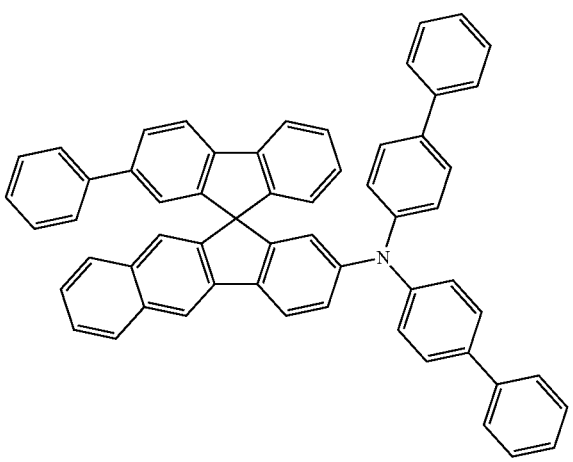
2-35
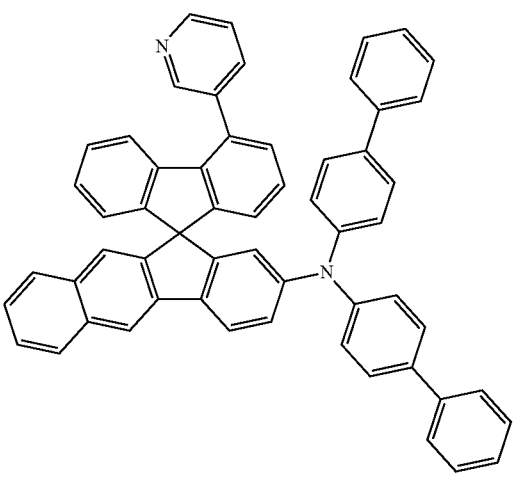

2-36
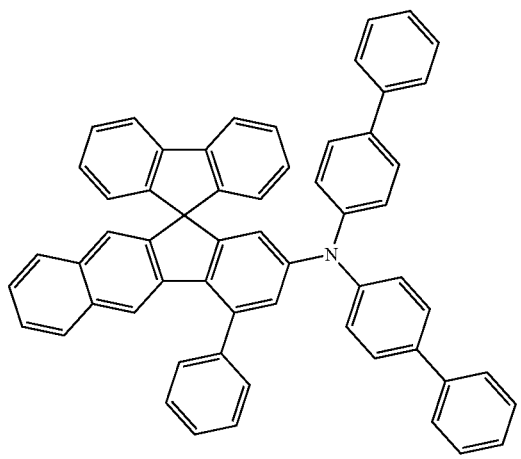
2-39
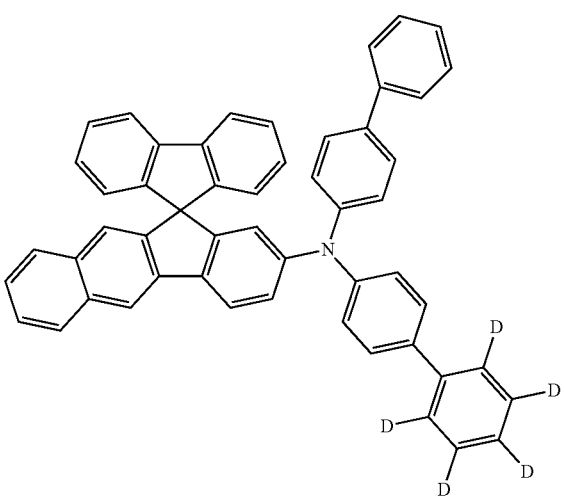
2-37
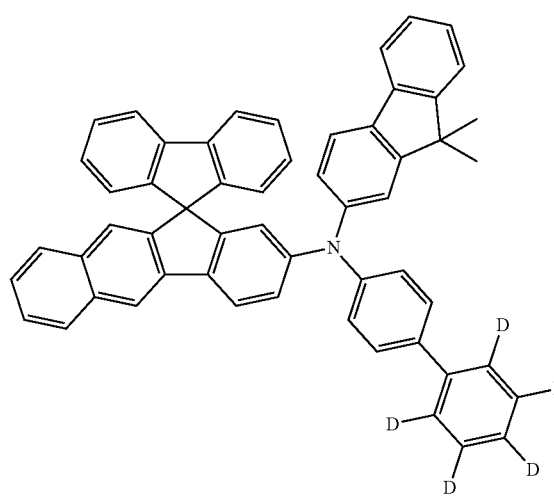
2-40
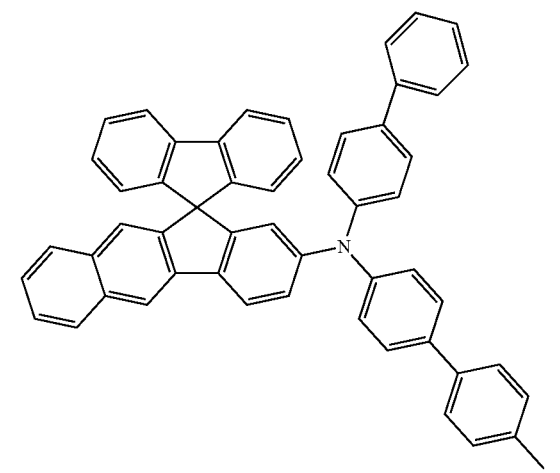
2-38
3-1
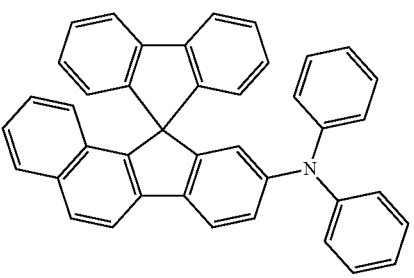
3-2
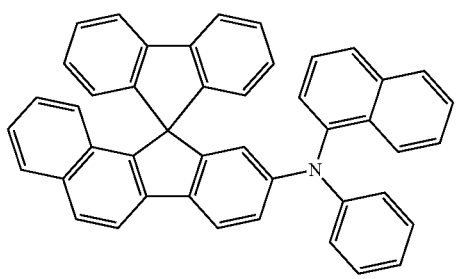

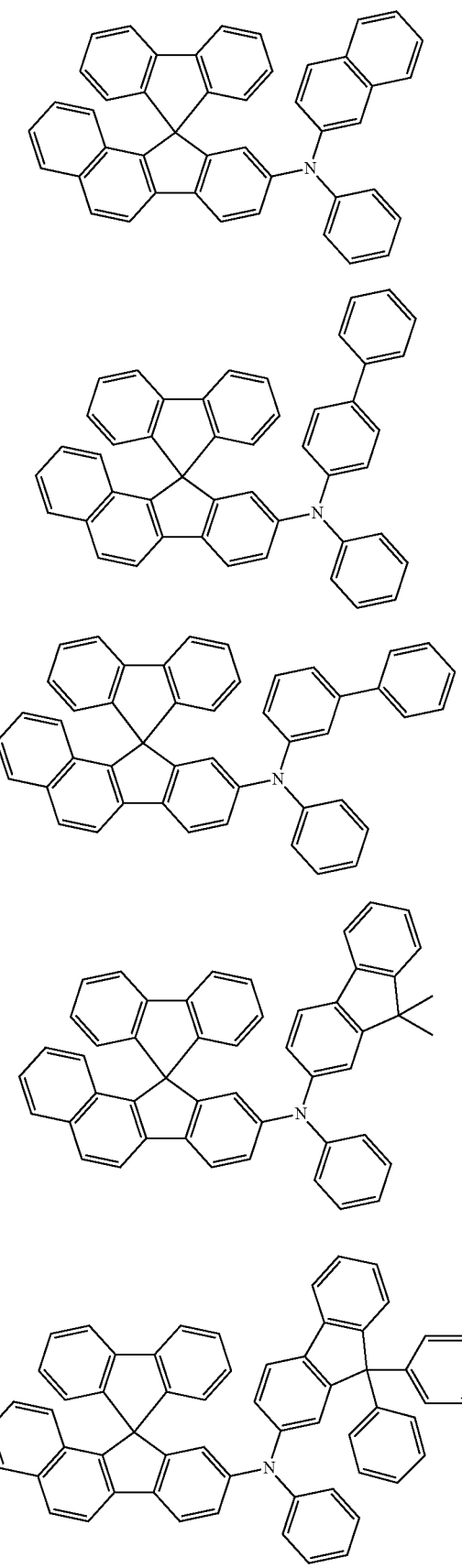
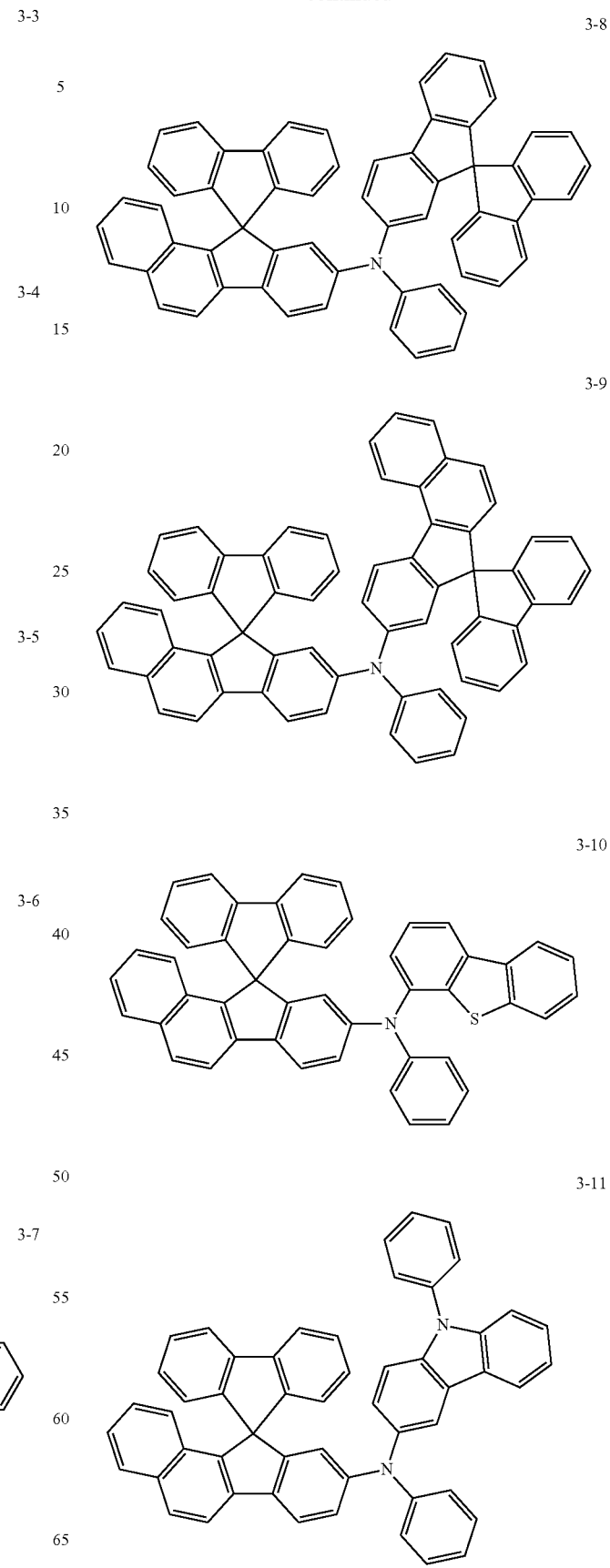

-continued
3-12
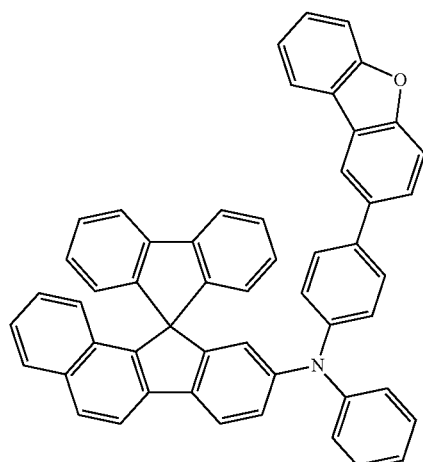
3-13
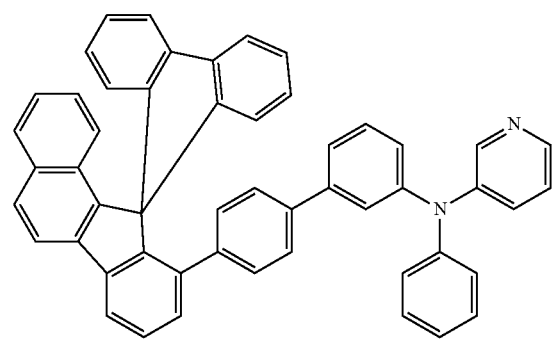
3-14
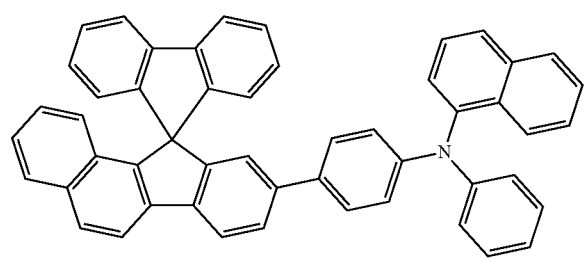
3-15
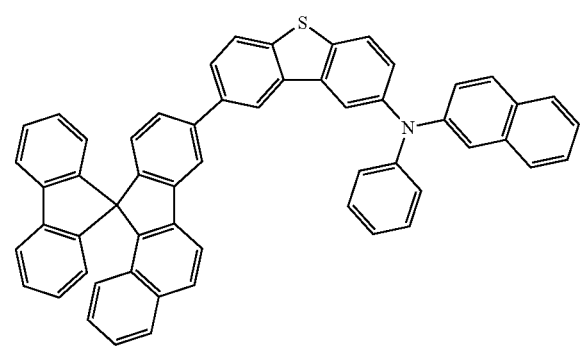
-continued
3-16
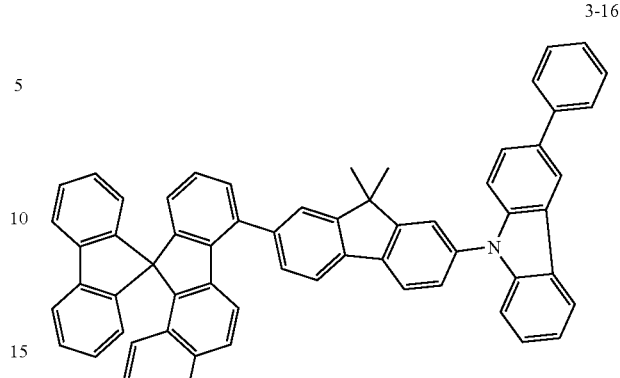
3-17
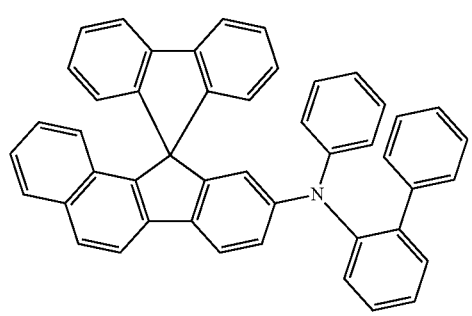
3-18
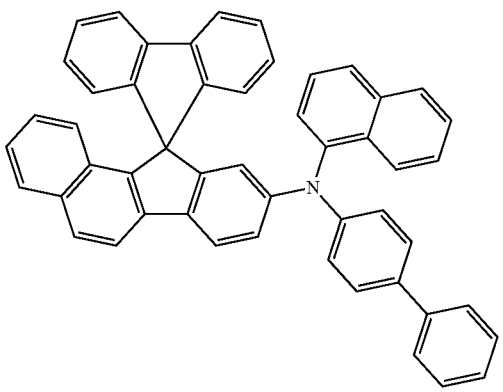
3-19
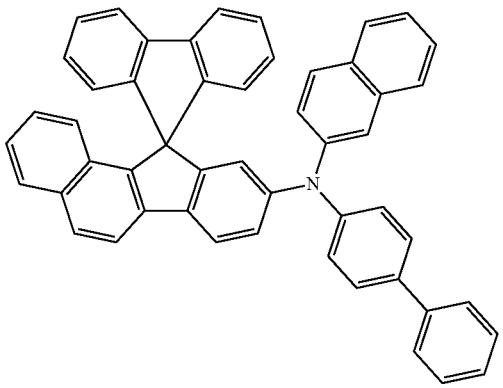

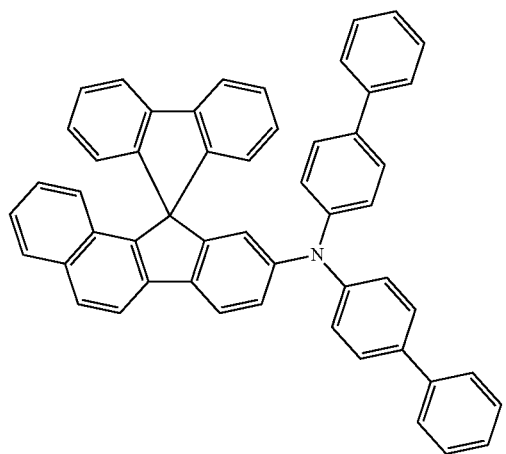
3-20
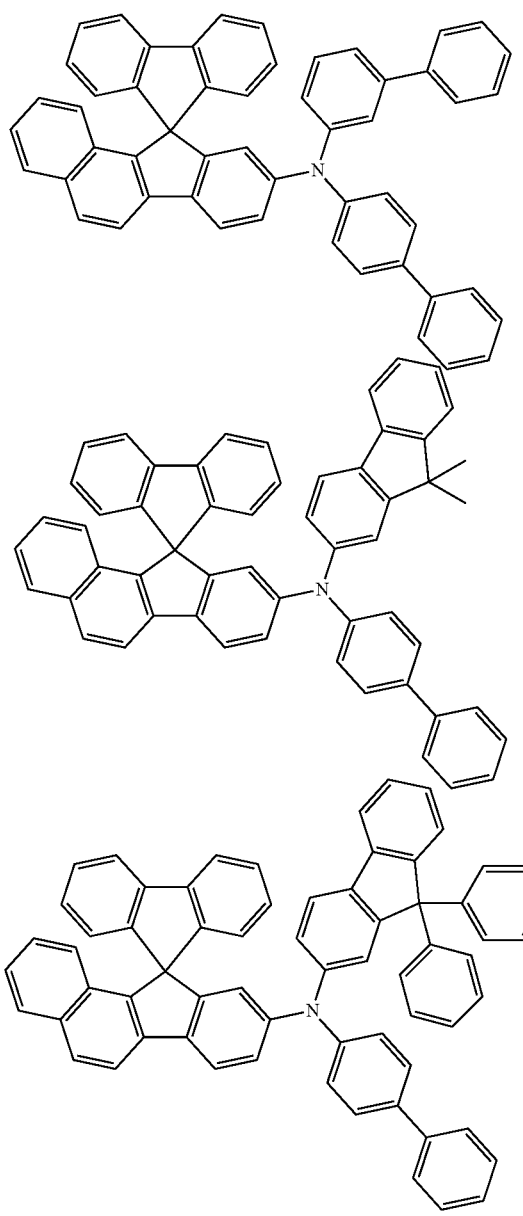
3-21
3-22
3-23
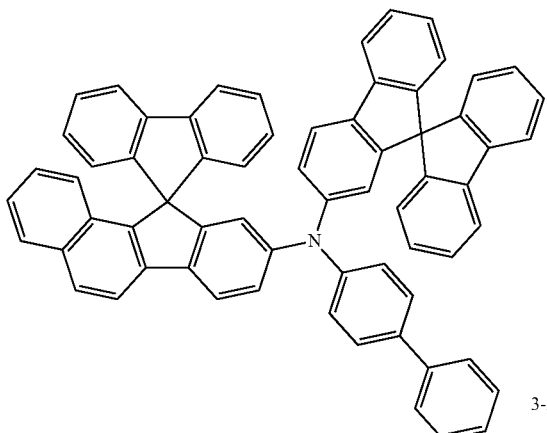
3-24
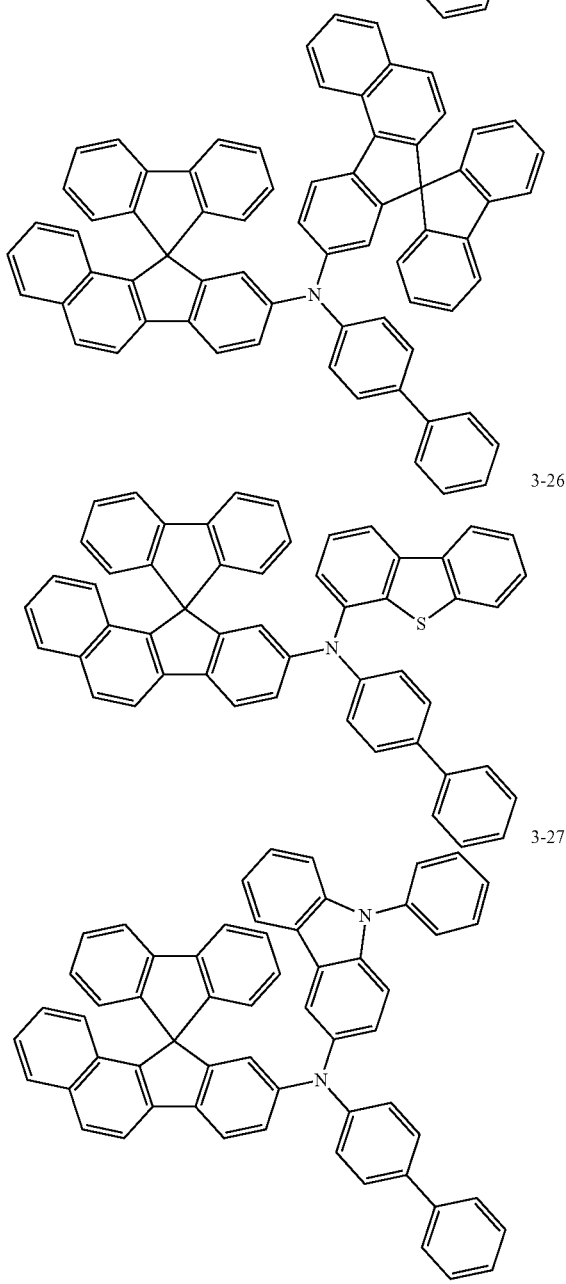
3-25
3-26
3-27

3-28
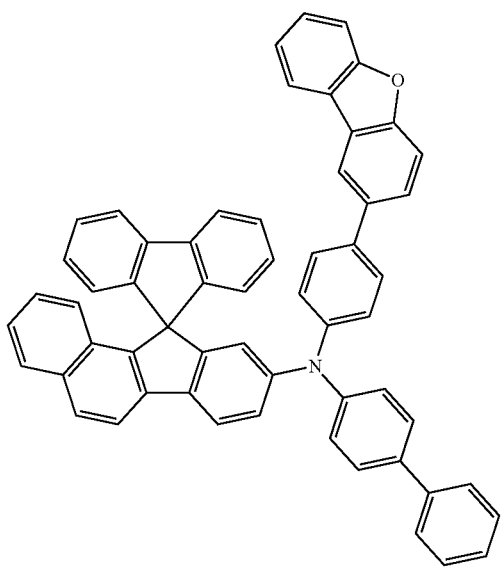
3-29
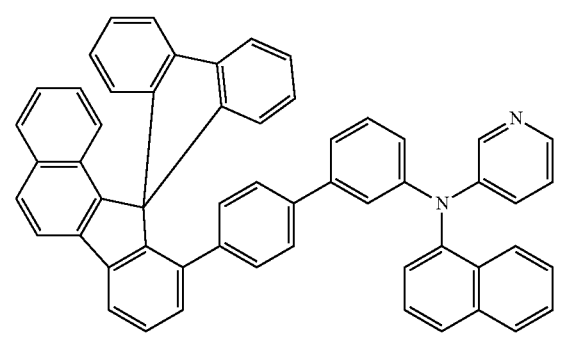
3-30
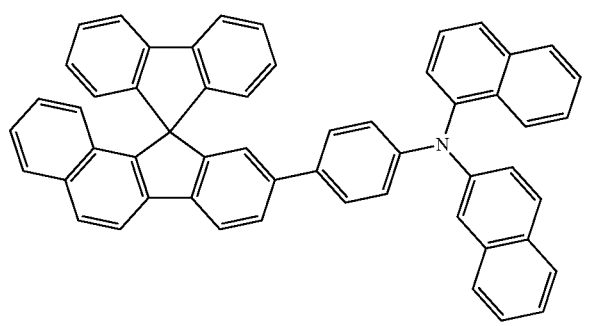
3-31
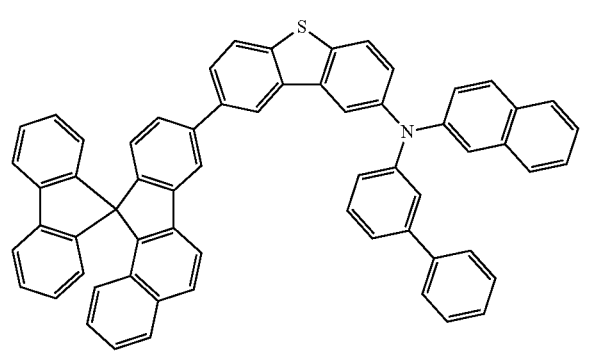
3-32
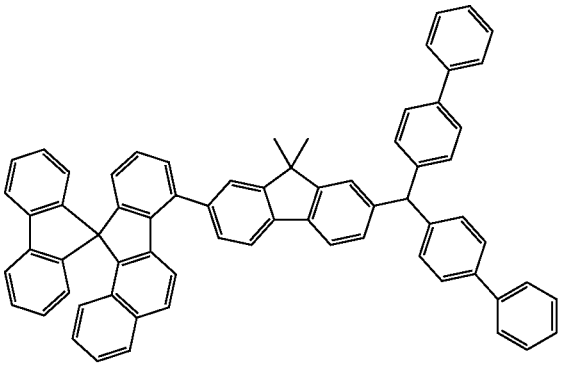
3-33
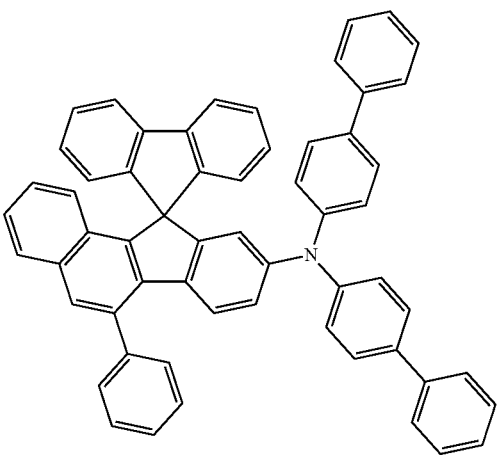
3-34
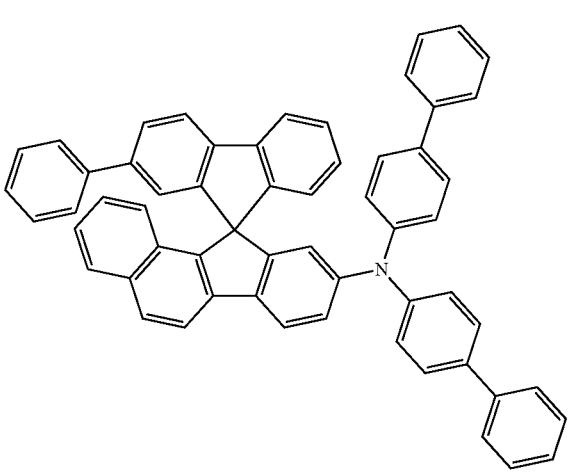

3-35
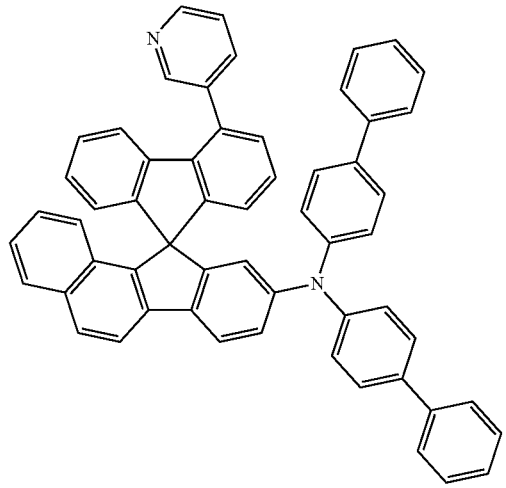
3-36
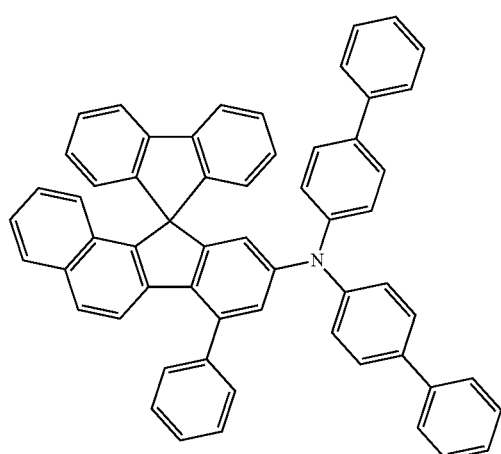
3-37
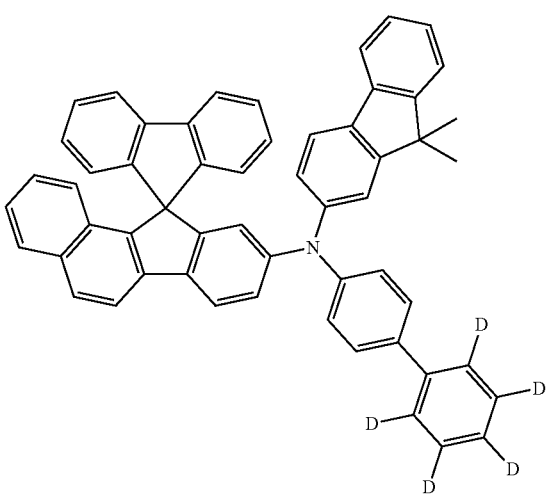
3-38
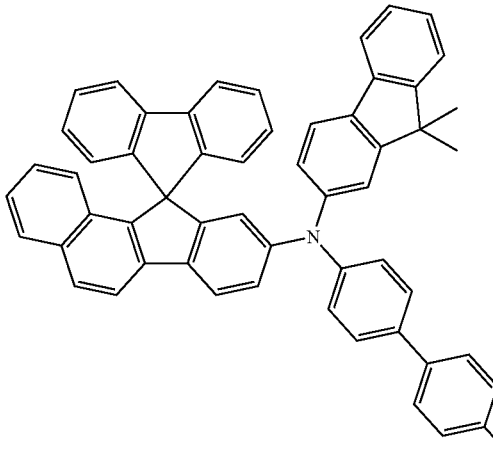
3-39
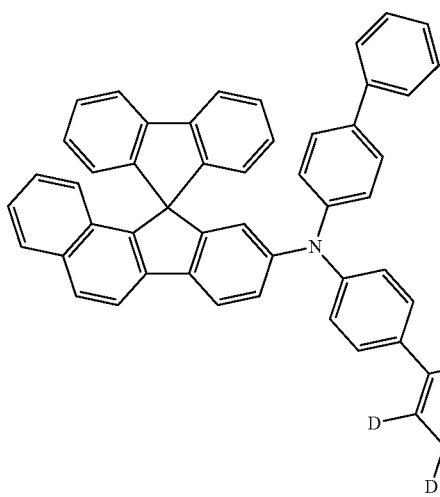
3-40
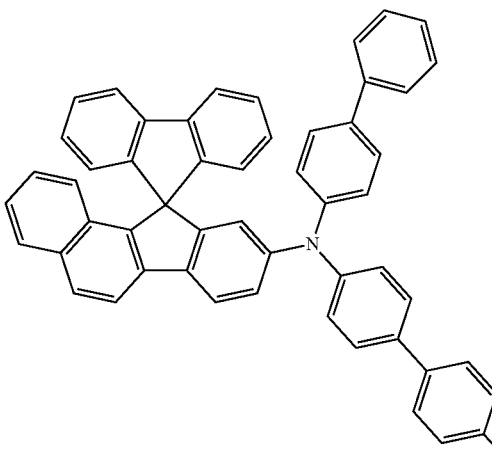
6. An organic electric element comprising: a first electrode; a second electrode; and an organic material layer positioned between the first electrode and the second electrode, wherein the organic material layer comprises the compound according to claim 1.

7. The organic electric element of claim 6, further comprising a light efficiency enhancing layer formed on one side of the first electrode opposite to the organic material layer and/or one side of the second electrode opposite to the organic material layer.

8. The organic electric element of claim 6, wherein the organic material layer is formed by a process selected from the group consisting of a spin coating process, a nozzle printing process, an inkjet printing process, a slot coating process, a dip coating process, and a roll-to-roll process.

9. The organic electric element of claim 6, comprising the compound as a hole transport material.

10. An organic electric element comprising: a first electrode; a second electrode; and an organic material layer positioned between the first electrode and the second electrode; wherein the organic material layer comprises a mixture of two or more compounds according to claim 1, wherein the compounds have different structures.

11. An electronic device comprising a display device comprising the organic electric element of claim 6; and a control part driving the display device.

12. The electronic device according to claim 11, wherein the organic electric element is at least one selected from the group consisting of an OLED, an organic solar cell, an organic photo conductor (OPC), an organic transistor (organic TFT) and an element for monochromic or white illumination.

* * * * *